US012558236B2

(12) United States Patent
Stein

(10) Patent No.: US 12,558,236 B2
(45) Date of Patent: Feb. 24, 2026

(54) SENSORIZED KNEE ARTHROPLASTY UTILIZING AN INTRAOPERATIVE SENSOR SYSTEM

(71) Applicant: DePuy Ireland Unlimited Company, Ringaskiddy (IE)

(72) Inventor: Marc Stein, Phoenix, AZ (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 190 days.

(21) Appl. No.: 18/350,723

(22) Filed: Jul. 11, 2023

(65) Prior Publication Data

US 2024/0041619 A1 Feb. 8, 2024

Related U.S. Application Data

(60) Provisional application No. 63/388,240, filed on Jul. 11, 2022.

(51) Int. Cl.
*A61F 2/46* (2006.01)
*A61B 5/00* (2006.01)
(Continued)

(52) U.S. Cl.
CPC ............ *A61F 2/4657* (2013.01); *A61B 5/067* (2013.01); *A61B 5/742* (2013.01); *A61F 2/3094* (2013.01); *A61F 2/3859* (2013.01); *A61F 2/389* (2013.01); *A61F 2002/4666* (2013.01); *A61F 2002/4668* (2013.01)

(58) Field of Classification Search
CPC ........ A61F 2/38; A61F 2/4684; A61F 2/4657; A61F 2/76; A61F 2002/4666; A61B 17/562
See application file for complete search history.

(56) References Cited

U.S. PATENT DOCUMENTS 4,856,993 A 8/1989 Maness et al.
4,899,761 A 2/1990 Brown et al.
(Continued)

FOREIGN PATENT DOCUMENTS

CN 101849864 A 10/2010
DE 10335410 A1 2/2005
(Continued)

OTHER PUBLICATIONS

PCT International Search Report and Written Opinion for International Application No. PCT/US2023/070001, Jan. 11, 2024, 9 pages.

(Continued)

*Primary Examiner* — Samuel S Hanna
(74) *Attorney, Agent, or Firm* — Barnes & Thornburg LLP

(57) ABSTRACT

Systems and techniques can be provided to generate sensorized insights into the characteristics of a knee joint space during a knee replacement procedure. In some implementations, a sensor support body carrying one or more sensors can be used to measure and inform the clinician of the varus/valgus angles of the tibia and femur, allowing the clinician to adjust the surgical procedure to accommodate the measured angles. The clinician may simulate changes to the load balance across the knee joint in response to potential dimensional changes to the knee joint prior to actually surgically implementing the changes.

24 Claims, 38 Drawing Sheets

(51) Int. Cl.

| | |
|---|---|
| *A61B 5/06* | (2006.01) |
| *A61F 2/30* | (2006.01) |
| *A61F 2/38* | (2006.01) |

(56) References Cited

U.S. PATENT DOCUMENTS

| | | | |
|---|---|---|---|
| 5,125,408 | A | 6/1992 | Basser |
| 5,197,488 | A | 3/1993 | Kovacevic |
| 5,213,112 | A | 5/1993 | Niwa et al. |
| 5,326,363 | A | 7/1994 | Aikins |
| 5,360,016 | A | 11/1994 | Kovacevic |
| 5,443,518 | A | 8/1995 | Insall |
| 5,470,354 | A | 11/1995 | Hershberger et al. |
| 5,496,352 | A | 3/1996 | Renger |
| 5,656,785 | A | 8/1997 | Trainor et al. |
| 5,733,292 | A | 3/1998 | Gustilo et al. |
| 5,871,018 | A | 2/1999 | Delp et al. |
| 5,935,086 | A | 8/1999 | Beacon et al. |
| 6,165,142 | A | 12/2000 | Bar |
| 6,610,096 | B2 | 8/2003 | Macdonald |
| 6,706,005 | B2 | 3/2004 | Roy et al. |
| 6,821,299 | B2 | 11/2004 | Kirking et al. |
| 6,856,834 | B2 | 2/2005 | Treppo et al. |
| 7,412,897 | B2 | 8/2008 | Crottet et al. |
| 7,575,602 | B2 | 8/2009 | Amirouche et al. |
| 7,578,821 | B2 | 8/2009 | Fisher et al. |
| 7,615,055 | B2 | 11/2009 | Disilvestro |
| 7,632,283 | B2 | 12/2009 | Heldreth |
| 7,794,499 | B2 | 9/2010 | Navarro et al. |
| 7,849,751 | B2 | 12/2010 | Clark et al. |
| 8,118,815 | B2 | 2/2012 | Van Der Walt |
| 8,197,489 | B2 | 6/2012 | Chessar et al. |
| 8,211,041 | B2 | 7/2012 | Fisher et al. |
| 8,231,631 | B2 | 7/2012 | Lavallee et al. |
| 8,323,290 | B2 | 12/2012 | Metzger et al. |
| 8,394,104 | B2 | 3/2013 | Disilvestro |
| 8,551,023 | B2 | 10/2013 | Sherman et al. |
| 8,556,830 | B2 | 10/2013 | Sherman et al. |
| 8,562,617 | B2 | 10/2013 | Chessar et al. |
| 8,597,210 | B2 | 12/2013 | Sherman et al. |
| 8,721,568 | B2 | 5/2014 | Rock et al. |
| 8,734,454 | B2 | 5/2014 | Disilvestro |
| 8,740,817 | B2 | 6/2014 | Sherman et al. |
| 8,926,530 | B2 | 1/2015 | Stein et al. |
| 9,538,953 | B2 | 1/2017 | Sherman et al. |
| 9,649,119 | B2 | 5/2017 | Rock et al. |
| 9,808,356 | B2 | 11/2017 | Haight et al. |
| 10,070,973 | B2 | 9/2018 | Sherman et al. |
| 10,098,761 | B2 | 10/2018 | Sherman et al. |
| 10,206,792 | B2 | 2/2019 | Sherman et al. |
| 11,051,955 | B2 | 7/2021 | Sherman et al. |
| 11,055,648 | B2 | 7/2021 | Disilvestro et al. |
| 11,068,822 | B2 | 7/2021 | Disilvestro et al. |
| 11,096,801 | B2 | 8/2021 | Sherman et al. |
| 2003/0069644 | A1 | 4/2003 | Kovacevic et al. |
| 2003/0187452 | A1 | 10/2003 | Smith et al. |
| 2003/0236472 | A1 | 12/2003 | Van Hoeck et al. |
| 2004/0019382 | A1 | 1/2004 | Amirouche et al. |
| 2004/0064073 | A1 | 4/2004 | Heldreth |
| 2004/0064191 | A1 | 4/2004 | Wasielewski |
| 2004/0243148 | A1 | 12/2004 | Wasielewski |
| 2005/0010302 | A1 | 1/2005 | Dietz et al. |
| 2005/0177169 | A1 | 8/2005 | Fisher et al. |
| 2005/0177170 | A1 | 8/2005 | Fisher et al. |
| 2005/0267485 | A1 | 12/2005 | Cordes et al. |
| 2006/0149277 | A1 | 7/2006 | Cinquin et al. |
| 2006/0155295 | A1 | 7/2006 | Supper et al. |
| 2006/0241569 | A1 | 10/2006 | Disilvestro |
| 2007/0219561 | A1 | 9/2007 | Lavallee et al. |
| 2007/0233144 | A1 | 10/2007 | Lavallee et al. |

| | | | |
|---|---|---|---|
| 2007/0239165 | A1 | 10/2007 | Amirouche |
| 2007/0244488 | A1 | 10/2007 | Metzger et al. |
| 2008/0058946 | A1 | 3/2008 | Dietz |
| 2008/0306413 | A1 | 12/2008 | Crottet et al. |
| 2009/0005708 | A1 | 1/2009 | Johanson et al. |
| 2009/0018544 | A1 | 1/2009 | Heavener |
| 2009/0088674 | A1 | 4/2009 | Caillouette et al. |
| 2009/0138019 | A1 | 5/2009 | Wasielewski |
| 2009/0326544 | A1 | 12/2009 | Chessar et al. |
| 2010/0023067 | A1 | 1/2010 | Disilvestro |
| 2010/0063508 | A1 | 3/2010 | Borja et al. |
| 2010/0063509 | A1 | 3/2010 | Borja et al. |
| 2010/0064216 | A1 | 3/2010 | Borja et al. |
| 2010/0069911 | A1 | 3/2010 | Borja et al. |
| 2010/0137869 | A1 | 6/2010 | Borja et al. |
| 2010/0198275 | A1 | 8/2010 | Chana et al. |
| 2010/0217156 | A1 | 8/2010 | Fisher et al. |
| 2010/0249533 | A1 | 9/2010 | Pierce et al. |
| 2010/0249658 | A1 | 9/2010 | Sherman et al. |
| 2010/0249659 | A1 | 9/2010 | Sherman et al. |
| 2010/0249660 | A1 | 9/2010 | Sherman et al. |
| 2010/0249777 | A1 | 9/2010 | Sherman et al. |
| 2010/0249789 | A1 | 9/2010 | Rock et al. |
| 2010/0249790 | A1 | 9/2010 | Roche |
| 2010/0249791 | A1 | 9/2010 | Roche |
| 2010/0250571 | A1 | 9/2010 | Pierce et al. |
| 2011/0251694 | A1 | 10/2011 | Wasielewski |
| 2012/0172762 | A1 | 7/2012 | Boyer et al. |
| 2012/0232429 | A1 | 9/2012 | Fischer et al. |
| 2012/0283600 | A1 | 11/2012 | Stein |
| 2013/0013076 | A1 | 1/2013 | Fisher et al. |
| 2013/0023794 | A1 | 1/2013 | Stein et al. |
| 2013/0079669 | A1 | 3/2013 | Stein et al. |
| 2013/0079675 | A1 | 3/2013 | Stein et al. |
| 2013/0261502 | A1 | 10/2013 | Sherman et al. |
| 2013/0261503 | A1 | 10/2013 | Sherman et al. |
| 2013/0261505 | A1 | 10/2013 | Sherman et al. |
| 2014/0018707 | A1 | 1/2014 | Sherman et al. |
| 2016/0007909 | A1 | 1/2016 | Singh et al. |
| 2021/0330478 | A1 | 10/2021 | Sherman et al. |
| 2021/0378843 | A1 | 12/2021 | Sherman et al. |
| 2022/0096222 | A1 | 3/2022 | Huff et al. |
| 2022/0096248 | A1 | 3/2022 | Dressler et al. |
| 2022/0354512 | A1 | 11/2022 | Rock et al. |
| 2023/0059247 | A1* | 2/2023 | Gannoe ............... A61B 17/154 |

FOREIGN PATENT DOCUMENTS

| | | | |
|---|---|---|---|
| EP | 720834 | A2 | 7/1996 |
| EP | 1402857 | A2 | 3/2004 |
| EP | 1645229 | A1 | 4/2006 |
| EP | 1707159 | A1 | 10/2006 |
| EP | 1814471 | A2 | 8/2007 |
| JP | 2007054488 | A | 3/2007 |
| JP | 2010063783 | A | 3/2010 |
| JP | 2010240407 | A | 10/2010 |
| JP | 2014533974 | A | 12/2014 |
| WO | 2005023120 | A1 | 3/2005 |
| WO | 2005089681 | A2 | 9/2005 |
| WO | 2006078236 | A1 | 7/2006 |
| WO | 2010011978 | A1 | 1/2010 |
| WO | 2010022272 | A1 | 2/2010 |
| WO | 2012004580 | A1 | 1/2012 |
| WO | 2013044174 | A2 | 3/2013 |

OTHER PUBLICATIONS

PCT International Search Report for International Application No. PCT/US23/69997, Nov. 16, 2023, 3 pages.

PCT International Written Opinion for International Application No. PCT/US2023/69989, mailed Mar. 13, 2024, 5 pages.

* cited by examiner

12

104B

102

14

GENERATE CURRENT LOAD AND
ALIGNMENT INFORMATION                    470

RECEIVE SIMULATION INPUT                 472

DETERMINE PROJECTED FORCE AND/
OR ALIGNMENT INFORMATION                 474

DISPLAY PROJECTED INFORMATION            476

SENSORIZED KNEE ARTHROPLASTY UTILIZING AN INTRAOPERATIVE SENSOR SYSTEM

RELATED MATTERS

This application claims the benefit of U.S. Provisional Application No. 63/388,240, filed Jul. 11, 2022, the contents of which are incorporated herein by reference in their entirety.

TECHNICAL FIELD

This disclosure relates to devices and techniques for replacing mammalian joints, including sensor devices and associated techniques for replacing a total knee joint.

BACKGROUND

The human leg includes a lower bone called a tibia and an upper bone called a femur. The tibia and femur are hinged together at the tibiofemoral joint, referred to as the knee joint. The end of the femur includes two rounded prominences called the medial and the lateral femoral condyles. The femoral condyles engage the tibia in an area called the tibial plateau that is a medial and a lateral part. The knee joint is held together by numerous ligaments, muscles and tendons. The ligament structure helps control the stability and alignment of the knee.

Disease and trauma affecting the articular surfaces of the knee joint are commonly treated by performing a partial or total knee replacement. Total knee replacement surgery, also referred to as total knee arthroplasty ("TKA"), involves surgically replacing the ends of the femur and tibia with prosthetic femoral and tibial implants, and, in some cases, replacing the patella of the knee with a patella component. In TKA, the surgeon typically affixes two prosthetic components to the patient's bone structure: one prosthetic component to the patient's femur and one prosthetic component to the patient's tibia. These components are typically known as the femoral component and the tibial component, respectively. A tibial bearing insert is inserted between the femoral component and the tibial component. The femoral component defines articular surfaces that engage concave surfaces of the top of the tibial bearing insert. The bottom of the tibial bearing insertion may be flat and engage the tibial platform defined by the tibial component.

The surgeon may balance the ligament structure across the knee during the surgical procedure to help achieve an efficacious clinical outcome and ensure survival of the knee replacement, e.g., by promoting symmetrical loading forces across the knee. The surgeon may balance with an objective of achieving a balanced flexion-extension gap without medio-lateral laxity or tightness. Accurate soft tissue balancing can contribute to patellofemoral stability, joint alignment, and resulting patient satisfaction.

In practice, soft tissue forces may be controlled by the surgeon through gap balancing prior to cutting the bones and/or ligament balancing after cutting the bones. Gap balancing techniques generally involve ligament releases performed prior to bone cuts. These ligament releases can correct fixed deformities and bring the limb into a desired alignment. Ligament balancing typically involves placement and sizing of the femoral and tibial components and balancing procedures for the ligaments after cutting the bones, such as cutting portions of one or more ligaments to release the ligaments and modify loading forces across the knee.

SUMMARY

In general, this disclosure is directed to devices and systems for facilitating joint replacement and associated joint replacement techniques. The devices, systems, and techniques of the present disclosure can be used in any partial or total joint replacement procedure performed on two or more bones separated by a joint, including hip replacement surgery, knee replacement surgery, shoulder replacement surgery, elbow replacement surgery, wrist joint replacement, ankle replacement, finger joint replacement, and knuckle joint replacement. In some specific applications, the disclosed devices and techniques are utilized in a total knee replacement surgery.

In some examples, an intraoperative surgical system for joint replacement, such as knee arthroplasty, is described that includes one or more sensors configured to measure force and/or position within a joint replacement procedure. The surgical system may include a sensor support body carrying the one or more sensors as well as a power source, a processor, memory, and wireless telemetry unit operable to communicate signals to and/or from the surgical system to an external computing device. Although the surgical system can take a variety of different forms, in some implementations, the surgical system is configured to define a joint insertion portion for use during the joint replacement procedure. The joint insertion portion can be inserted in the tibiofemoral joint space to allow the surgeon to measure force(s) across the joint space and/or anatomical positioning in three-dimensional space relative to the joint space.

In some examples, the joint insertion portion of the surgical system includes one or more force sensors that measure data indicative of the force exerted on the joint insertion portion by opposed surfaces of the tibia and femur. The sensors can measure the force of the ligaments across the joint, e.g., providing a measured output that the surgeon can use to ligament balance the joint. For example, during the TKA, the surgeon may resect the medial and lateral menisci, the anterior cruciate ligament may be resected, and the posterior cruciate ligament (PCL) is sometimes sacrificed. As a result, knee stability is often achieved by the remaining ligamentous structures and articular surface geometry. Varus-valgus and rotational stability can be obtained by proper tensioning of collateral and capsular ligament. Information provided by the force sensor(s) of the sensor system can inform the surgeon of the amount of force provided by the ligament structure across the joint and/or the force balance between the medial and lateral sides of the joint. For example, the sensor system may include a plurality of sensors that measure the force between the medial femoral condyle and the proximal tibial plateau and the lateral femoral condyle and the proximal tibial plateau.

The joint insertion portion can be positioned to measure the force across the joint before cutting either the tibia or femur, after resecting one but not both of the tibia and femur, and/or resecting both the tibia and femur. When configured to measure the force across the joint between the opposed surfaces of the tibia and the femur after resecting both the tibia and the femur, the joint insertion portion can be configured to be inserted into the joint space without a trial and/or permanent prosthetic component attached to either the tibia or the femur, with a prosthetic component attached to one but not both of the tibia, the femur, and/or with a prosthetic component attached to both the tibia and femur.

In some implementations, the joint insertion portion of the surgical system has fixed dimensions to be inserted into the tibiofemoral joint at a specific point in the joint replacement process (e.g., after resecting both the tibia and femur but prior to installing prosthetic components, after resecting both the tibia and the femur and after installing prosthetic components on both bones). In other implementations, however, the surgical system is designed with a reconfigurable joint insertion portion. For example, the surgical system may include a sensor support body, one or more force sensors positionable on the sensor support body, and a system of covers that are positionable over and detachably coupled to the sensor support body.

When design as a reconfigurable system, the clinician can select a first cover having a first dimension and attach the first cover to the sensor support body, sandwiching the one or more force sensors between the sensor support body and the first cover. This can configure the surgical system to be used at a given point in the surgical process, e.g., prior to resecting either the tibia or the femur, after resecting one but not both bones, and/or after resecting both bones and installing a prosthetic component on one but not the other bone. The clinician can then insert the resulting assembly in the joint space to make a force measurement at this point in a surgical process. The clinician may subsequently remove the first cover and select a second cover having a second dimension and attach the second cover to the sensor support body, again interposing the one or more force sensors between the sensor support body and the second cover. In addition to making this structural adjustment to the surgical system, the clinician can advance the surgical process, resulting in a reconfiguration and dimensional change to the tibiofemoral joint space.

For example, after measuring the forces across the native joint before resecting either the tibia or the femur, the clinician may proceed to resect one or both of the bones and then insert the reconfigured surgical system with the second cover into the joint space to again measure forces across the joint in this modified configuration. As another example, after measuring the forces across the joint after resecting one but not both of the tibia and the femur, the clinician may proceed to reset the other bone and then insert the reconfigured surgical system with the second cover into the joint space (e.g., before prosthetic components) to again measured forces across the joint in this modified configuration. As yet a further example, after measuring the forces across the joint after resecting both the tibia and femur prior to installing any prosthetic components, the clinician may install a prosthetic component (e.g., trialing component) on one or both of the tibia and the femur and then insert the reconfigured surgical system with the second cover into the joint space to again measured forces across the joint in this modified configuration.

Implementing the surgical system to have a dimensionally reconfigurable joint insertion portion can be beneficial for a variety of reasons. The clinician can specifically configure the joint insertion portion of the surgical system to the requirements of the specific patient undergoing the surgical procedure (e.g., modifying the surgical system to accommodate the size and/or other characteristics of the joint of the patient being operated on). Additionally or alternatively, configuring the joint insertion portion of the surgical system to be reconfigurable can allow the clinician to collect measurable data at different points during the surgical procedure. This can provide information insights to the clinician performing the procedure, e.g., regarding forces across the tibiofemoral joint space, allowing the clinician to monitor the progress of surgical steps being performed and/or provide actionable information guiding subsequent steps of the surgical technique.

For example, the clinician may use force measurements taken across the native joint prior to resecting either the tibia or the femur to understand the native load balances across the knee. The clinician may then execute the joint replacement with a target of having the load balance across the replacement knee joint to substantially match and/or be proportional to the balancing observed across the native knee. Alternatively, the clinician may execute the joint replacement with a target of substantially symmetrically balancing forces (e.g., in the medial-to-lateral direction and/or anterior-to-posterior direction). In either case, the clinician can check and/or adjust the load balancing across the knee joint after cutting one or both of the tibia and femur before and/or after a prosthetic component is attached to one or both bones.

While the clinician may replace the one or more force sensors carried by the sensor support body with a new set of one or more force sensors each time the sensor cover is replaced, in practice, the clinician may typically reuse the same one or more force sensors between reconfigurations of the surgical system during a surgical procedure. This can be advantageous to eliminate measurement variations that may otherwise be observed between different sensors or sensor arrays. In other words, by utilizing the same one or more sensors to make force measurements at multiple points during the surgical process, the clinician may be provided with consistent, comparable data sets between force measurements that can eliminate any potential measurement or calibration discrepancies that may exist between different force sensors (e.g., were the clinician to otherwise make force measurements at different points in the surgical process using different force sensors). This can provide more consistent measurement information during the course of the surgical process, e.g., helping to drive appropriately informed surgical decision-making and surgical actions.

Although the one or more force sensors utilized in the surgical system can take a variety of different configurations, in some implementations, the surgical system includes a comparatively thin flexible circuit connecting one or more force sensors to a processing unit. The processing unit may be contained within the sensor support body or may be external from and mounted to the sensor support body. The flexible circuit can be positioned on a face of the sensor support body e.g., extending in a distal to proximal direction. One or more force sensors can be electrically and mechanically connected to the flexible circuit and positioned on a distal portion of the sensor support body. The processing unit can be positioned proximally from the one or more sensors and connected via the flexible circuit. In some examples, the aforementioned sensor cover is positioned over at least a portion of the one or more sensors and/or flexible circuit, e.g., sandwiching the covered component between the cover and sensor support body.

Depending on the design and intended use, a surgical system according to disclosure may include one or more sterilizable components that can be repeatedly used for multiple different surgical procedures and one or more disposable components that may be replaced between each surgical procedure. For example, when configured with a sensor support body, one or more sensor covers, and a processing or electronics unit, each of the three components may be sterilizable and reusable between subsequent surgical procedures. The one or more force sensors connected via the flexible circuit may be provided as a disposable component that is replaced for each procedure. Configuring the surgical system with sterilizable and reusable components operable with a disposable force sensing circuit can provide a cost-effective intraoperative assembly that can be effectively deployed within the economic constraints of joint replacement procedures demanded by insurers, providers, and patients.

Independent of the reconfigurability and reusability of the surgical system, the surgical system may include one or more features to facilitate controllable positioning of the one or more force sensors in the joint space and/or alignment of one or more prosthetic components relative to where force measurements were made in the joint space. For example, in one implementation, the surgical system includes a stop that functions to limit the depth to which the joint insertion portion of the surgical system is inserted into the joint space. For example, the stop may be formed by a projection or other enlarged region on the sensor support body and/or sensor cover (when configured with such components) that is configured to contact an anterior side of the tibia and/or femur when the joint insertion region is inserted to a desired depth in the joint space. This can facilitate consistent, reproducible positioning of the one or more force sensors carried by the surgical system, e.g., between measurements when making multiple measurements at different points in the surgical process and/or between surgical procedures and patients for providing consistent, comparable data sets for surgeon evaluation and interpretation.

As another example, the surgical system may include one or more alignment features that the surgeon can use to make one or more corresponding alignment indications on the tibia and/or femur. The one or more alignment indications can indicate where the joint insertion portion of the surgical system, and correspondingly the one or more force sensors associated therewith, were positioned in the joint space during measurement. After removing the surgical system from the joint space, the clinician can subsequently position a prosthetic component using one or more alignment indications made on the tibia and/or femur. For example, the clinician may position the tibial prosthetic component to be aligned with alignment indications made on the tibia (e.g., and thereafter affix the tibial prosthetic component to the resected tibia bone). By utilizing the one or more alignment features of the surgical system to guide subsequent alignment and positioning of one or more prosthetic components in the joint space, the clinician can help ensure that the resulting forces across the joint are consistent with the planned or target forces expected by the surgeon based on the prior force measurements made using the surgical system. This can help eliminate force discrepancies caused by positional changes between where force measurements were initially made and where one or more prosthetic components were subsequently positioned during the surgical procedure.

In addition to or in lieu of configuring the surgical system with one or more force sensors, the surgical system may include one or more position sensors operable to provide a signal indicative of the position of the sensor within three-dimensional space. For example, the surgical system may include a three-axis accelerometer providing x-, y-, and z-axes acceleration signals. In use, the position sensor may register position signals from the sensor against one or more anatomical landmarks of the patient. The position sensor can be used to make position measurements concerning the position of the tibia and/or femur in three-dimensional space. For example, a surgical system may make a position measurement indicative of the varus-valgus angle of the femur, a position measurement indicative of the varus-valgus angle of the tibia, an anterior-posterior tilt angle of the tibia, and/or anterior-posterior tilt angle of the femur. The clinician may utilize the surgical system to make one or more positional measurements associated with the joint before resecting either the tibia or the femur, after resecting one but not both of the tibia and femur, and/or after resecting both the tibia and femur.

Independent of the specific configuration of the intraoperative surgical system, the surgical system may be utilized by a surgeon during a joint replacement procedure to generate measurement information associated with forces across the joint and/or positional characteristics of the bones defining the joint not otherwise discernible to the surgeon performing the procedure. This can provide actionable information allowing the surgeon to direct subsequent steps of the surgical process and/or modify steps of the surgical process already performed to help deliver a replaced joint that is appropriately balanced and/or aligned for an efficacious clinical outcome.

In some implementations, the surgical system includes a display that displays information measured by the surgical system during the surgical procedure for surgeon visualization. The display may be integrated with a sensor support body carrying one or more sensors or may be separate from and communicatively coupled to receive measurement information generated by the one or more sensors carried by the sensor support body. For example, the display may be wirelessly connected to a processing unit carried by the sensor support body. The display can receive measurement information generated by the one or more sensors carried by the sensor support body and communicated via the processing unit to the display for display thereon. In some examples, the display receives and displays information indicative of the measurement information generated by the one or more sensors substantially in real time with the measurements being made (e.g., while the sensor support body is positioned in the joint space). This can allow the surgeon to dynamically interpret and react to the measurements being made while making the measurements.

To help guide surgeon decision-making in the surgical process supported by the intraoperative surgical system, some implementations of an intraoperative surgical system may include software executing on a computing device associated with the surgical system that is configured to receive clinician input simulating potential dimensional changes to the joint being replaced. For example, a clinician attempting to execute a knee replacement procedure to achieve a target ligament loading force(s) may initially measure one or more loaded forces across the joint and/or positional information associated with one or both bones of the joint. The clinician may interact with a user interface associated with the external device of the surgical system to input information indicating one or more dimensional changes that optionally may be made by the clinician during subsequent steps of the surgical procedure. For example, the one or more dimensional changes may indicate a thickness of bone to be resected from the tibia and/or femur and/or an angle (varus-valgus angle) at which the bone is to be resected from the tibia and/or femur. As another example, the clinician may simulate installing one or more different size prosthetic components in the joint being replaced.

In either case, the computing device may determine a projected force across the joint that will result in response to the simulated change received from the clinician, e.g., based on the force currently measured across the joint and the extent of simulated change, and display the projection for the clinician. If the projected force accords with a clinician target, the clinician may proceed with the surgical steps necessary to implement the simulated change (e.g., cutting one or more bones as simulated, selecting and installing one or more prosthetic components as simulated). If the projected force does not satisfy a clinician target, the clinician may perform one or more additional simulations proposing one or more different dimensional changes than that originally simulated. When the clinician finally arrives at a simulation set that provides a target force according with the clinician's target, the clinician may proceed to execute the surgical steps necessary to implement the simulated change. In this way, the intraoperative surgical system may provide actionable information based on current measurement information that helps guide surgical decision making and subsequent execution of the surgical technique to achieve more consistent and better clinical outcomes.

The details of one or more examples are set forth in the accompanying drawings and the description below. Other features, objects, and advantages will be apparent from the description and drawings, and from the claims.

DETAILED DESCRIPTION

This disclosure is generally directed to devices, systems, and techniques to assist a surgeon during a joint replacement procedure, such as a total knee arthroplasty. In some examples, a system is described that includes one or more sensors configured to measure force and/or position within a joint replacement procedure. For example, the system may include one or more force sensors to measure soft tissue loads across a joint during a surgical procedure. The one or more force sensors may be carried by a sensor support body positioned in the joint space to measure the force of the ligaments across the joint. This can enable the surgeon to assess the force on the ligaments and take appropriate corrective action if needed. Additionally or alternatively, the system may include one or more positional sensors to provide positional information about one or both bones defining the joint being replaced. This can provide the surgeon with information about the positional characteristics of the bone(s) and/or joint to help facilitate a more efficacious replacement. The disclosed devices, systems, and techniques can include other features and aspects, as will be described.

The devices and systems of the present disclosure can be configured to be positioned between any joint of the body formed between two bones where force and/or position information is desirably measured during a surgical procedure. For example, the devices and systems may be configured for use during any partial or total joint replacement procedure, such a procedure performed to replace a knee joint, hip joint, shoulder joint, elbow joint, wrist joint, ankle joint, finger joint, knuckle joint, or the like. In some specific applications, the disclosed devices and systems are utilized in a knee replacement surgery, which can also be referred to as a knee arthroplasty procedure. Accordingly, while the following description focuses on specific applications configured for knee arthroplasty procedures performed at the tibiofemoral joint defined between the tibia and femur, references to features and techniques described with respect to the tibia, femur, and tibiofemoral joint may be replaced by other bones and joints consistent with the disclosure.

Details on intraoperative devices, systems, and techniques for joint replacement surgery are described in greater detail with respect to FIGS. 4-27. However, to better understand a patient's knee and environment in which aspects of the described systems and techniques can be used, the anatomy of the human knee will first be described with respect to FIGS. 1A and 1B. Further, the anatomical planes of the knee will be described with respect to FIG. 2, and details on example replacement knee joint structures that can be installed during a surgical procedure utilizing devices, systems, and/or techniques of the disclosure will be described with respect to FIG. 3.

Figure 1B:
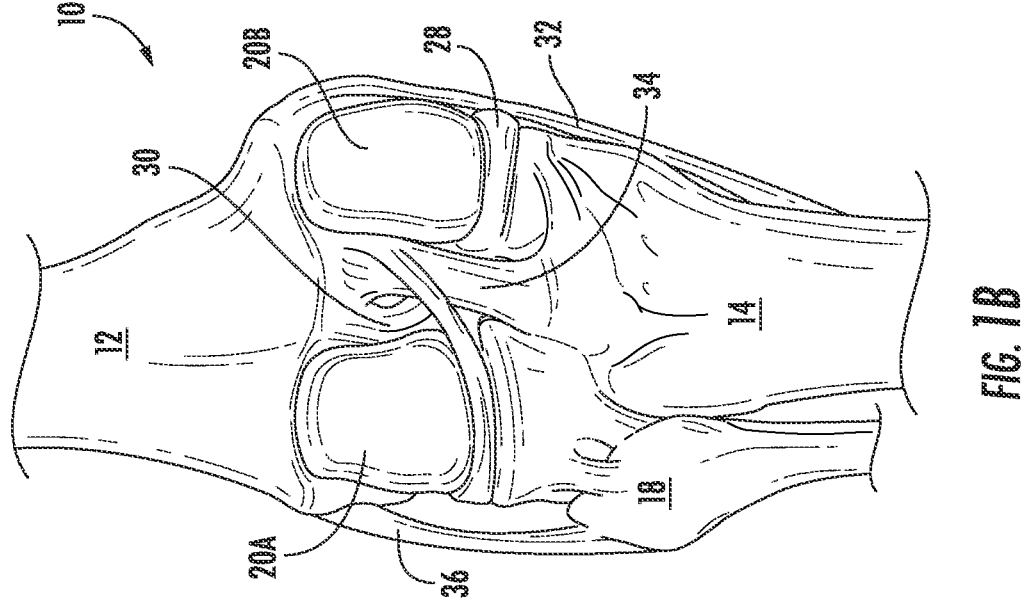
FIGS. 1A and 1B are an anterior view (with the joint capsule and patella removed) and a posterior view, respectively, of an example knee.
Figure 1A:
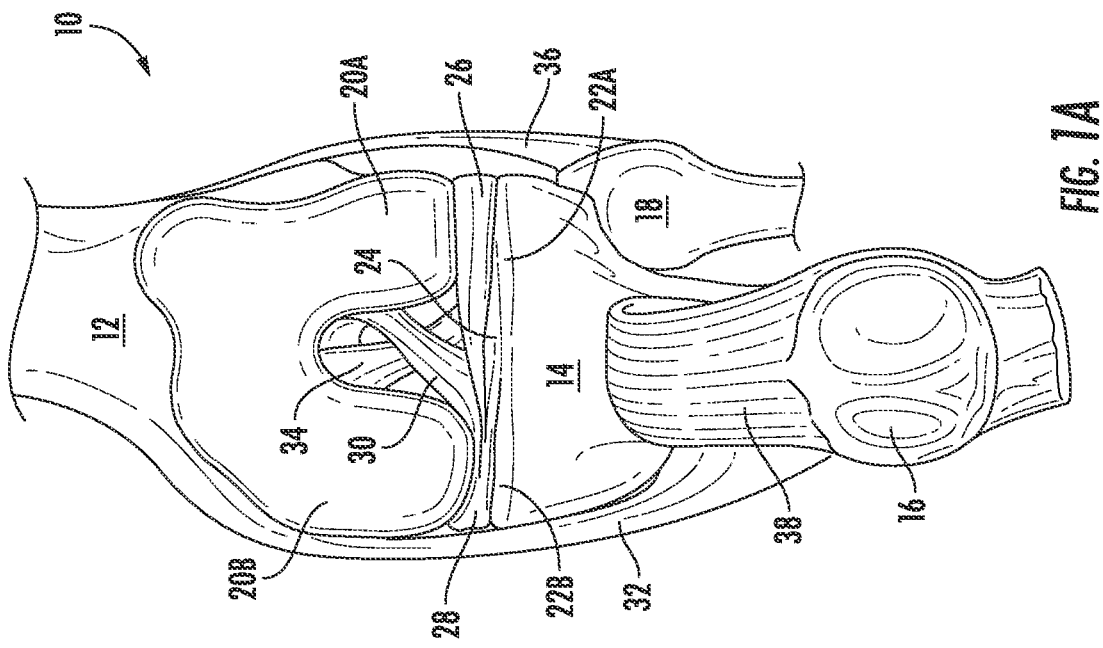

FIGS. 1A and 1B (collectively referred to as "FIG. 1") are an anterior view (with the joint capsule and patella removed) and a posterior view, respectively, of an example knee 10. Knee 10 is formed of four main structures: bones, cartilage, ligaments and tendons. Four bones fit together to make the knee: a femur 12, a tibia 14, a patella 16, and a fibula 18. The knee bones work together to support the body and transfer forces between the hip and foot, allowing the leg to move smoothly and efficiently.

The knee is a compound synovial joint incorporating two condylar joints between the condyles of the femur and tibia and one saddle joint between femur 12 and patella 16. The condylar joints are provided by the lateral femorotibial joint and the medial femorotibial joint that collectively are referred to as the tibiofemoral joint. In particular, the distal head of femur 12 terminates at a lateral condyle 20A and a medial condyle 20B. The proximal head of tibia 14 terminates in a tibial plateau that defines a lateral condyle 22A and a medial condyle 22B (also referred to as medial and lateral tibial plateaus) with an intercondylar eminence 24, or raised projection area, between the two condyles of the tibia. The femoral condyles articulate within respective tibia condyles.

Knee 10 also includes two types of cartilage: articular cartilage and meniscal cartilage. Articular cartilage is a thin layer of cartilage that lines the surface of the knee joints, including the distal end of femur 12 and proximal end of tibia 14, that decreases knee friction and helps the knee bones glide smoothly as the knee bends and straightens. A lateral meniscus 26 and a medial meniscus 28 function as shock absorbers between femur 12 and tibia 14, helping to decrease load on the articular cartilage.

Knee 10 includes ligaments that hold the bones of the knee together and provide knee stability. Ligaments illustrated in FIG. 1 include the anterior cruciate ligament (ACL) 30, the medial collateral ligament (MCL) 32, the posterior cruciate ligament (PCL) 34, the lateral collateral ligament (LCL) 36, and the patellar ligament 38. Anterior cruciate ligament 30 is a ligament that travels from the anterior of tibia 14 to the posterior of femur 12 and prevents the tibia from moving forward. Medial collateral ligament 32 is a ligament that runs between the inner surfaces of tibia 14 and femur 12 and prevents the knee from collapsing inwards. Posterior cruciate ligament 34 is a ligament that travels from the posterior of tibia 14 to the anterior of femur 12 and wraps around the ACL. It prevents tibia 14 from moving backwards on the knee. Lateral collateral ligament 36 is a ligament located on the outside of the knee on the outer surface of femur 12 and fibula 18 that resists impact from the inner surface of the knee and prevents the knee from collapsing outwards. Patellar ligament 38 connects patella 16 to the top of the tuberosity of tibia 14.

Figure 2:
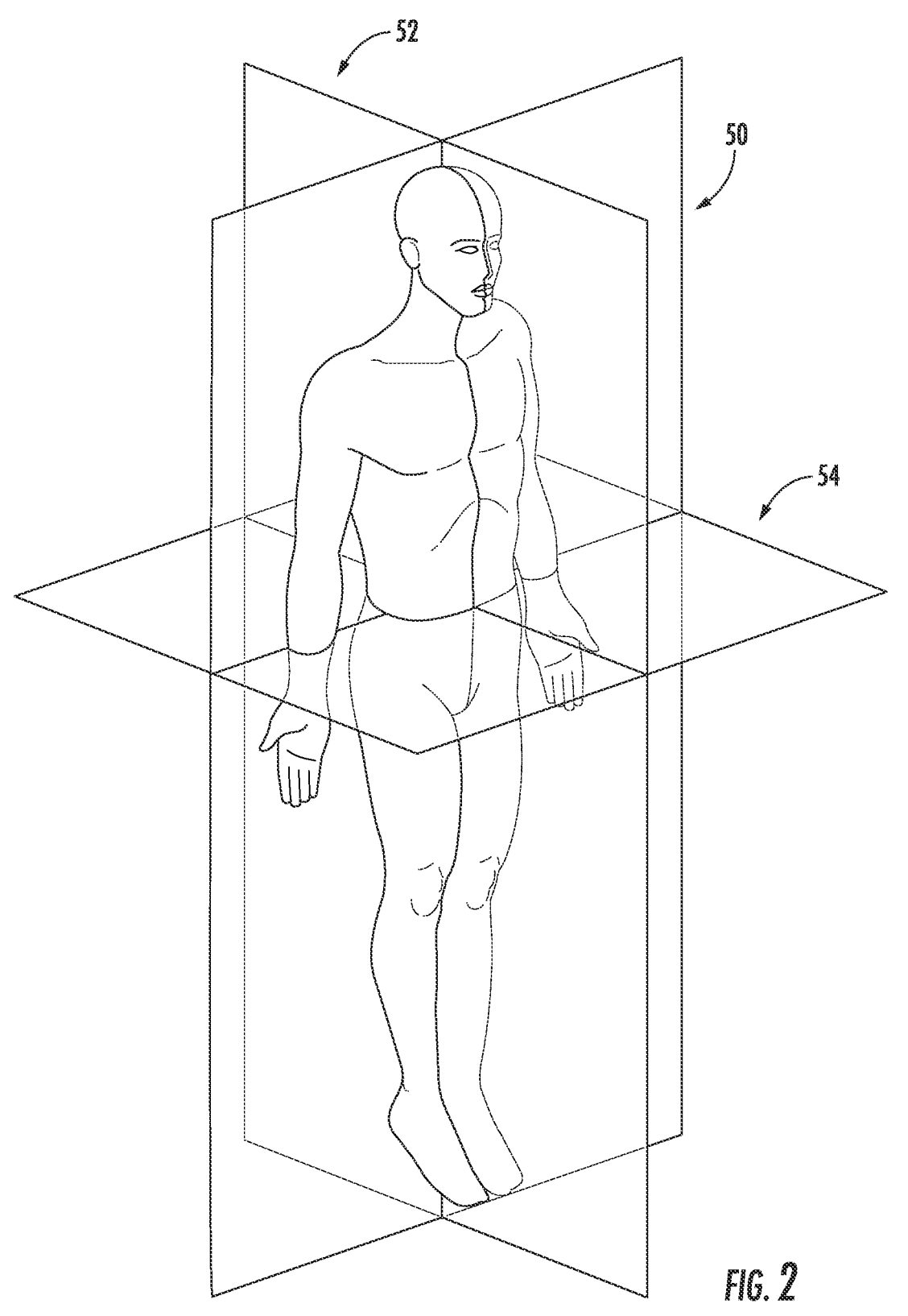
FIG. 2 illustrates the orientation of anatomic planes and relative directional terms that are used for reference in this application.

FIG. 2 illustrates the orientation of anatomic planes and relative directional terms that are used for reference in this application. The coronal plane 50, which is also referred to as the frontal plane, is a vertical plan that divides the body into anterior (toward the front of the body) and posterior (toward the back of the body) portions. The coronal plane 50 extends from a medial side (toward the midline of the body) of the knee to the lateral side (away from the midline of the body) of the knee and from the superior side (toward the top of the head) of the knee to the inferior side (toward the sole of the foot) of the knee. The sagittal plane 52 is a vertical plane running from the anterior side of the knee to the posterior side of the knee that divides the knee into medial and lateral portions thereby forming a medial compartment (that includes lateral condyle 20A of femur 12 and lateral condyle 22A of tibia 14) and a lateral compartment (that includes medial condyle 20B of femur 12 and medial condyle 22A of tibia 14). The transverse plane 54 is a horizontal plane extending anterior to posterior that divides the knee into superior and inferior portions.

Relative anatomical positions are also described as being proximal or distal, where distal is along the joint toward the ankle and proximal is along the joint toward the head. For example, the tibiofemoral joint is formed between the distal end of femur 12 comprising lateral condyle 20A and medial condyle 20B and the proximal end of tibia 14 comprising lateral condyle 22A and medial condyle 22B. Also, reference to the medial compartment of the knee can refer to the medial half of the tibiofemoral joint space between medial condyles 20B and 22B, and reference to the lateral compartment of the knee can refer to the lateral half of the tibiofemoral joint space between lateral condyles 20A and 22A. With respect to an intraoperative surgical device, relative positions along the device are also described as being proximal or distal, where distal is generally posterior and proximal is generally anterior with respect to the joint space during use of the device.

Knee replacement surgery, also known as knee arthroplasty, can be performed on knee 10 to help relieve pain and restore function lost through accident, wear, disease, and/or other condition. During the surgical procedure, femur 12 may be resected to remove diseased tissue and prepare a femoral prosthetic component to be inserted over the cut proximal end of the femur. The femoral prosthetic component may include a curved convex semi-spherical shell that covers and/or replicates the femoral condyles. Tibia 14 can be resected to form a flat, horizontal platform known as tibial plateau. A tibial prosthetic component in the form of a tibial platform can be secured to the tibial plateau, e.g., with posts or anchors fixed normal or perpendicular to the tibia plateau. A tibial insert or bearing surface can be provided between the tibia platform and the femoral prosthetic component. The femoral prosthetic component can define articular surfaces that engage concave surfaces of the top of the tibial bearing insert. The bottom of the tibial bearing insertion may be flat and engage the tibial platform.

Figure 3:
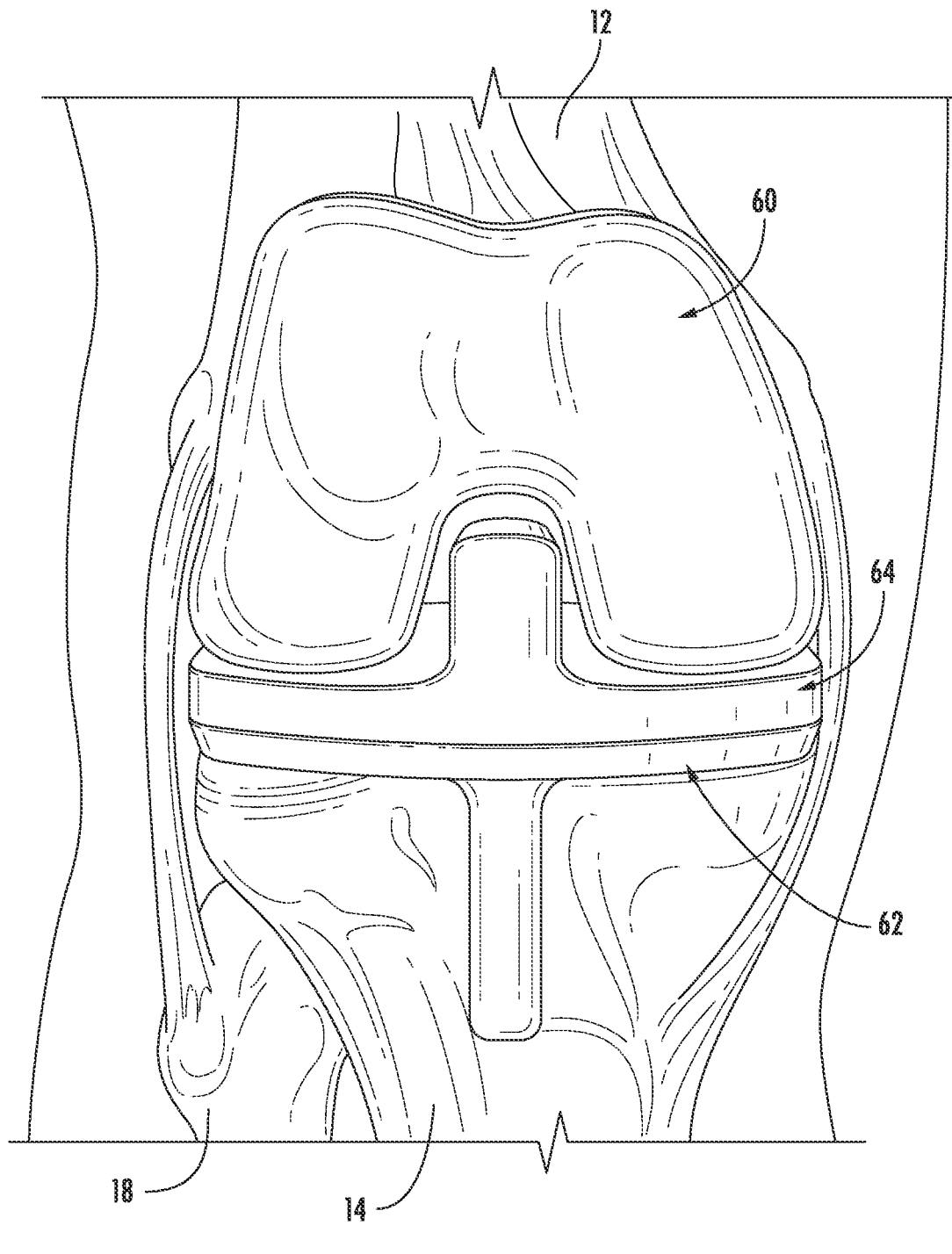
FIG. 3 is a schematic illustration of a knee illustrating an example replacement knee joint installed on the native knee.

FIG. 3 is a schematic illustration of knee 10 illustrating an example replacement knee joint installed on the native knee. In the illustrated example, the example replacement knee joint includes a femoral prosthetic component 60 affixed to femur 12, a tibial prosthetic component 62 affixed to tibia 14, and a tibial insert 64 that is illustrated as being positioned between femoral prosthetic component 60 and tibial prosthetic component 62. Tibial insert 64 can be a fixed-bearing that is non-moveably affixed to tibial prosthetic component 62 or a mobile-bearing that provides a rotating platform relative to the tibial prosthetic component. The replacement knee joint may be a posterior-stabilized design (e.g., in which the cruciate ligaments are removed and parts of the implant substitute for the posterior cruciate ligament) or a cruciate-retaining design (e.g., in which the PCL is preserved with the implant design). Moreover, while the ACL may typically be removed to allow for precise placement of the implant, the implant may be configured as a bicruciate-retaining design in which both the ACL and PCL are preserved. Further, while FIG. 3 illustrates an example replacement knee joint for a total knee replacement, the replacement knee may be a partial or unicompartmental implant in which just one compartment (medial compartment or lateral compartment) of the knee is replaced. The intraoperative devices, systems, and techniques of the present disclosure can be used with any of the foregoing types of replacement knee joint configurations.

Each prosthetic component can be affixed to bone using cemented fixation (e.g., fast curing bone cement such as polymethylmethacrylate), cementless fixation (e.g., press-fit onto bone and relying on new bone growing into the surface of the implant), or hybrid fixation (e.g., a combination of cemented and cementless fixation is used). All the components of the replacement knee joint can be made of biocompatible materials, with femoral prosthetic component 60 and tibial prosthetic component 62 typically fabricated from metal (e.g., titanium- or cobalt-chromium-based alloys) and/or ceramic materials (e.g., ceramics or ceramic/metal mixtures such as oxidized zirconium) and tibial insert 64 typically made of a polymeric material (e.g., ultrahigh molecular weight polyethylene).

During a knee replacement procedure, the surgeon will typically cut ACL 30 (FIG. 1) to provide access to the tibiofemoral joint space and resect both femur 12 and tibia 14 to prepare the bones to receive corresponding prosthetic components. The surgeon may next install trial prosthetic components on the bones. Trialing can help the surgeon assess the knee for adequate balancing, range of motion, and stability. During trialing, one or more temporary inserts can be utilized in conjunction with trial and/or definitive femoral and tibial prosthetic components. Trial components can help the surgeon judge flexion and extension gaps, soft tissue balancing, and motion of the knee, with a variety of thicknesses available. Once inserted, the surgeon can cycle the knee through its range of motion, with varus/valgus stresses applied. If the temporary insert creates a balanced knee with an appropriate range of motion, the surgeon can select a definitive implant (e.g., definitive tibia and/or moral prosthetic component and/or definitive tibial insert) having the same thickness and size as the trial. The surgeon can securely affix to the selected definitive insert to the definitive tibial prosthetic component.

Traditionally, the assessment of knee balance, range of motion, and stability during the joint replacement procedure has been a relatively subjective process that may result in differential decisions and outcomes surgeon to surgeon and patient to patient. Further, assessment of knee balance, range of motion, and stability during the joint replacement procedure has traditionally been limited to the trialing phase after femur 12 and tibia 14 are fully resected. At this point in the surgical procedure, the surgeon may have limited options available for correcting apparent knee balance concerns impacting range of motion and/or stability. For example, the surgeon may select a different size tibial insert to adjust the spacing between the tibial and femoral prosthetic components. Additionally or alternatively, the clinician may perform a ligament release by cutting a desired number of ligament fibers on one or both sides of the knee to adjust balance. In each case, the surgeon may be seeking to a control and balance forces across the knee provided by the soft connective tissue, including medial collateral ligament 32 and lateral collateral ligament 36.

Some implementations of the present disclosure provide an intraoperative system that can be used to assess aspects of the knee joint being replaced and provide objective information indicative of knee balance and/or position. This information can allow the clinician to objectively evaluate the surgical procedure being performed on the knee joint and adjust one or more aspects of the surgical procedure and/or replacement knee joint in response to the information provided by the intraoperative system. This can lead to more consistent clinical outcomes surgeon to surgeon and patient to patient across a wide variety of patient anatomies and joint conditions.

In various implementations, the intraoperative surgical system can be used before cutting both femur 12 and tibia 14, after cutting one but not both bones, after cutting both bones but prior to installing the one or both prosthetic components, and/or after installing one or both prosthetic components. For example, the intraoperative surgical system may be modularly reconfigurable to be inserted into the tibiofemoral joint at different points in the surgical procedure. Rather than merely assessing soft tissue forces and/or positional information at one point in the surgical process, such as during trialing and installation of the prosthetic components, systems and techniques of the disclosure may be utilized at multiple points in the process. When so configured, the clinician may adjust subsequent surgical steps to react to the objective information provided by the intraoperative surgical system. An intraoperative surgical system according disclosure can have a variety of different features, elements, and functionalities as discussed in greater detail below.

Figure 4:
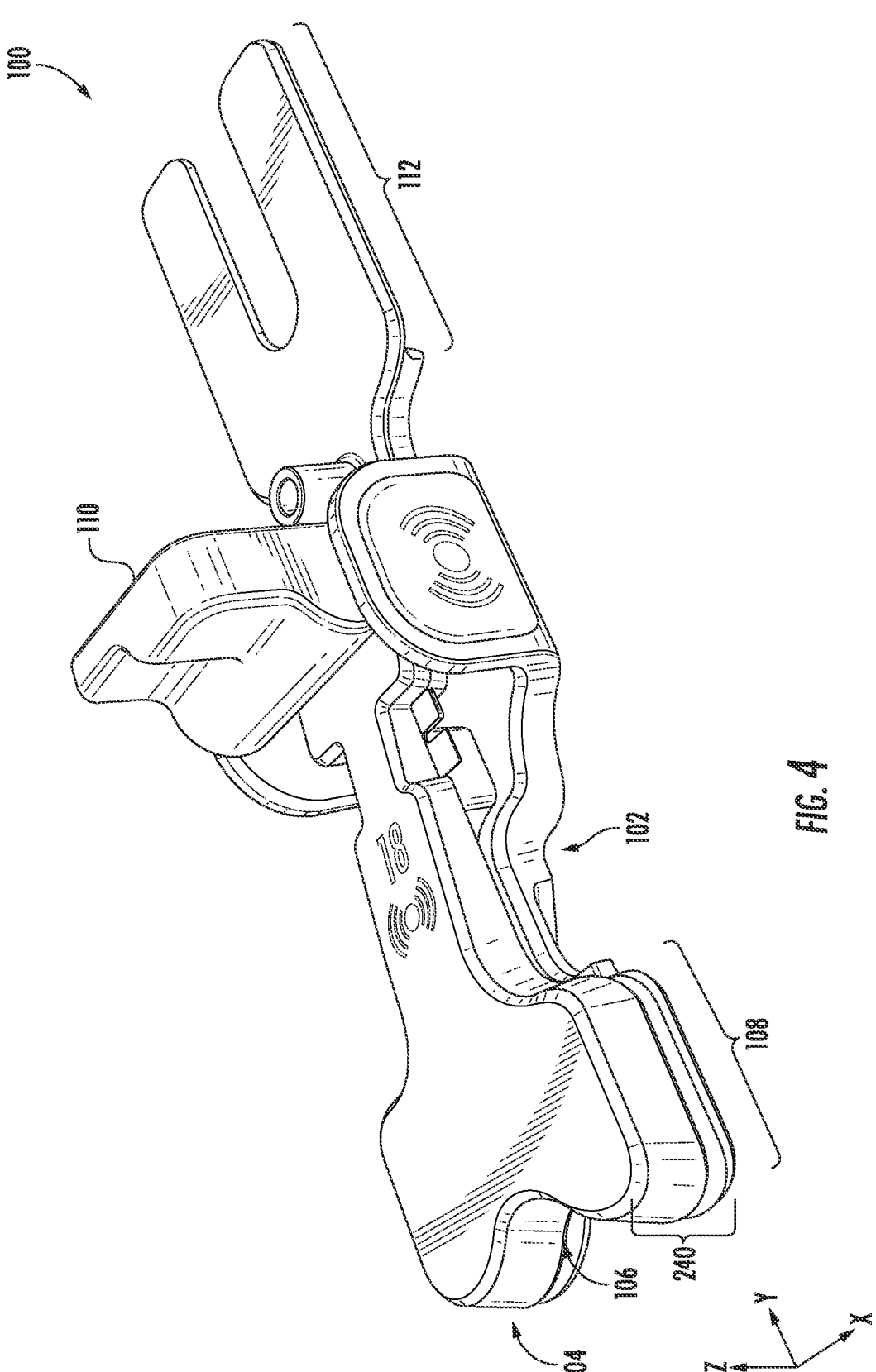
FIG. 4 is a perspective view of an example configuration of an intraoperative surgical system that can be used during a joint replacement procedure, such as a knee arthroplasty procedure.

FIG. 4 is a perspective view of an example configuration of an intraoperative surgical system 100 that can be used during a joint replacement procedure, such as a knee arthroplasty procedure. System 100 is illustrated as including a sensor support body 102, a sensor cover 104, and at least one force sensor 106. Sensor support body 102 can carry force sensor 106 for insertion into the tibiofemoral joint space. For example, force sensor 106 can be interposed between sensor support body 102 and sensor cover 104 to define a joint insertion portion 108 insertable into the tibiofemoral joint space.

Upon being inserted into the joint space, femur 12 can press against sensor cover 104 (e.g., directly or through a prosthetic component) and tibia 14 can press against sensor support body 102 (e.g., directly or through a prosthetic component). The forces generated across the tibiofemoral joint between femur 12 and tibia 14 for measurement can be provided by the soft tissue structure of the knee, including the medial and collateral ligaments 32, 36. Force sensor 106 can measure the force across the joint space, providing balancing information that can be communicated to the surgeon. The force measured across the tibiofemoral joint can indicate the tightness or laxity of the soft tissue across the joint, including the medial and collateral ligaments 32, 36, and may indicate medial-lateral and/or anterior-posterior balancing of forces. The surgeon may make surgical and/or implant adjustments in response to the measure information, helping to improve the effectiveness and patient satisfaction of the replacement joint.

System 100 in FIG. 4 it is also illustrated as including an electronics housing 110 positioned proximally of joint insertion portion 108. Force sensor 106 can be electrically connected to electronics module 110. Electronics housing 110 may contain various components for powering and controlling system 100, such as a power source, processor, and memory. In some configurations, electronics module 110 may be provided as a cavity or void space within sensor support body 102 into which the electronic components are installed. The cavity or void space may be enclosed with a cover or sealing material to enclose the electronic components in the space within sensor support body 102. In other configurations, electronic housing 110 may be formed by part of sensor cover 104. In yet other configurations, such as that illustrated in FIG. 4, electronics housing 110 may be detachable from and attachable to sensor support body 102. When so configured, electronics housing 110 may be a modular, self-contained unit carrying various electronic components of system 100.

Force sensor 106 can be electrically and/or mechanically connected to components contained in electronics housing 110. For example, force sensor 106 can be powered via a power source contained in electronics housing 110, and a processor contained in the electronics housing can communicate with and receive signals from the force sensor. During assembly, electronics housing 110 can be attached to sensor support body 102 and force sensor 106 electrically coupled to the components in the electronics housing. Configuring system 100 with a detachable electronics housing 110 may be beneficial, e.g., to allow the electronics housing to move to adjust a positional orientation where the force sensor connects to the housing. Additionally, configuring system 100 with a detachable electronics housing can allow the electronics housing to be removed for cleaning, replacement, and/or adjusting the positional orientation of the housing.

Electronics housing 110 can be positioned at any suitable location along sensor support body 102 (or may be integrated into the sensor support body and/or sensor cover, as discussed above). In some configurations, electronics housing 110 is positioned at a location along the length of sensor support body 102 (extending in the Y-direction indicated on FIG. 4) proximally offset from joint insertion portion 108. This can allow joint insertion portion 108 to be inserted into the tibiofemoral joint space while electronics housing 110 remains outside of and offset from the joint space.

In general, system 100, including sensor support body 102, may include at least one portion configured to be positioned in the tibiofemoral joint space and at least one adjacent portion configured to extend outwardly away from the tibiofemoral joint space. For example, FIG. 4 illustrates system 100 as including joint insertion portion 108 configured to position the tibiofemoral joint space and an adjacent region to which electronics housing 110 is attached configured to extend outwardly away from the joint space. This can provide a region manipulable by a clinician to insert joint insertion portion 108 into the joint space, to control positioning of the joint insertion portion while in the joint space, and/or to withdraw the joint insertion portion from the joint space.

In some configurations, system 100, including sensor support body 102, has a length defining joint insertion portion 108 on one side and a handle or gripping portion on the opposite side of the length. In other configurations, system 100, including sensor support body 102, has two different joint insertion portions on opposite sides of the sensor support body. For example, sensor support body 102 may include a first joint insertion portion 108 on a first side of the sensor support body and a second joint insertion portion 112 on a second side of the sensor support body. First joint insertion portion 108 can be separated or spaced from second joint insertion portion 112 along the length of sensor support body 102.

Configuring sensor support body 102 with multiple different joint insertion portions can be beneficial to provide different sizing options to be inserted into the joint. For example, first joint insertion portion 108 may have a first thickness (in the Z-direction indicated on FIG. 4) and second joint insertion portion 112 may have a second thickness different than the first thickness. The thickness of the first joint insertion portion 108 may be thicker than the thickness of second joint insertion portion 112. As will be discussed, the thicknesses may be further controlled or adjusted by controlling the sizing of sensor cover 104.

In either case, however, first joint insertion portion 108 may be sized to be positioned in the tibiofemoral joint after at least one the bones defining the joint has been cut (e.g., with or without a prosthetic component installed). By contrast, second joint insertion portion 112 may be sized to be positioned in the native tibiofemoral joint before cutting either of the bones defining the joint (before resecting either femur 12 or tibia 14). Because of the comparatively small size of the tibiofemoral joint prior to resecting femur 12 and tibia 14 (small spacing between the distal end of the femur and the proximal head of the tibia), second joint insertion portion 112 may be a comparatively thinner region that can be inserted into this small space. In addition, in some implementations, the comparative thinness of second joint insertion portion 112 may allow the joint insertion portion to flex or bend (e.g., in the Z-direction indicated on FIG. 4), providing flexibility to help the clinician insert the joint insertion portion into the native knee joint. First joint insertion portion 108 may be a comparatively thicker region that can be inserted into the tibiofemoral joint a larger tibiofemoral joint space (e.g., when the spacing between the distal end of the femur and proximal head of the tibia is larger than the spacing observed for the native joint).

While first joint insertion portion 108 and second joint insertion portion 112 can be configured with different thickness dimensions, the two joint insertion portions may have other size and/or shape differences in addition to or in lieu of exhibiting a thickness variation. For example, the two joint insertion portions may have a same or different width from each other (e.g., in the X-direction indicated on FIG. 4) and/or a same or different length from each other (e.g., in the Y-direction indicated on FIG. 4). Additional example size and shape details for first joint insertion portion 108 and second joint insertion portion 112 will be discussed below.

Figure 5A:
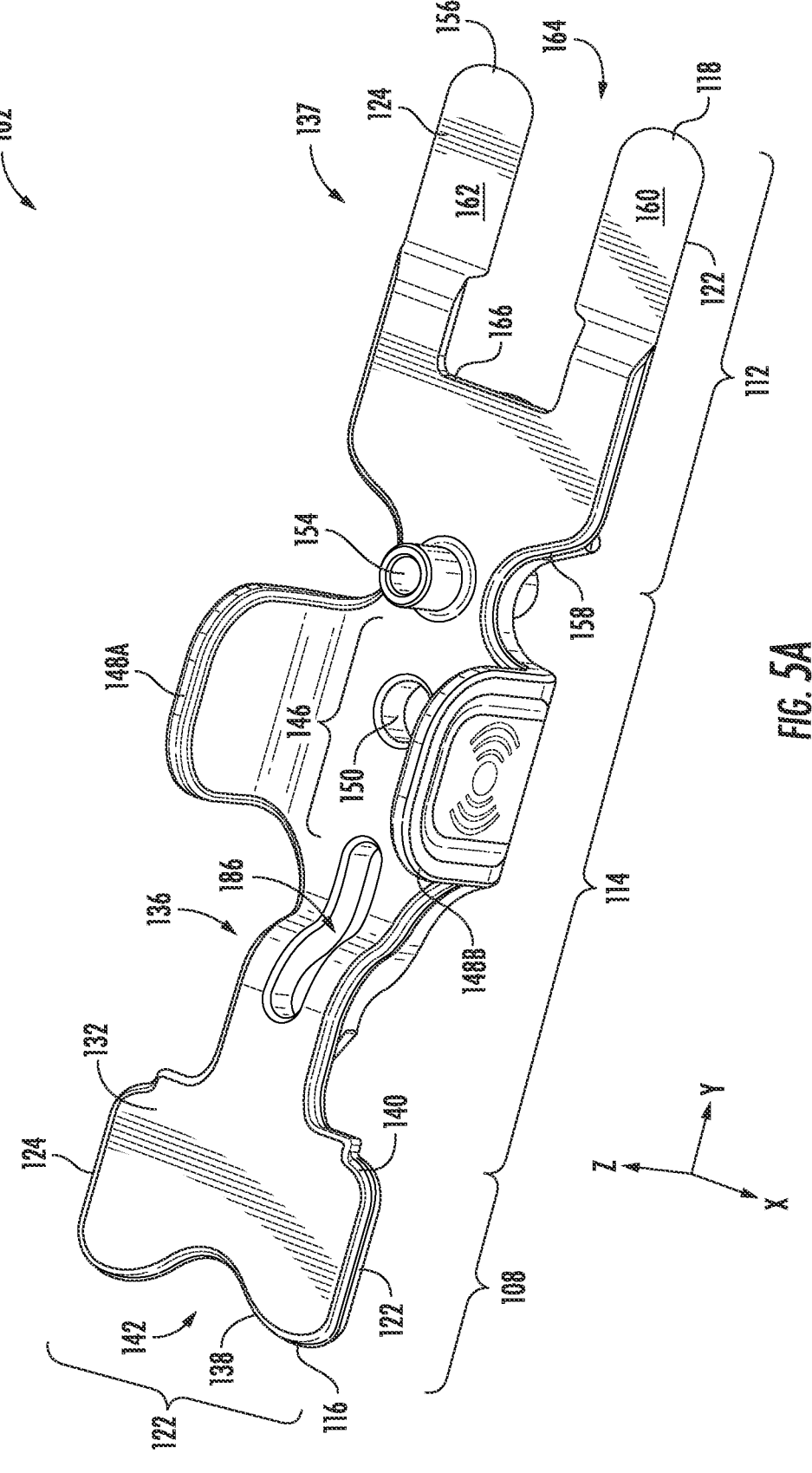
FIGS. 5A-5D are different views of an example configuration of a sensor support body.
Figure 5B:
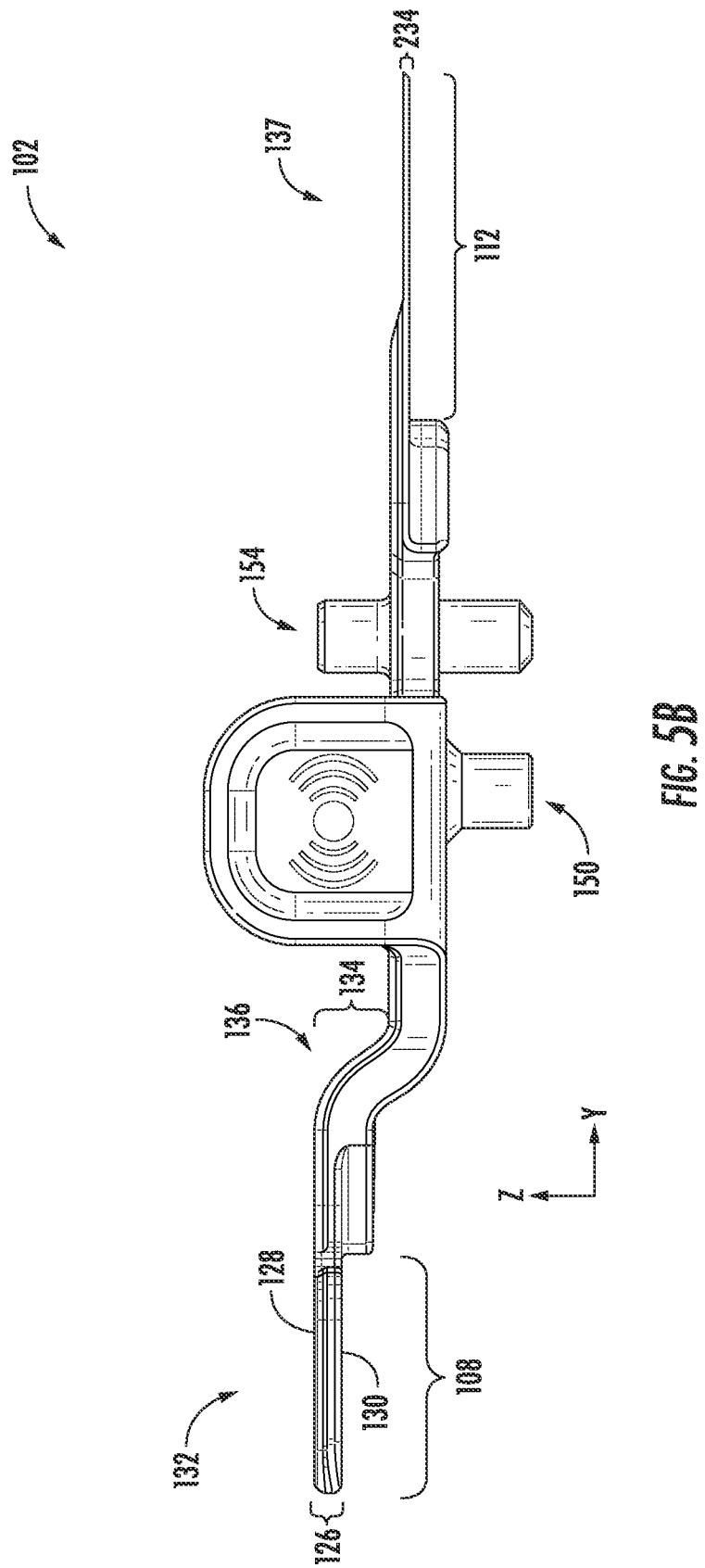
Figure 5C:
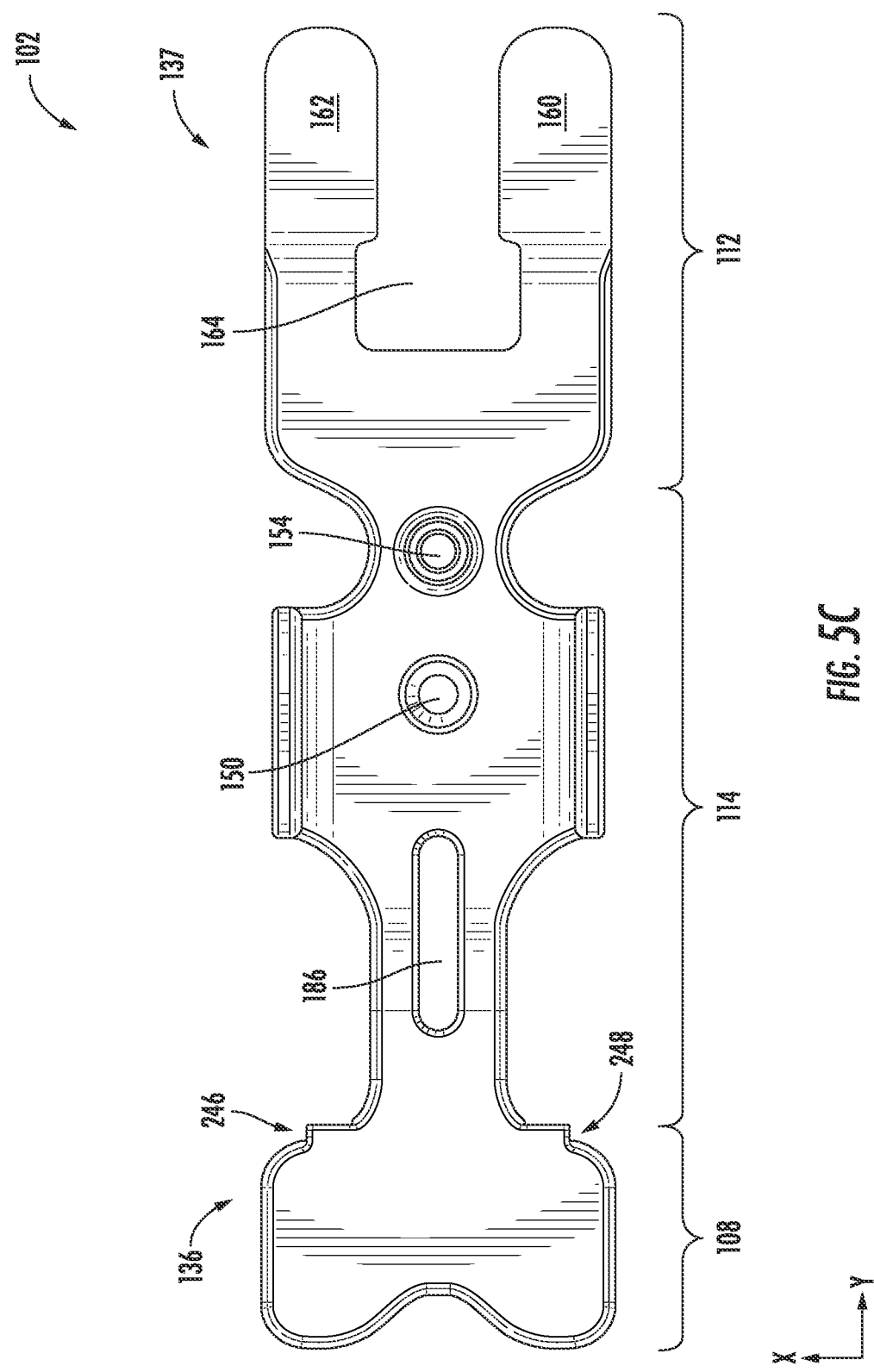
Figure 5D:
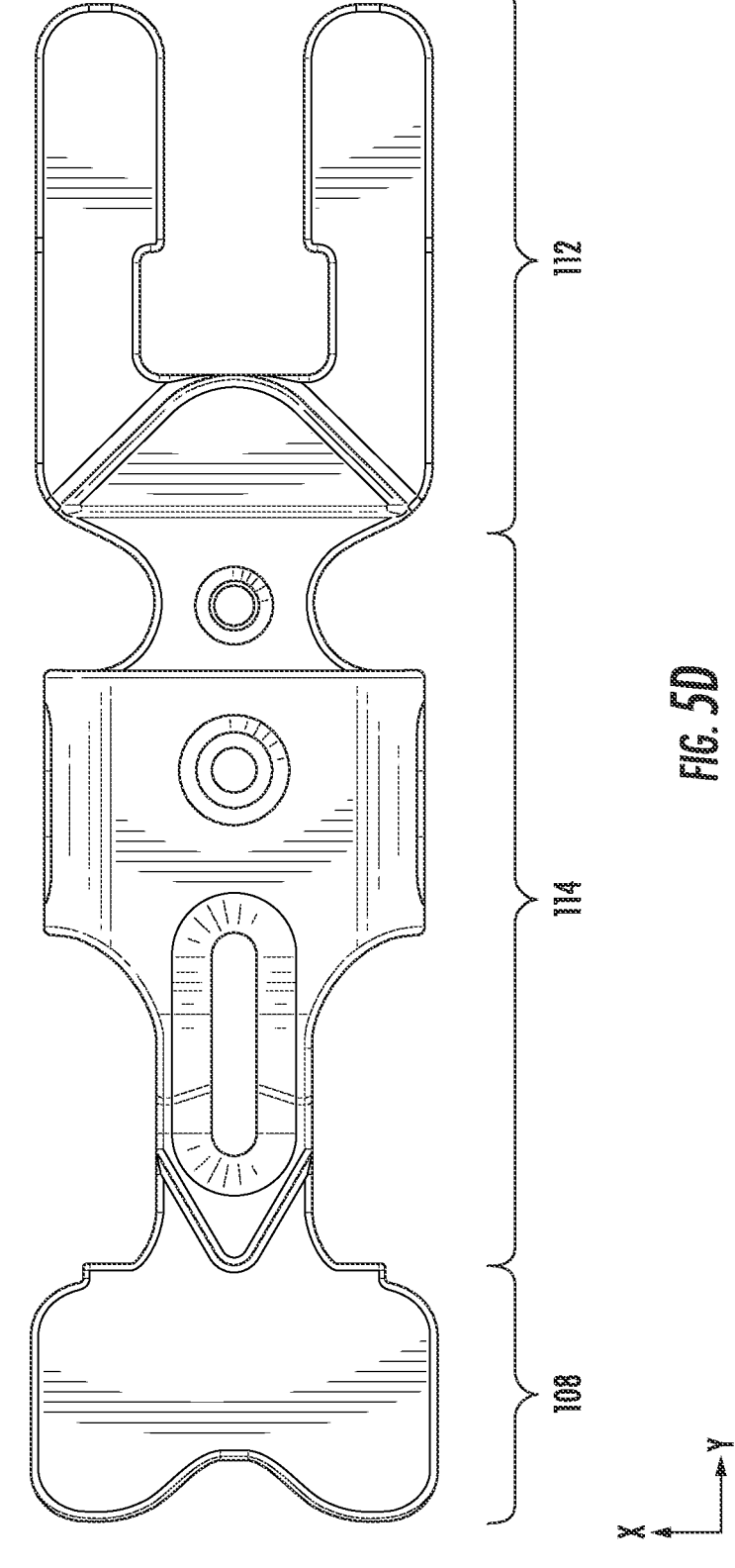

FIGS. 5A-5D (collectively referred to as "FIG. 5") are different views of an example configuration of sensor support body 102 shown with sensor cover 104, force sensor 106, and electronics housing 110 removed for purposes of illustration. FIG. 5A is a perspective view of the sensor support body. FIG. 5B is a side view of the sensor support body. FIG. 5C is a top view of the sensor support body. FIG. 5D is a bottom of the sensor support body.

As illustrated in the example of FIG. 5, sensor support body 102 can define a length 114 extending from a first end 116 to a second end 118. Sensor support body 102 can also define a width 120 extending from a first side 122 to a second side 124. Sensor support body can also define a thickness 126 (e.g., FIG. 5B) extending from a first side 128 to a second side 130. A first joint insertion portion 108 is on a first side of sensor support body 102 terminating in the first end 116 of the sensor support body. Second joint insertion portion 112 is on a second side of sensor support body 102 terminating in the second end 118 of the sensor support body.

As discussed with respect to FIG. 4, sensor support body 102 can carry one or more sensors, such as one or more force sensors 106 for measuring a load force across the tibiofemoral joint. The one or more force sensors 106 may be integrated into an electrical circuit that can be positioned between sensor support body 102 and a sensor cover 104. A compression force applied between the outer surfaces of sensor support body 102 and the outer surface of sensor cover 104 can translate through to the force sensors for measurement by the sensor.

To facilitate positioning of force sensors 106 on sensor support body 102, the sensor support body may define one or more substantially planar surfaces against which the one or more force sensors can be positioned. Sensor cover 104 can have corresponding substantially planar surfaces, allowing the one or more force sensors 106 to be sandwiched between substantially planar surfaces. Positioning the one or more force sensors between planar surfaces can help ensure that forces are translated substantially uniformly through sensor support body 102 and sensor cover 104 to the underlying force sensor, e.g., helping to avoid measurement distortion caused by uneven force transfer.

To provide a region where one or more force sensors 106 can be positioned on sensor support body 102, the sensor support body may define a platform 132. Platform 132 may be a region of sensor support body 102 within the region defined by joint insertion portion 108 that is configured (e.g., sized and/or shaped) to receive one or more force sensors 106 positioned thereon. The first side 128 of platform 132 on which the one or more force sensors 106 are intended to be positioned may be planar or flat (e.g., in the X-Y plane). Platform 132 may be raised relative to an adjacent region of sensor support body or may be coplanar with (or even recessed relative to) the remainder of the sensor support body. In either case, platform 132 can provide a foundation for receiving the one or more force sensors thereon.

In the example of FIG. 5, platform 132 is illustrated as being axially offset from a proximal portion of sensor support body 102. In particular, in the illustrated configuration, platform 132 is offset from adjacent region of sensor support body 102 that is positioned outside of the tibiofemoral joint (when joint insertion portion 108 is inserted into the joint). This includes the region of sensor support body 102 to which electronics housing 110 detachably couples.

For example, with reference to FIG. 5B, first surface 128 of platform 132 of sensor support body 102 is axially offset a distance 134 from the first surface 128 of the adjacent region of the sensor support body. In this illustrated implementation, sensor support body 102 defines at least two planar regions in different planes that are axially offset from each other. For example, sensor support body 102 includes a first planar region comprising platform 132 in a first plane (X-Y plane) and a second planar region proximal to the first planar region (e.g., encompassing second joint insertion portion 112 and an intermediate region between the first and second joint insertion portions) in a second plane (X-Y plane) offset in the Z-direction. In other configurations, the second joint insertion region 112 may be coplanar with first joint insertion region 108 or may be in yet a different plane (e.g., a third plane) then the first joint insertion region and an intermediate region between the first and second joint insertion regions.

Positioning platform 132 at a different elevation than an adjacent region of sensor support body 102 may be useful to facilitate positioning the one or more force sensors 106 on the platform and connecting the one or more force sensors back to electronics housing 110 positioned proximally of the force sensors. For example, first surface 128 of platform 132 may be positioned substantially coplanar (in the X-Y plane) with a portion of electronics housing 110 to which the one or more force sensors 106 are configured to electrically connect. An electrical circuit containing the one or more force sensors 106 can extend from platform 132 (on which the one or more force sensors are positioned) proximally to the electronics housing 110 and be connected thereto. By offsetting platform 132, the electrical circuit may extend planarly to connect to electronics housing 110, e.g., without bending or bowing out of plane in the Z-direction to engage a connector of electronics housing 110 at a different elevation. This may help limit unintended shifting of the one or more force sensors 106 on platform 132 and/or distortion of the force measurement made by the one or more sensors. That being said, in other configurations, platform 132 may be coplanar with a proximately adjacent region of sensor support body 102 (e.g., with or without the circuit connecting the one or more force sensors 106 changing elevation to connect to electronics housing 110).

As illustrated, sensor support body 102 includes a first planar region comprising platform 132 in a first plane, a second planar region proximal to the first planar region, and a bridge 136 between the first and second planar regions. Bridge 136 may provide an elevational transition between the different planar regions of sensor support body 102. Bridge 136 may provide a sloped transition from one elevation region of sensor support body 102 to a second elevation region of the sensor support body. In other configurations, the sensor support body may include a step off (e.g., 90° transition between elevation regions). In some implementations, the distance 134 that first surface 128 of platform 132 is offset from the first surface 128 of the adjacent region of the sensor support body is at least 5 mm, such as at least 10 mm, at least 12 mm, at least 14 mm, at least 16 mm, at least 18 mm, or at least 20 mm. For example, distance 134 may range from 5 mm to 50 mm, such as from 10 mm to 25 mm, or from 15 mm to 20 mm.

Depending on the number of joint insertion portions defined by sensor support body 102, the sensor support body may define a single platform 132 or multiple platforms associated with each of the different joint insertion portions. For example, sensor support body 102 may define a first platform 132 within the region defined by first joint insertion portion 108 and a second platform 137 within the region defined by second joint insertion portion 112. The one or more force sensors 106 can be selectively positioned on either of or both of the platforms defined within the first joint insertion portion 108 and the second joint insertion portion 112.

For example, during a surgical procedure, a clinician may initially position one or more force sensors 106 on the second platform 137 defined by second joint insertion portion 112. The clinician may insert a sensor cover over the one or more force sensors to sandwich the force sensors between the platform and sensor cover. The clinician may then insert the second joint insertion portion 112 into the native knee joint (e.g., prior to resecting femur 12 and tibia 14) to measure loads across the native knee joint. The clinician may then reposition the one or more force sensors from second platform 137 to first platform 132 defined by first joint insertion portion 108. The clinician may insert a sensor cover over the one or more force sensors to sandwich the force sensors between the first platform 132 and the sensor cover. After resecting one or both of femur 12 and tibia 14, the clinician can insert first joint insertion portion 108 into the resected tibiofemoral joint to measure loads across the prepared knee joint.

In the illustrated example, first joint insertion portion 108 is illustrated as a contiguous plate of material having of leading edge 138 and a trailing edge 140. During use, leading edge 138 of first joint insertion portion 108 is advanced into the tibiofemoral joint space before trailing edge 140 (with trailing edge 140 optionally positioned in or out of the tibiofemoral joint space). First joint insertion portion 108 also defines a width between first side edge 122 and second side edge 124. As illustrated, first joint insertion portion 108 defines a generally rectangular shape although may have other polygonal (e.g., square, triangular) and/or arcuate shapes.

Further, in the illustrated arrangement, leading edge 138 of first joint insertion portion 108 does not extend linearly across the entire width of the joint insertion portion but rather defines a cutout 142. Cutout 142 may be a recessed region extending proximally along the length of sensor support body 102 and substantially centered across the width of joint insertion portion 108. Cutout 142 may be configured (e.g., sized, shaped, positioned) to provide a void space for accommodating posterior cruciate ligament 34 of the tibiofemoral joint, when first joint insertion portion 108 is fully seated into the joint space. The sides of first joint insertion portion 108 may extend distally beyond cutout 142, allowing the sides of the joint insertion portion to wrap partially around anatomical structure (e.g., posterior cruciate ligament 34) positioned in cutout 142, when first joint insertion portion 108 is inserted into the tibiofemoral joint space.

While the dimensions of first joint insertion portion 108 may vary, in some implementations, the first joint insertion portion has a maximum length from leading edge 138 to trailing edge 140 ranging from 25 mm to 200 mm, such as from 50 mm to 100 mm, or from 60 mm to 80 mm. First joint insertion portion 108 may have a maximum width from first side edge 122 to second side edge 124 ranging from 20 mm to 100 mm, such as from 30 mm to 70 mm, or from 50 mm to 60 mm. The maximum length of first joint insertion portion 108 may be larger than the maximum width of the joint insertion portion.

Second joint insertion portion 112 is positioned on an opposite lengthwise side of sensor support body 102 from first joint insertion portion 108. An intermediate region 144 of sensor support body 102 is located between first joint insertion region 108 and second joint insertion region 112. Intermediate region 144 may have a length greater than the length of first joint insertion region 108 and/or second joint insertion region 112. Intermediate region 144 may also have a width that is the same as or different than a maximum width of first joint insertion region 108 and/or second joint insertion region 112.

As illustrated, intermediate region 144 includes an electronics receiving area 146 where electronics housing 110 can be positioned. Electronics housing receiving area 146 in the illustrated configuration is defined by a substantially planar top surface of sensor support body 102 between first joint insertion portion 108 and second joint insertion portion 112. Electronics housing receiving area 146 may be bounded widthwise by opposed sidewalls 148A, 148B extending upwardly (in the Z-direction) away from the top surface (in the X-Y plane) indicated on FIG. 5. For example, sidewalls 148A, 148B may extend generally orthogonally from the top surface of sensor support body 102 to a height effective to partially or fully enclose the sidewalls of electronics housing 110. In some implementations, sidewalls 148A, 148B extend above first surface 128 of sensor support body 102 a distance ranging from 5 mm to 100 mm, such as from 10 mm to 75 mm, or from 20 mm to 55 mm.

The distance between the inside surfaces of opposite sidewalls 148A, 148B may be greater than or substantially equal to the width of electronics housing 110, allowing electronics housing to be positioned between the sidewalls (e.g., with the sides of the electronics housing optionally contacting the inside surfaces of the sidewalls 148A, 148B). Configuring sensor support body 102 with sidewalls 148A, 148B may be useful to help secure electronics housing 110 to the sensor support body. The sidewalls may limit relative movement of electronics housing 110 after being attached to sensor support body 102 and/or prevent inadvertent detachment of the electronics housing by the clinician grasping system 100.

Electronics housing 110 can be permanently attached to and/or integrated with sensor support body 102. Alternatively, electronics housing 110 can be detachably attached to sensor support body 102. In general, sensor support body 102 and electronics housing 110 can have any suitable features to facilitate detachably connecting the electronics housing to the sensor support body. For example, sensor support body 102 can have a connector and electronics housing 110 a complementary connector that allows the electronics housing to detachably connect to the sensor support body. For example, one of sensor support body 102 and electronics housing 110 may have a female connector and the other of the components may have a male connector that is insertable into the female connector to interconnect the electronics housing with the sensor support body. Electronics housing 110 can be attached to sensor support body 102 using the connector system and retained on the sensor support body during use. After use, the electronics housing 110 can be disengaged or detached from sensor support body 102.

In some implementations, the connector system that allows electronics housing 110 to be connected to sensor support body 102 restricts the electronics housing to be positioned in a single orientation. For example, the connector system may fix the position of orientation of electronics housing 110 relative to sensor support body 102 in a single position. In other implementations, the connector system may allow electronics housing 110 to be connected to sensor support body 102 in multiple different orientations. For example, the connector system may allow electronics housing to be positioned in a first positional orientation relative to sensor support body 102 and then reoriented to a second positional orientation different than the first positional orientation.

In some examples, the connector system is configured to allow electronics housing 110 to be attached to sensor support body 102 in a first positional orientation in which an electrical connector carried by the electronics housing faces first joint insertion portion 108 and also allow the electronics housing to be attached in a second positional orientation in which the electrical connector carried by the electronics housing faces second joint insertion portion 112. For example, the connector system may allow electronics housing 110 to be flipped or rotated 180° relative to sensor support body 102. Allowing electronics housing 110 to be detachably connected to sensor support body 102 in different positional orientations can be useful for repositioning the one or more force sensors 106 between first joint insertion portion 108 and second joint insertion portion 112. Electronics housing 110 can be attached to sensor support body 102 in different orientations depending on whether the electronics housing is to be connected to force sensors 106 on a first joint insertion portion 108 or to force sensors on second joint insertion portion 112.

In the example of the FIG. 5, electronics receiving area 146 of sensor support body 102 defines a female connector 150 that is configured to receive a corresponding male connector extending from electronics housing 110. Female connector 150 is illustrated as an aperture extending through the thickness of sensor support body 102 in electronics receiving area 146.

Figure 6:
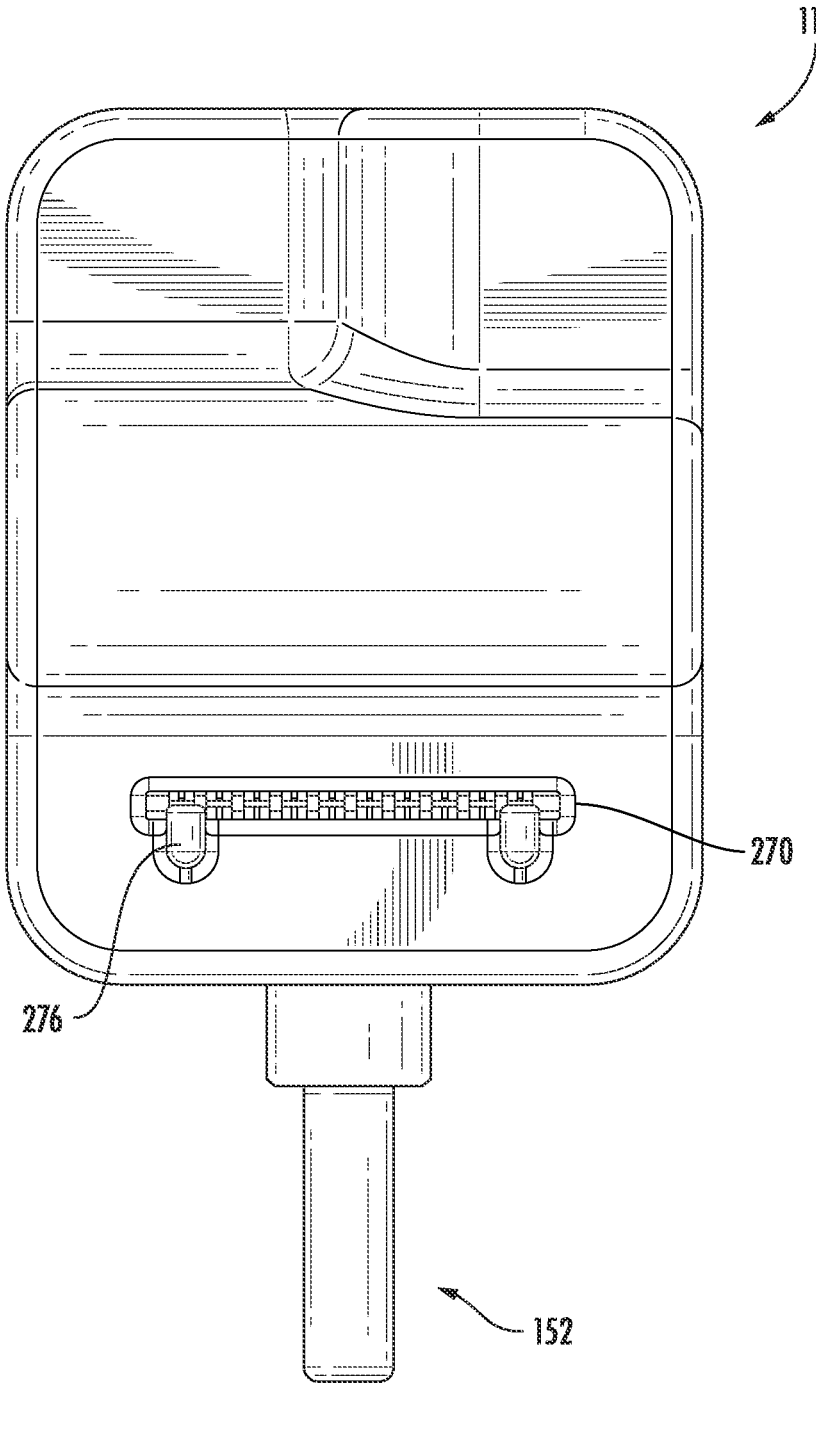
FIG. 6 is a perspective view of an example electronics housing for detachably connecting housing to a sensor support body.

FIG. 6 is a perspective view of electronics housing 110 illustrating electronics housing having an example male connector 152 for detachably connecting housing to sensor support body 102. Male connector 152 of electronics housing 110 can be inserted axially into female connector 150 of sensor support body 102 to attach the electronics housing to the sensor support body. Male connector 152 is illustrated as a pin extending downwardly from electronics housing 110, which may have a circular or other arcuate or non-arcuate (e.g., square) cross-sectional shape. If desired, the clinician can pull electronics housing 110 axially outwardly to withdraw male connector 152 from female connector 150, rotate or otherwise adjust the positional orientation of the electronics housing to a different positional orientation, and reinsert the male connector into the female connector. As discussed above, however, other complementary connector arrangements can be used between sensor support body 102 and electronics housing 110 without departing from the scope of disclosure.

With further reference to FIG. 5, intermediate region 144 of sensor support body 102 may include at least one alignment rod receiving hole through which an alignment rod can be inserted. For example, sensor support body 102 may have a single alignment rod receiving hole or may have multiple alignment rod receiving holes (e.g., arranged in series along the length of the sensor support body). Each alignment rod receiving hole may extend perpendicularly relative to the length of sensor support body 102 such that, when an alignment rod is inserted through the receiving hole, the alignment rod extends perpendicularly relative to the length of sensor support body 102. In the implementation of FIG. 5, alignment rod receiving hole 154 is positioned proximally from first joint insertion region 108 and electronics housing receiving area 146. Alignment rod receiving hole 154 may have a diameter ranging from 1 mm to 25 mm, such as from 2 mm to 15 mm, or 3 mm to 10 mm.

Sensor support body 102 in FIG. 5 includes intermediate region 144 offset proximally from first joint insertion region 108. Intermediate region 144 in this example includes bridge 136 extending from trailing edge 140 of first joint insertion region 108 to electronics receiving area 146. Bridge 136 has a smaller width then the width of first joint insertion portion 108 and the width of electronics receiving area 146. This can provide a comparatively narrow region for grasping system 100 and/or allowing the clinician to help visualize the joint space when inserting first joint insertion region 108 into the tibiofemoral joint. In other implementations, however, sensor support body 102 may not include a bridge 136 or may include a bridge having the same width as first joint insertion portion 108 and/or electronics housing receiving area 146.

Further, while the illustrated implementation includes first joint insertion region 108 and second joint insertion region 112, other configurations of intraoperative surgical system 100 and sensor support body 102 may include only a single joint insertion region. When so configured, intraoperative surgical system 100 and sensor support body 102 may have a joint insertion region configured as described in connection with first joint insertion region 108 or a joint insertion region configured as described in connection with second joint insertion region 112 herein. When so configured, intermediate region 144 may instead be labeled as a proximal region but may otherwise be generally configured as described with respect intermediate region 144 herein.

In some such applications, a system of multiple intraoperative surgical systems 100 may be provided, e.g., one of which includes a joint insertion region configured with first joint insertion region 108 as described herein and one of which includes a joint insertion region configured with second joint insertion region 112 as described herein. In other words, in lieu of having a single sensor support body 102 with two different joint insertion portions, a system of two different support bodies 102 each having a single joint insertion portion albeit differently configured may be provided. The one or more force sensors 106 and electronics housing 110 may be movable between and separately utilizable on each of the different sensor support bodies in the system. Alternatively, a different force sensor in electronics housing may be provided for each of the different sensor support bodies in the system.

In either case, sensor support body 102 in FIG. 5 includes second joint insertion portion 112 positioned on a second side of sensor support body 102. Second joint insertion portion 112 may be configured to be inserted into the tibiofemoral joint prior to resecting femur 12 and tibia 14. In some applications, second joint insertion portion 112 does not carry one or more force sensors 106 and is not intended to be utilized to measure load forces across the joint. In these applications, second joint insertion portion 112 may be utilized to locate intraoperative surgical system 100 relative to the tibiofemoral joint, e.g., positioning sensor support body 102 extending proximally outwardly from the joint. For example, the clinician may insert an alignment rod through alignment rod receiving aperture 154 and position second joint insertion portion 112 in the tibiofemoral joint. The clinician can then check and/or adjust an alignment of one or more bones using the alignment rod extending through alignment rod receiving aperture 154 while second joint insertion portion 112 is inserted into the tibiofemoral joint space.

Additionally or alternatively, one or more force sensors 106 may be carried by second joint insertion portion 112 to measure load forces across the tibiofemoral joint. For example, one or more force sensors 106 may be positioned on a planar surface provided by second platform 137 of second joint insertion portion 112 and optionally a sensor cover 104 placed over the one or more force sensors. The resulting assembly can be inserted into the tibiofemoral joint to measure load forces across the tibiofemoral joint prior to resecting femur 12 and tibia 14.

Second joint insertion portion 112 is illustrated as extending from a leading edge 156 at the second end 118 of sensor support body 102 to a trailing edge 158. During use, leading edge 156 of second joint insertion portion 112 is advanced into the tibiofemoral joint space before trailing edge 158 (with trailing edge 158 optionally positioned in or out of the tibiofemoral joint space). Second joint insertion portion 112 also defines a width between first side edge 122 and second side edge 124.

Second joint insertion portion 112 can have a variety of different shape configurations to facilitate positioning in the tibiofemoral joint. In some implementations, second joint insertion portion 112 is and/or includes a contiguous plate of material. Additionally or alternatively, second joint insertion portion 112 may be divided into different lengthwise portions by corresponding gaps or void spaces.

For example, in the implementation of FIG. 5, second joint insertion portion 112 includes a first lengthwise portion 160 and a second lengthwise portion 162, with the two lengthwise portions separated by a void space 164. Void space 164 may be an air gap region devoid of material otherwise defining second joint insertion portion 112. Each lengthwise portion 160, 162 may have a length (in the Y-direction) greater than a width (in the X-direction).

In different configurations, the widthwise size of void space 164 (in the X-direction) may be less than, greater than, or substantially equal to the width of first lengthwise portion 160 and/or second lengthwise portion 162. Further, while void space 164 is illustrated as being substantially centered in a widthwise direction across second joint insertion portion 112 (e.g., such of the center of the void space in the widthwise direction is aligned with the center of the second joint insertion portion in the widthwise direction), the void space may be offset relative to the center of the joint insertion portion in other configurations.

Configuring second joint insertion portion 112 with a void space 164 between opposed lengthwise portions may be useful to help facilitate installation of the second joint insertion portion in the native knee joint. Prior to resecting femur 12 and tibia 14, soft tissue and/or one or more bony protrusions may hinder insertion of second joint insertion portion 112 into the tibiofemoral joint space. Providing void space 164 may be useful to facilitate installation of second joint insertion portion 112 in the tibiofemoral joint space, allowing first lengthwise portion 160 and second lengthwise portion 162 to be inserted into the joint space with void space 164 provided where tissue and/or bone are located in the joint space that may otherwise inhibit insertion.

For example, intercondylar eminence 24 (FIG. 1) in the tibiofemoral joint space may have a tendency to block insertion of an object into the joint space because of the raised bony projection provided by the intercondylar eminence. Void space 164 may be configured (e.g., sized, shaped, and/or positioned) to accommodate intercondylar eminence 24 of tibia 14. When so configured, when second joint insertion portion 112 is inserted into the tibiofemoral joint space, first lengthwise portion 160 may be positioned in one compartment of the knee on one side of intercondylar eminence 24, second lengthwise portion 162 may be positioned in a second compartment of the knee on an opposite side of the intercondylar eminence, and the intercondylar eminence located in the void space between the two lengthwise portions.

It should be appreciated that while second joint insertion portion 112 is generally described as being inserted into the native tibiofemoral joint prior to resecting femur 12 and tibia 14, the clinician may or may not clean out and/or prepare the joint space before inserting second joint insertion portion 112. For example, the clinician may insert a saw blade, an osteotome, and/or other cutting instrument into the tibiofemoral joint space to cut soft tissue (e.g., cartilage) and/or bony protrusions (e.g., such as but not limited to intercondylar eminence 24) prior to inserting the second joint insertion portion 112 in the joint space. This can help open the tibiofemoral joint space sufficiently to allow second joint insertion portion 112 (including any optional one or more force sensors 106 and/or sensor cover 104) into the joint space. The cutting of any bony portion of femur 12 and/or tibia 14 during such joint preparation is not a resection of femur 12 and/or tibia 14 within the meaning of the present application. Rather, reference to resecting femur 12 and/or tibia 14 herein refers to cutting the bone a sufficient amount to configure the bone to receive a prosthetic component attached thereto, with multiple resections optionally being performed to configure the bone to receive the prosthetic component with the specific fit desired by the surgeon.

In some configurations, first lengthwise portion 160 and second lengthwise portion 162 extend from leading edge 156 at second end 118 of sensor support body 102 back toward first end 116 of the sensor support body the entire length of second joint insertion portion 112 (e.g., to trailing end 158 where second joint insertion portion 112 intersects intermediate region 144 or, when configured without an intermediate region, first joint insertion portion 108). In other configurations, second joint insertion portion 112 includes a region that is not divided by void space 164.

For example, in FIG. 5, second joint insertion portion 112 includes a first region extending over the length of first lengthwise portion 160 and second lengthwise portion 162. Second joint insertion portion 112 also includes a second region extending proximally from the ends of the two of lengthwise portions, where the two lengthwise portions joined together to form a region of contiguous material that is not divided by void space 164. As illustrated, first lengthwise portion 160 and second lengthwise portion 162 have a length extending from leading edge 156 to a proximal end 166 where the two lengthwise portions merged together and close void space 164. Second joint insertion portion 112 continues proximally from the proximal end 166 where the two lengthwise portions merged together to terminal edge 158 in the illustrated configuration. As shown, a bridge of narrower cross-sectional width connects second joint insertion portion 112 to intermediate portion 144, although the sensor support body 102 may be configured without such a narrow bridge.

While the dimensions of second joint insertion portion 112 may vary, in some implementations, the second joint insertion portion has a maximum length from leading edge 156 to trailing edge 166 ranging from 25 mm to 200 mm, such as from 40 mm to 100 mm, or from 50 mm to 60 mm. Second joint insertion portion 112 may have a maximum width from first side edge 122 to second side edge 124 ranging from 20 mm to 100 mm, such as from 30 mm to 80 mm, or from 50 mm to 70 mm.

When configured with first lengthwise portion 160 and second lengthwise portion 162, each lengthwise portion may have a length within a range from 10% to 100% of the overall length of second joint insertion portion 112, such as from 25% to 75% of the overall length, or from 40% to 60%. The width first lengthwise portion 160 and second lengthwise portion 162 may each be less than 50% of the maximum overall width of second joint insertion portion 112, such as less than 40%, less than 30%, or less than 20% of the overall width. Void space 164 may have a length defined by the length of first lengthwise portion 160 and second lengthwise portion 162 (in the within any of the ranges for those portions discussed above). In some examples, void space 164 has a width ranging from 20% to 80% of the overall maximum width second joint insertion portion 112, such as from 25% to 50% of the overall width. In implementations, void space 164 defines a length greater than a width, and the length of the void space ranges from 20% to 80% of the length of the second joint insertion portion, such as from 30% to 70% of the length.

As introduced with respect to FIG. 4, intraoperative surgical system 100 can include a sensor cover 104 that is positioned over sensor support body 102 with one or more force sensors 106 interposed between the sensor support body and sensor cover. Sensor cover 104 may be positioned over the one or more force sensors 106 without physically and/or mechanically attaching the sensor cover to any portion of intraoperative surgical system 100. Alternatively, sensor cover 104 may be positioned over the one or more force sensors 106 and physically and/or mechanically attached to sensor support body 102. Sensor cover 104 may be attached directly to sensor support body 102 or may be indirectly attached to the sensor support body, e.g., by being attached to electronics housing 110 and/or a portion of the electrical circuit electrically connected to the one or more force sensors 106, in each case which is in turn directly or indirectly connected to sensor support body 102.

When configured with sensor cover 104, the sensor cover may be permanently or detachably coupled to sensor support body 102. For example, sensor cover 104 may be detachably coupled to sensor support body 102, allowing the sensor cover to be provisionally engaged with the sensor support body and removable therefrom (e.g., for changing force sensors and/or the sensor cover). When configured with a sensor cover 104 that is attachable to and detachable from sensor support body 102, a connector system may be provided between the sensor cover and sensor support body.

Sensor cover 104 can be detachably coupled to sensor support body 102 in a variety of different configurations. Sensor cover 104 and sensor support body 102 (or a component attachable thereto) can have one or more connectors that releasably engage each other to provisionally secure the sensor cover to the sensor support body, either directly or indirectly via one or more components that are in turn attached to the sensor support body. Sensor support body 102 (or a component attachable thereto) may include one or more sensor cover connectors, and sensor cover 104 may include one or more complementary connectors configured to engage with a corresponding one of the sensor cover connectors to detachably connect the sensor cover to the sensor support body. For example, one of sensor support body 102 (or a component attachable thereto) and sensor cover 104 may have a female connector and the other of the components may have a male connector that is insertable into the female connector to interconnect the sensor cover with the sensor support body.

The one or more connectors used to detachably connect sensor cover 104 to sensor support body 102 can be positioned at any suitable location along the length of intraoperative surgical system 100. In some examples, one or more connectors are located in the region defined by a joint insertion portion (e.g., first joint insertion portion 108), allowing sensor cover 104 to be affixed at a location where the sensor cover is subsequently inserted into the tibiofemoral joint space. Additionally or alternatively, sensor cover 104 may be detachably coupled to sensor support body 102 at a location offset from the joint insertion region. For example, sensor cover 104 may be detachably coupled to sensor support body 102, directly or indirectly, at a location that is proximally offset from the joint insertion region. When the joint insertion region is subsequently inserted into the tibiofemoral joint space in such an implementation, sensor cover 104 may be connected to sensor support body 102 at a location outside of the joint space (e.g., without being connected to any portion of the sensor support body positioned in the joint space).

Configuring intraoperative surgical system 100 with a sensor cover 104 that connects to sensor support body 102 outside of the joint insertion portion may be useful to help generate accurate force measurements across the tibiofemoral joint space. The one or more force sensors 106 positioned between sensor support body 102 and sensor cover 104 in the joint insertion portion can measure an axial load across the tibiofemoral joint, when the joint insertion portion is inserted into the joint space. If one or more connectors are positioned extending between sensor cover 104 and sensor support body 102 in the joint insertion portion, the connectors may interfere with loading across the joint insertion portion and corresponding force measurements.

Figure 7A:
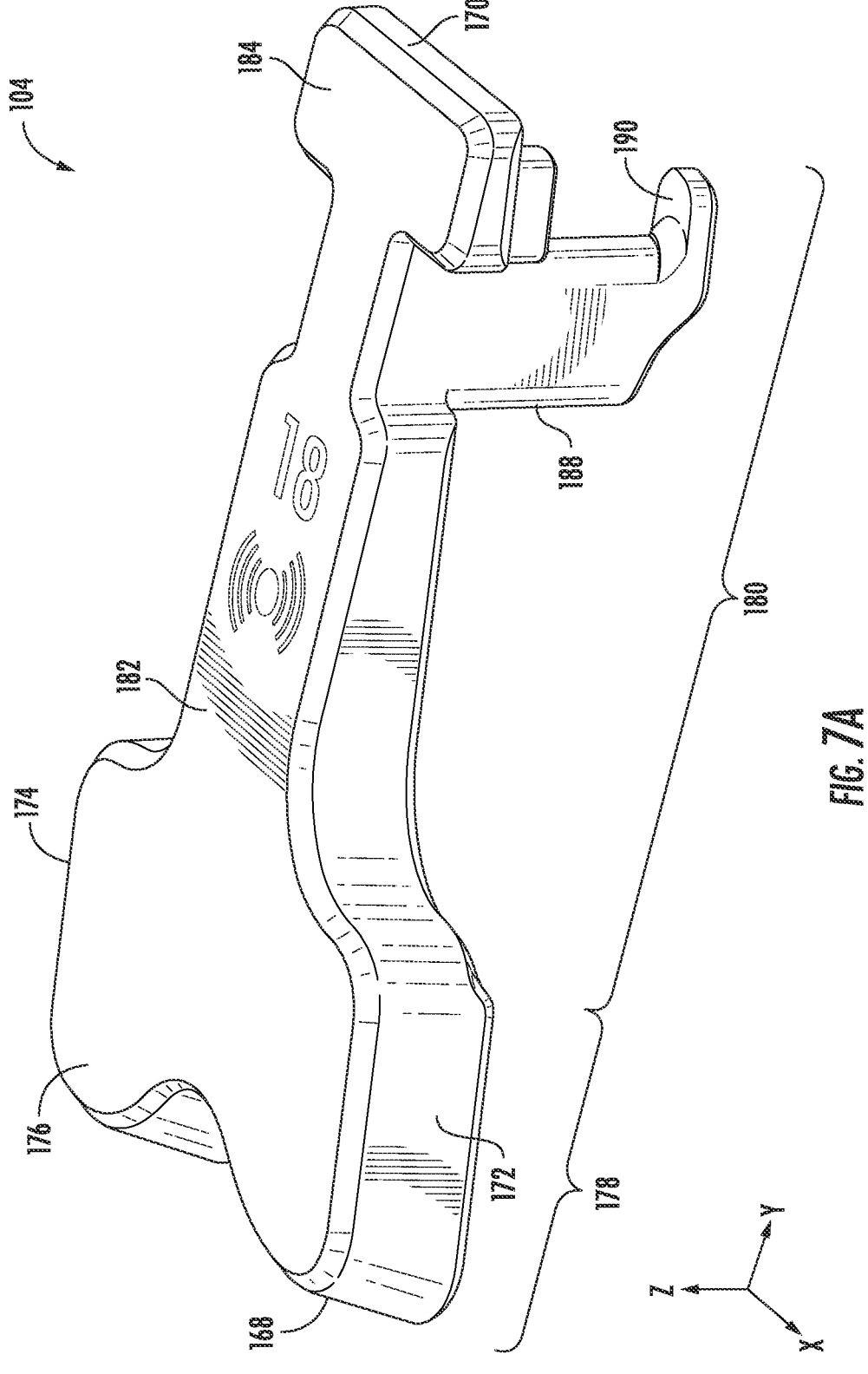
FIGS. 7A-7D are different views of an example configuration of a sensor cover that can be used with an intraoperative surgical system.
Figure 7B:
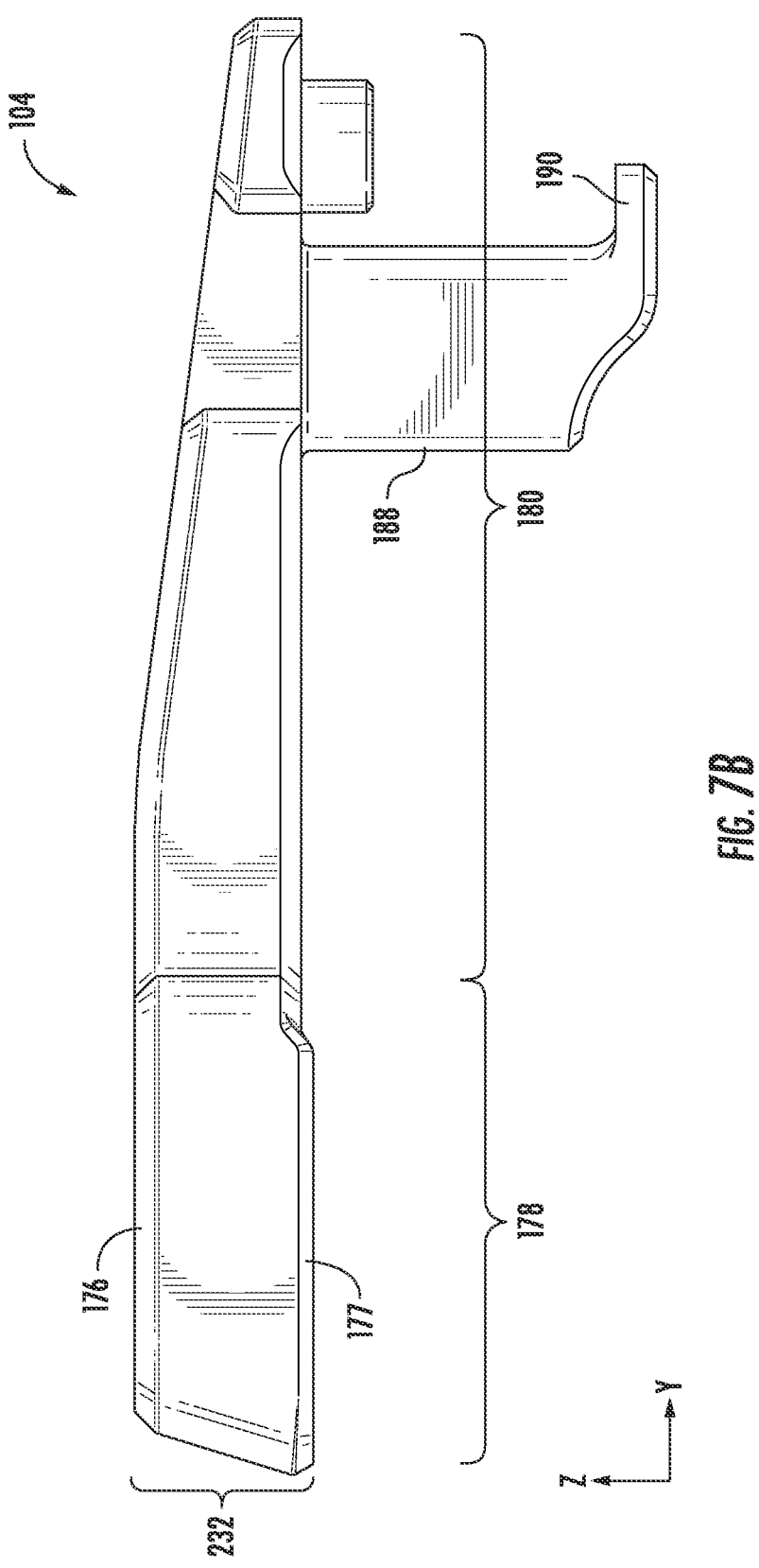
Figure 7C:
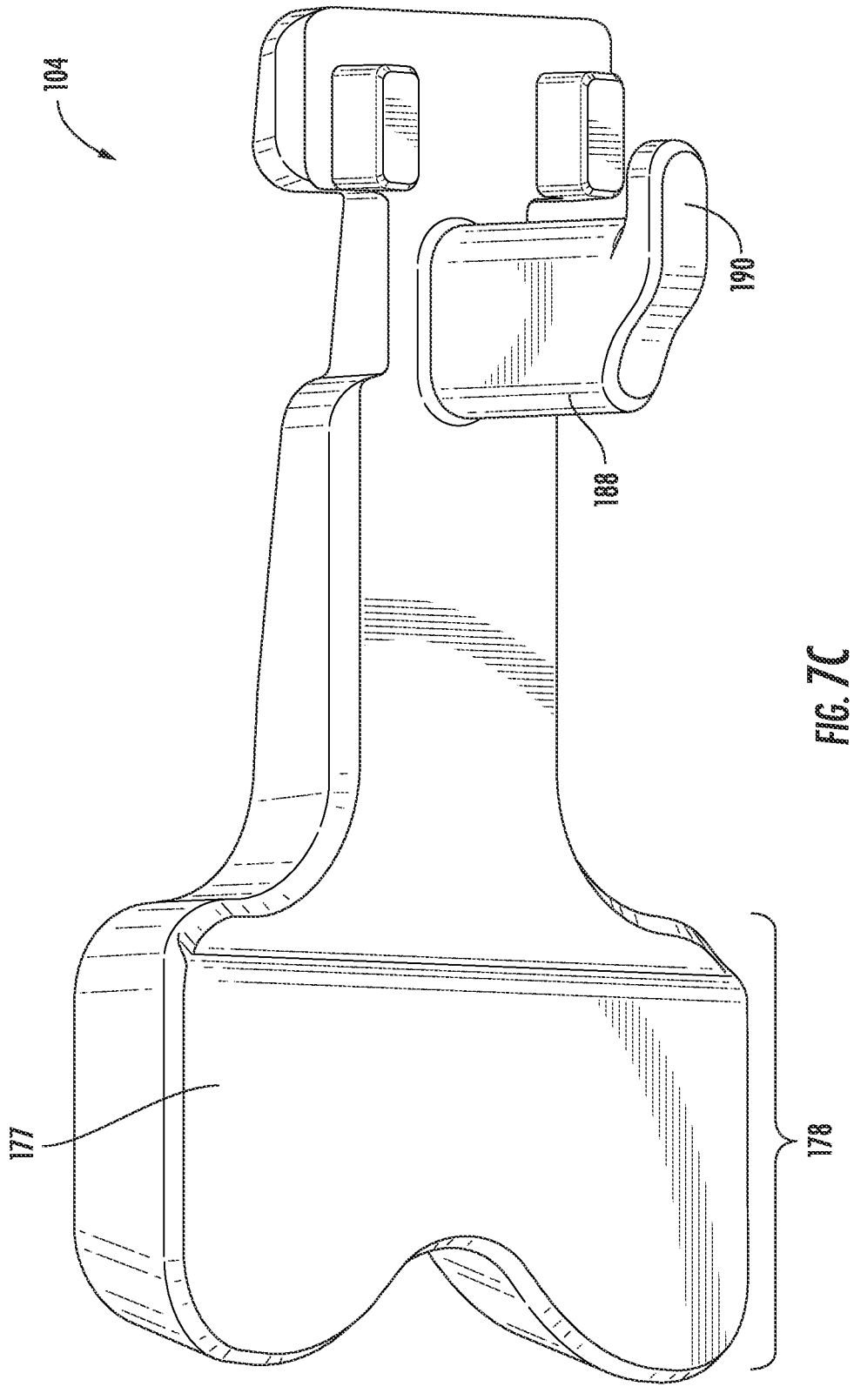
Figure 7D:
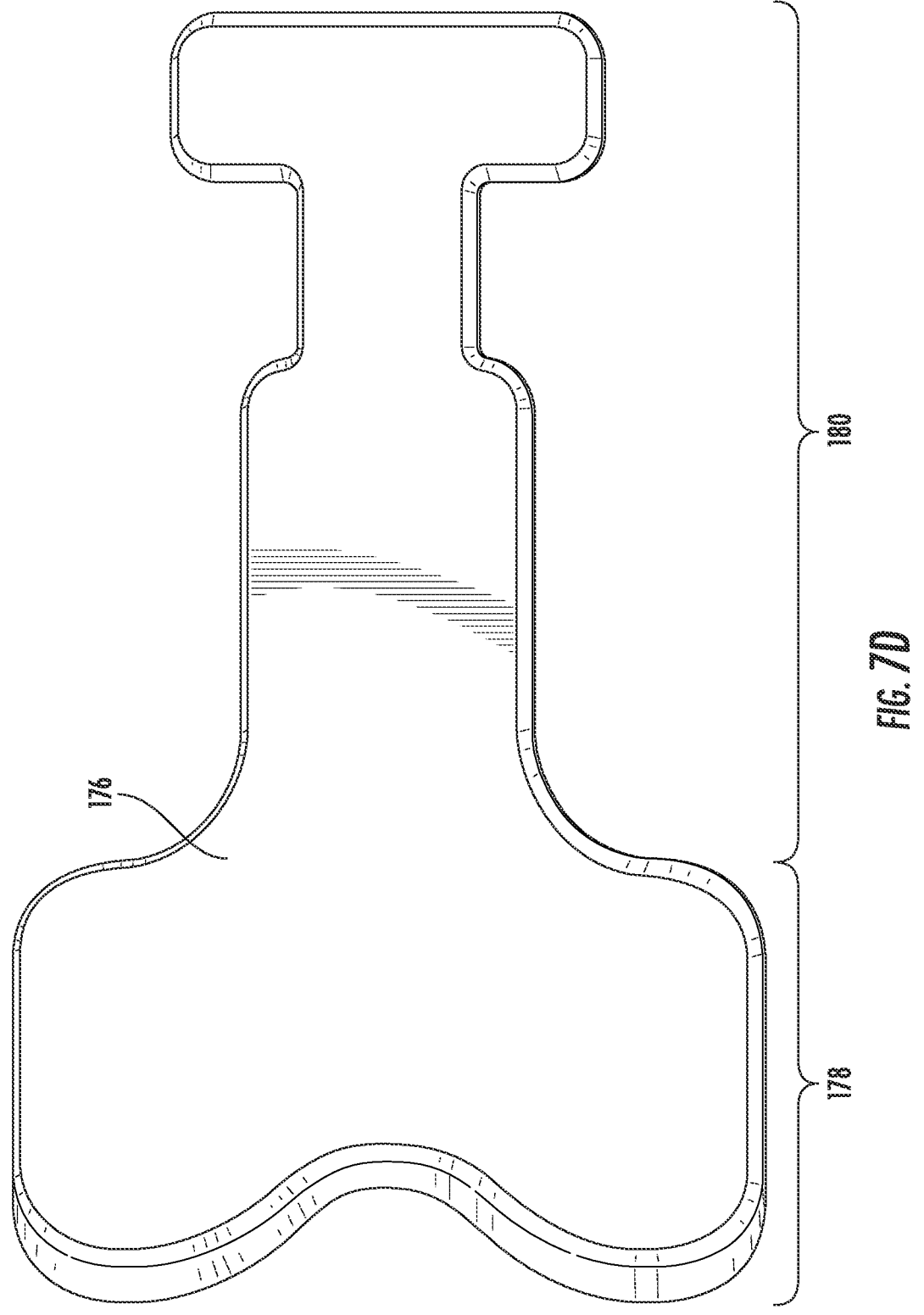

In general, sensor cover 104 may be implemented as any suitable structure that at least partially, and in some examples fully, covers one or more force sensors 106 positioned on sensor support body 102. FIGS. 7A-7D (collectively referred to as "FIG. 7") are different views of an example configuration of sensor cover 104 that can be used with intraoperative surgical system 100. FIG. 7A is a perspective view of the sensor cover. FIG. 7B is a side view of the sensor cover. FIG. 7C is a top view of the sensor cover. FIG. 7D is a bottom of the sensor cover.

As shown, sensor cover 104 may have a length extending from a first end 168 to a second end 170 (in the Y-direction indicated on FIG. 5) and a width extending from a first side edge 172 to a second side edge 174 (in the X-direction indicated on FIG. 5). Sensor cover 104 can have a top surface 176 and a bottom surface 177 defining a thickness of the sensor cover therebetween (in the Z-direction indicated on FIG. 5).

Sensor cover 104 may be configured to at least partially, and in some examples fully, cover a joint insertion portion of sensor support body 102 (e.g., at least the region of the joint insertion portion on which one or more force sensors 106 are positioned). In the example of FIG. 7, sensor cover 104 defines a covering region 178 configured to cover a joint insertion region (e.g., first joint insertion region 108) of sensor support body 102. Covering region 178 may be referred to as a platform covering region one covering a platform of the sensor support body, such as first platform 132. Covering region 178 of sensor cover 104 may be sized and/or shaped according to any of the configurations discussed above with respect to a joint insertion portion and/or platform of sensor support body 102. For example, covering region 178 may have a size and/or shape that mirrors the size and/or shape of the joint insertion portion over which the cover is configured to be positioned.

Sensor cover 104 may or may not include an additional cover region configured to be positioned outside of the tibiofemoral joint, when the joint insertion portion of sensor support body 102 and corresponding covering region 178 of sensor cover 104 are inserted into the joint. For example, sensor cover 104 may include a connector covering region 180 extending lengthwise and proximally away from covering region 178. Connector covering region 180 may be positionable over a region of sensor support body 102 extending from the joint insertion region proximally back to intermediate region 144. Connector covering region 180 may be configured to cover an electrical connector extending from the one or more force sensors positioned on the joint insertion portion back to electronics housing 110 located in intermediate region 144.

As with covering region 178, connector covering region 180 may or may not have a size and/or shape that mirrors the size and/or shape of the portion of sensor support body 102 covered by the connector covering region. For example, where sensor support body 102 includes a bridge 136 having a reduced cross-sectional width, connector covering region 180 may define a corresponding covering bridge 182 of reduced cross-sectional width compared to covering region 178. In some implementations, the maximum width of covering region 178 between first side edge 172 and second side edge 174 is at least twice the width of connector covering region 180. In some implementations, covering bridge 182 extends proximally to a proximal-most enlargement having a comparatively larger width than covering bridge 182 positioned adjacent to and/or in contact with electronics housing 110.

Sensor cover 104 terminates in a leading or distal edge at the first end 168 of the cover and extends between first and second side edges 172 and 174. In some examples, one or more of the edges defining sensor cover 104 are tapered across the thickness of the sensor cover. For example, in the illustrated configuration of FIG. 7, the leading edge at first end 168 and the first and second side edges 172, 174 are illustrated as defining a slope extending from the top surface to the bottom surface of the cover (across the thickness). The slope edge surfaces taper proximally moving from bottom surface 177 to a top surface 176. When so configured, the bottom surface 177 of sensor cover 104 may define a greater cross-sectional area than the top surface 176 of the sensor cover. Configuring sensor cover 104 with one or more sloped edge surfaces may be useful to help facilitate installation of intraoperative surgical system 100 into the tibiofemoral joint space. The slope leading edge of intraoperative surgical system 100 can function as a wedge to help guide the system into the joint space. In some implementations, one or more corresponding edges of sensor support body 102 may be tapered in addition to or in lieu of tapering the edges of sensor cover 104.

When sensor cover 104 is configured to detachably attach to sensor support body 102, any suitable connector system can be used to form an engagement between the sensor cover and sensor support body to retain the sensor cover to the sensor support body during insertion into the tibiofemoral joint space. The connector system may form a mechanical engagement between the components, a magnetic engagement between the components, and/or other engagement between the components. For example, sensor support body 102 can have one or more sensor cover connectors and sensor cover 104 can have one or more complementary connectors configured to engage the one or more sensor cover connectors.

In the illustrated implementation of FIGS. 5 and 7, sensor support body 102 includes at least one aperture 186 through which at least one projection 188 extending from sensor cover 104 can be inserted. Aperture 186 is shown as being located between first joint insertion portion 108 and electronics receiving area 146. Aperture 186 can be defined as an opening extending through the thickness of sensor support body 102. Aperture 186 can have any appropriate shape, which can include an arcuate shape (e.g., circle, oval) and/or polygonal shape (e.g., square, rectangle, triangle). Projection 188 can be configured (size and/or shaped) to be inserted into aperture 186. Projection can have any desired shape, including shapes described as being suitable for aperture 186.

In some examples, aperture 186 can be sized larger than projection 188 in one or more dimensions to allow the projection to be inserted into the aperture and move relative to the aperture. For example, aperture 186 may define a slot having a length extending in the lengthwise direction of sensor support body 102 greater than a width of the aperture. Projection 188 may have a length less than the length of the slot defined by aperture 186. In use, projection 188 can be inserted into the slot defined by aperture 186 (e.g., at the distal end of the slot) and moved within the slot (e.g., slid proximally in the slot) to a connection position.

In some implementations, a locking feature 190 may be provided that extends outwardly (e.g., at a 90° or other angle) from projection 188. For example, projection 188 may extend downwardly (e.g., at a 90° or other angle) from bottom surface 177 of sensor cover 104 and locking feature 190 may extend outwardly (e.g., in a proximal direction) from a proximal edge of projection 188. During assembly, projection 188 can be inserted into a slot defined by aperture 186 of sensor support body 102 (e.g., with one or more force sensors positioned between the sensor support body and sensor cover) in the sensor cover advanced proximally along the sensor support body. As sensor cover 104 is moved proximally along the length of sensor support body 102, projection 188 can slide within the slot defined by aperture 186, e.g., until the proximal edge of projection 188 contacts the proximal end of the slot. Locking feature 190 can be positioned at a location along the length of projection 188 greater than the thickness of sensor support body 102, e.g., such that the locking feature is positioned under sensor support body 102 when projection 188 is advanced to a proximal-most position in the slot. The top surface of the locking feature 190 may or may not contact the bottom surface 130 of sensor support body 102 when so positioned.

Providing a connection system in which projection 188 can move relative to slot 186 can be useful to help interconnect the one or more force sensors 106 to electronics housing 110. During assembly, in electrical connector extending from the one or more force sensors 106 may be advanced proximally along the length of sensor support body 102 to connect the one or more force sensors to electronics housing 110. Configuring sensor cover 104 to move proximally along the length of sensor support body 102 can help facilitate connection between the electrical connector associated with the one or more force sensors 106 and electronics housing 110.

Independent of the specific configuration of the connector system connecting sensor cover 104 to sensor support body 102, the position of the sensor cover relative to the sensor support body may be fixed (e.g., immovable) after engaging the components together. Alternatively, the connection system may facilitate some amount of relative movement between sensor cover 104 and sensor support body 102 after engaging the components together. Sensor cover 104 may be connected to sensor support body 102 so as to be axially displaceable relative to the sensor support body (e.g., in the Z-direction indicated on FIG. 4). When so configured, the axial separation between sensor support body 102 and sensor cover 104 (across the thickness of intraoperative surgical system 100) may not be fixed but may instead be variable. This can allow the separation distance between sensor support body 102 and sensor cover 104 to vary (e.g., compress or reduce with the one or more force sensors positioned therebetween compressing or reducing in thickness as a result) when intraoperative surgical system 100 is placed in the tibiofemoral joint space and variable forces are applied across the thickness of the surgical system. This can allow the force between femur 12 and tibia 14 to transfer through sensor support body 102 and sensor cover 104 for measurement by the one or more force sensors 106 positioned between the sensor support body and sensor cover. In other configurations, however, sensor support body 102 and/or sensor cover 104 may be formed of a material that is sufficiently compressible so as to allow the one or more force sensors 106 to measure forces between the components without having relative movement between the sensor support body and sensor cover.

In addition to or in lieu of providing a connector system that facilitates axial movement between sensor support body 102 and sensor cover 104, the connector system may facilitate lateral movement between the sensor support body and sensor cover. For example, when the connector system provides a single connection point between sensor support body 102 and sensor cover 104, the sensor cover may be configured to rotate laterally within a bounded range of travel relative to sensor support body 102.

Figure 8:
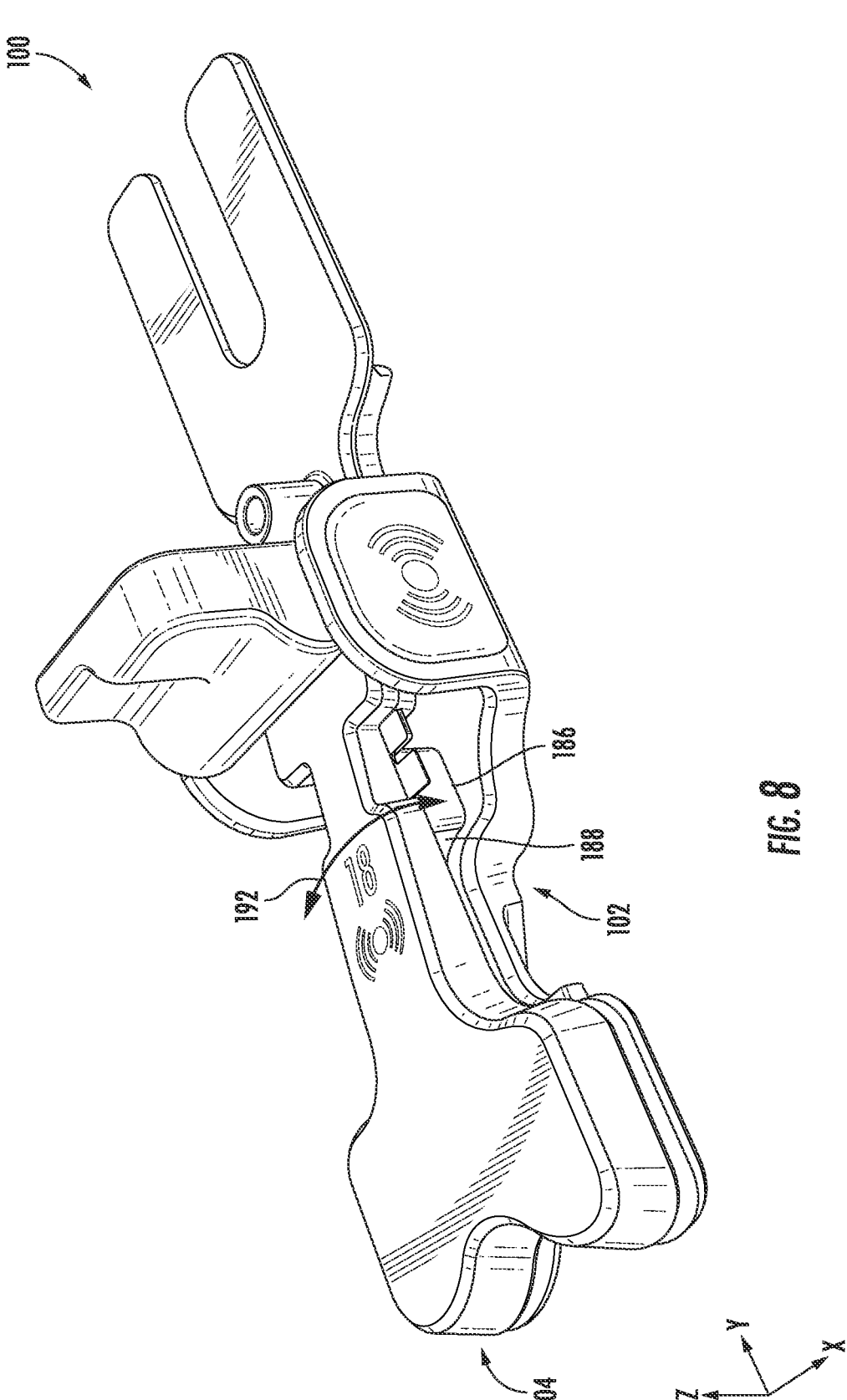
FIG. 8 is a perspective view of an intraoperative surgical system showing an example lateral displacement configuration of a sensor cover relative to a sensor support body.

FIG. 8 is a perspective view of intraoperative surgical system 100 showing an example lateral displacement configuration of sensor cover 104 relative to sensor support body 102. As shown in this example, sensor cover 104 is detachably connected to sensor support body 102 at a location that is proximally offset from first joint insertion portion 108. The connection between sensor cover 104 and sensor support body 102 may facilitate rotational movement of the distal end of the sensor cover relative to the distal end of the sensor support body, e.g., about a rotation arc 192. For example, aperture 186 may be sized and/or shaped relative to projection 188 to allow the projection to rotate a limited amount within the aperture. As various examples, sensor cover 104 may rotate relative to sensor support body 102 within an arc 192 of less than 45°, such as less than 35°, less than 25°, less than 15°, less than 10°, or less than 5°. For example, sensor cover 104 may rotate relative to sensor support body 102 within an arc 192 from 1° to 25°, such as from 2° to 15°, or from 3° to 10°.

Configuring sensor cover 104 to be laterally displaceable relative to sensor support body 102 (once detachably coupled to the sensor support body) may be helpful to facilitate insertion of intraoperative surgical system 100 into the tibiofemoral joint space. In practice, blocking anatomy and/or the comparative tightness of the tibiofemoral joint space may inhibit insertion of the intraoperative surgical system into the joint space. Configuring sensor support cover 104 to be shifted laterally relative to sensor support body 102 can provide "play" or flexibility that allows intraoperative surgical system 100 to adjust as it is being inserted into the tibiofemoral joint space. This can ease insertion of the system into the joint space. That being said, in other configurations, sensor cover 104 may be attached to sensor support body 102 without having lateral relative movement between the components once affixed together.

Figure 9A:
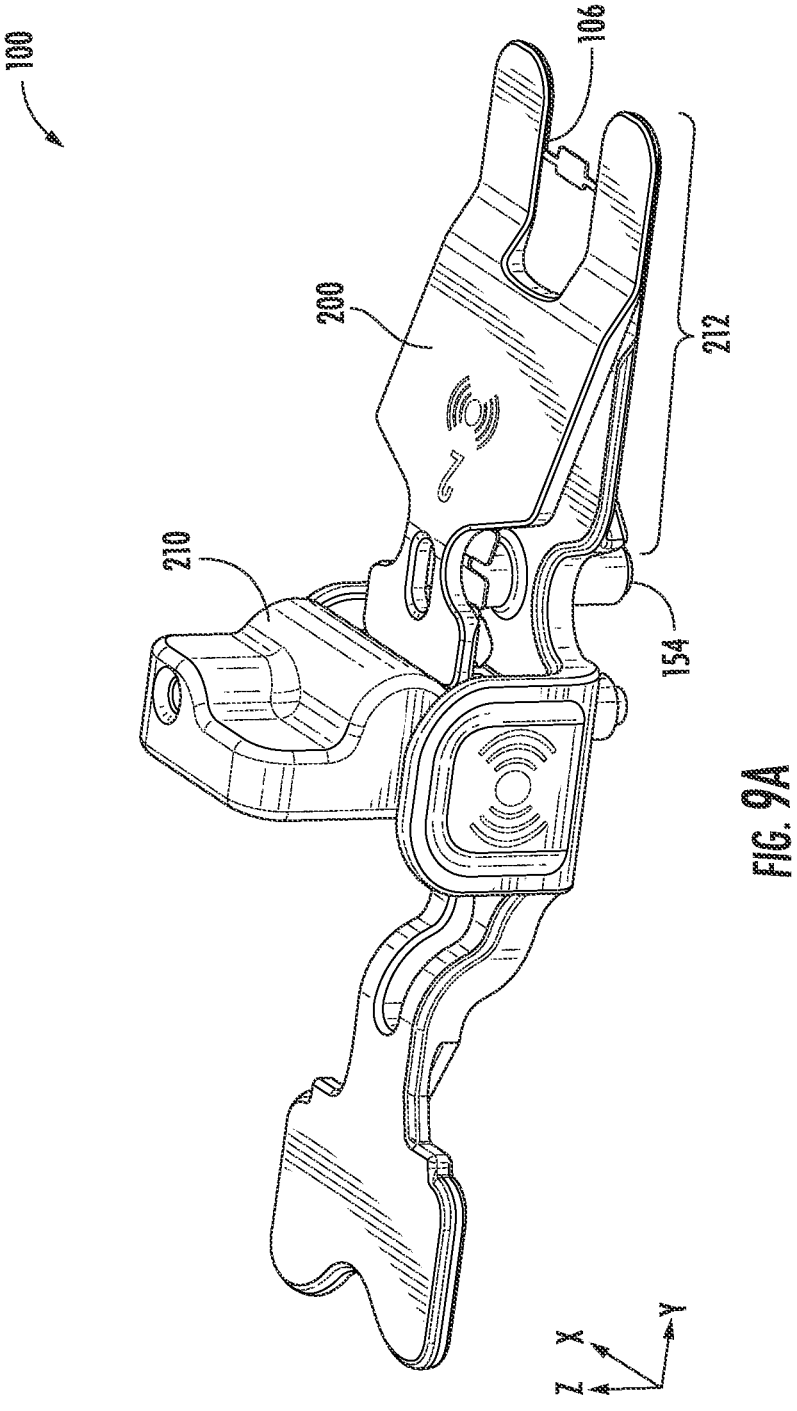
FIGS. 9A and 9B are perspective and exploded views, respectively, of an example configuration of an intraoperative surgical system illustrating another example sensor cover configuration.
Figure 9B:
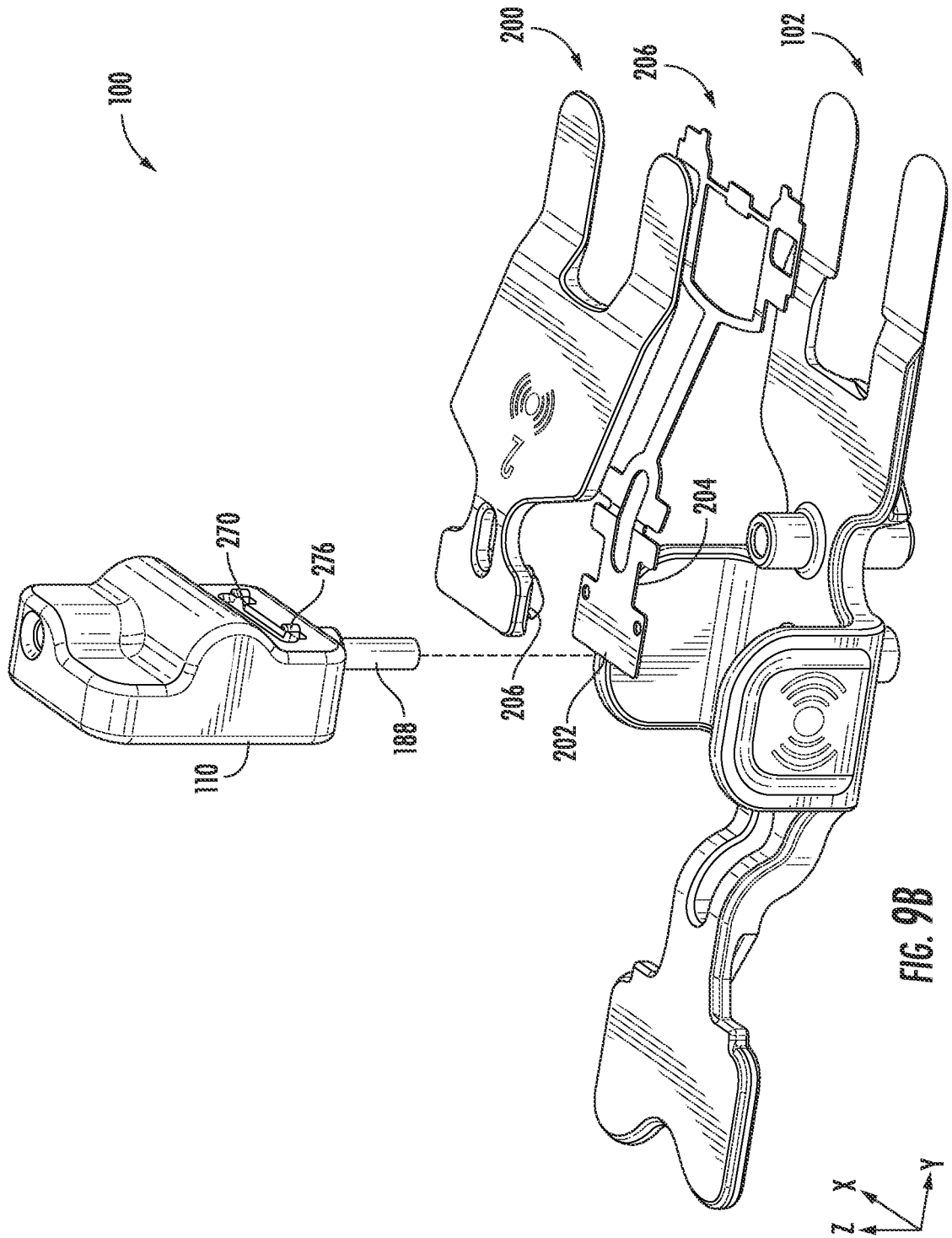
Figure 10A:
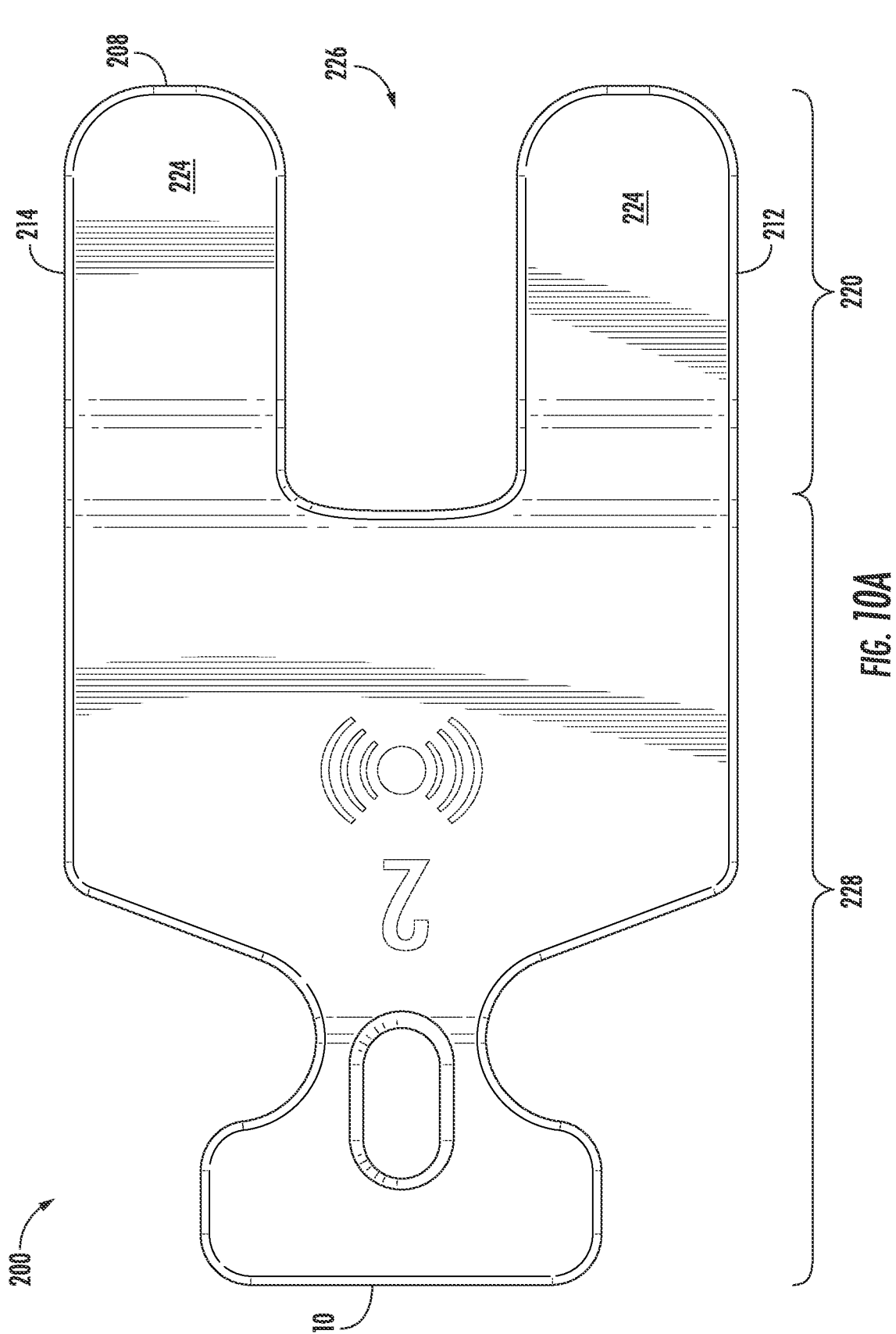
FIGS. 10A-10C are a top, a side, and a bottom perspective view, respectively, of an example configuration of a sensor cover that can be used with the intraoperative surgical system.
Figure 10B:
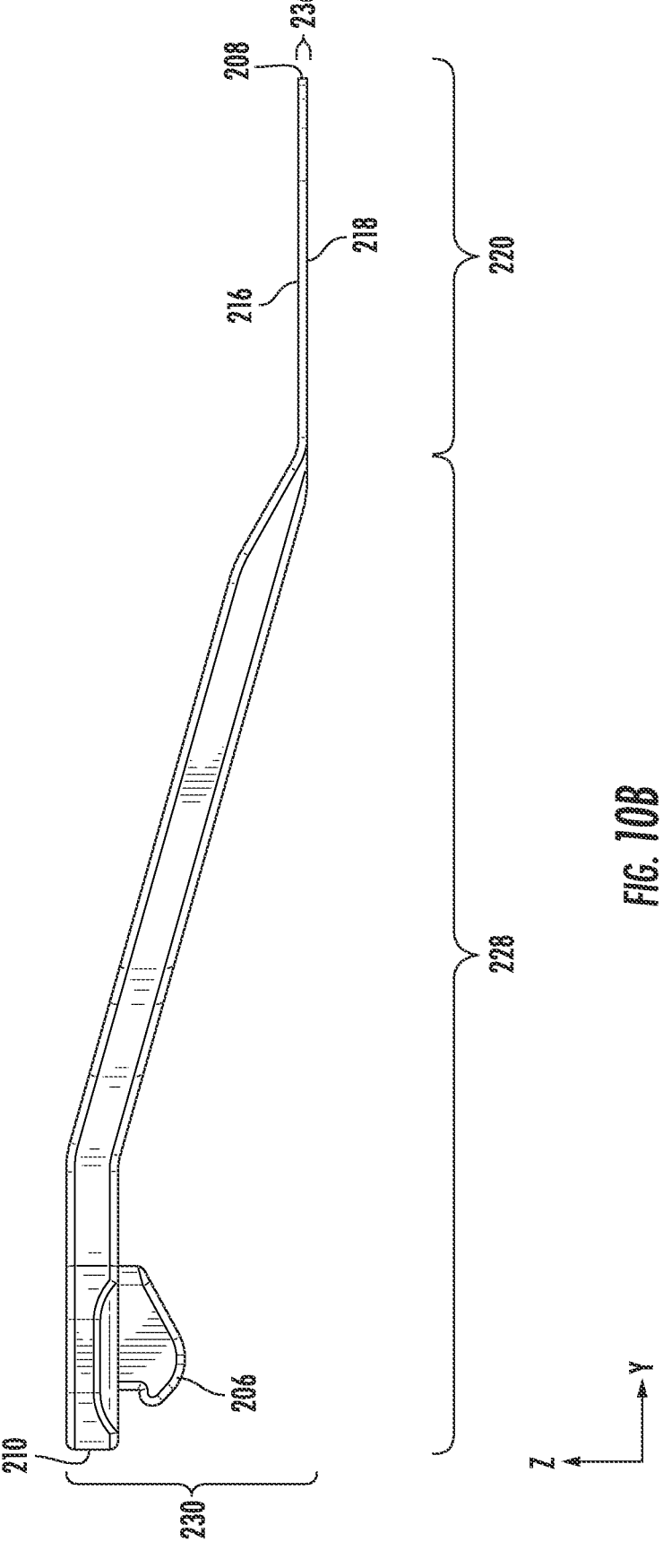

A sensor cover for intraoperative surgical system 100 can have a variety of different configurations and implementations. FIGS. 9A and 10B (collectively referred to as "FIG. 9") are perspective and exploded views, respectively, of an example configuration of intraoperative surgical system 100 illustrating another example sensor cover configuration. In the example of FIG. 9, a sensor cover 200 is illustrated as being positionable over second joint insertion portion 112 to sandwich one or more force sensors 106 between the sensor cover 200 and second joint insertion portion. Sensor cover 200 can have any of the configuration details and connection arrangements discussed above with respect to sensor cover 104.

In the illustrated example of FIG. 9, sensor cover 200 is illustrated as a comparatively thin sensor cover configured to be positioned over second joint insertion portion 112 with the one or more force sensors 106 interposed between sensor cover and joint insertion portion of sensor support body 102. The resulting combination of second joint insertion portion 112, the one or more force sensors 106, and sensor cover 200 can be inserted into the tibiofemoral joint, such as the native tibiofemoral joint before resecting either femur 12 or tibia 14. Sensor cover 200 can be permanently or detachably attached, either directly or indirectly, to sensor support body 102 to form a resulting structure insertable into the tibiofemoral joint space.

Sensor cover 200 may be positioned over the one or more force sensors 106 without physically and/or mechanically attaching the sensor cover to any portion of intraoperative surgical system 100. Alternatively, sensor cover 200 may be positioned over the one or more force sensors 106 and physically and/or mechanically attached to sensor support body 102. Sensor cover 200 may be attached directly to sensor support body 102 or may be indirectly attached to the sensor support body, e.g., by being attached to electronics housing 110 and/or a portion of the electrical circuit electrically connected to the one or more force sensors 106, in each case which is in turn directly or indirectly connected to sensor support body 102.

Sensor cover 200 can be detachably coupled to sensor support body 102 in a variety of different configurations. Sensor cover 200 and sensor support body 102 (or a component attachable thereto) can have one or more connectors that releasably engage each other to provisionally secure the sensor cover to the sensor support body, either directly or indirectly via one or more components that are in turn attached to the sensor support body. For example, one of sensor support body 102 (or a component attachable thereto) and sensor cover 200 may have a female connector and the other of the components may have a male connector that is insertable into the female connector to interconnect the sensor cover with the sensor support body.

The one or more connectors used to detachably connect sensor cover 200 to sensor support body 102 can be positioned at any suitable location along the length of intraoperative surgical system 100. In some examples, one or more connectors are located in the region defined by a joint insertion portion (e.g., second joint insertion portion 112), allowing sensor cover 104 to be affixed at a location where the sensor cover is subsequently inserted into the tibiofemoral joint space. Additionally or alternatively, sensor cover 200 may be detachably coupled to sensor support body 102 at a location offset from the joint insertion region. For example, sensor cover 200 may be detachably coupled to sensor support body 102, directly or indirectly, at a location that is proximally offset from the joint insertion region.

In the example of FIG. 9, the one or more force sensors 106 are electrically connected to an electrical connector 202 extending proximally from second joint insertion portion 112. Electrical connector 202 can electrically connect the one or more force sensors to electronics housing 110. Sensor cover 200 can be detachably coupled to electrical connector 202 which, in turn, is attached to sensor support body 102 via electronics housing 110. In this way, sensor cover 200 can detachably couple to sensor support body 102.

For example, in the illustrated arrangement, the circuit electrically connecting the one or more force sensors 106 may define at least one aperture 204 through which at least one projection 206 extending from sensor cover 200 can be inserted. Aperture 204 can be defined as an opening extending through the thickness of the circuit electrically connected to force sensors 106. Aperture 204 may be mounted about its entire perimeter by the material defining electrical circuit or, as illustrated, may have an open side wall (e.g., defining a generally U-shaped opening). Aperture 204 can have any appropriate shape, which can include an arcuate shape (e.g., circle, oval) and/or polygonal shape (e.g., square, rectangle, triangle). Projection 206 can be configured (size and/or shaped) to be inserted into aperture 204. Projection 206 can have any desired shape, including shapes described as being suitable for aperture 204.

Figure 10C:
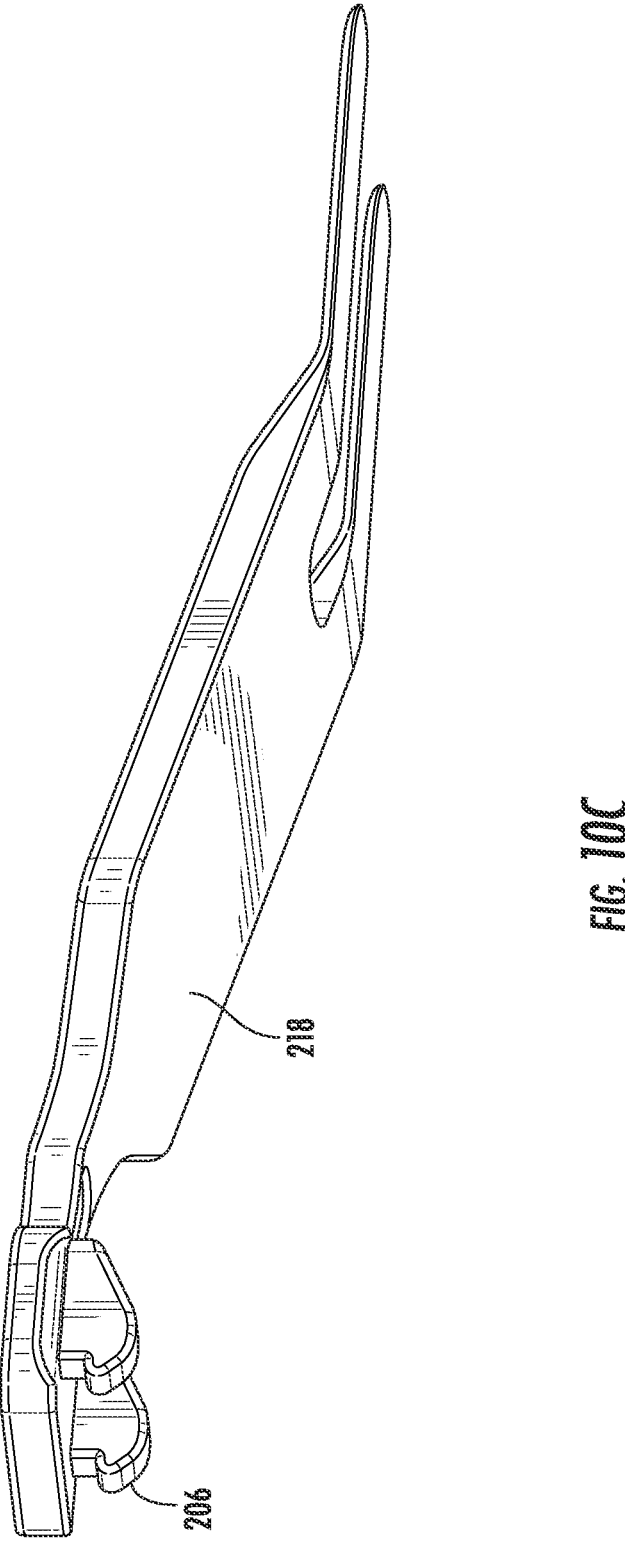

In general, sensor cover 200 may be implemented as any suitable structure that at least partially, and in some examples fully, covers one or more force sensors 106 positioned on sensor support body 102. FIGS. 10A-10C (collectively referred to as "FIG. 10") are a top, a side, and a bottom perspective view, respectively, of an example configuration of sensor cover 200 that can be used with intraoperative surgical system 100.

As shown, sensor cover 200 may have a length extending from a first end 208 to a second end 210 (in the Y-direction indicated on FIG. 10) and a width extending from a first side edge 212 to a second side edge 214 (in the X-direction indicated on FIG. 10). Sensor cover 200 can have a top surface 216 and a bottom surface 218 defining a thickness of the sensor cover therebetween (in the Z-direction indicated on FIG. 10).

Sensor cover 200 may be configured to at least partially, and in some examples fully, cover a joint insertion portion of sensor support body 102 (e.g., at least the region of the joint insertion portion on which one or more force sensors 106 are positioned). In the example of FIG. 10, sensor cover 200 defines a covering region 220 configured to cover at least a portion of a joint insertion region (e.g., second joint insertion region 112) of sensor support body 102 on which the one or more force sensors 106 are positioned. Covering region 220 of sensor cover 200 may be sized and/or shaped according to any of the configurations discussed above with respect to a joint insertion portion and/or platform of sensor support body 102. For example, covering region 220 may have a size and/or shape that mirrors the size and/or shape of the region of joint insertion portion 112 over which the cover is configured to be positioned.

For example, as discussed above with respect to FIG. 5, second joint insertion portion 112 of sensor support body 102 may be configured with first lengthwise portion 160 and second lengthwise portion 162, with the two lengthwise portions separated by void space 164. Covering region 220 of sensor cover 200 may have a size and/or shape corresponding to (e.g., substantially matching) the size and/or shape of the region of second joint insertion portion 112 to be covered by the covering region. For example, covering region 220 of sensor cover 200 may have a first lengthwise covering portion 202 and a second lengthwise covering portion 224, with a void space 226 defined between the two lengthwise covering portions. The lengthwise covering portions and void space of covering region 220 can have a size and/or shape corresponding to the lengthwise portions and void space of second joint insertion portion 112. Accordingly, the lengthwise covering portions 222, 224 and void space 226 of covering region 220 of sensor cover 200 can have any of the size and configuration details discussed above with respect to corresponding regions of second joint insertion portion 112.

Sensor cover 200 may or may not include an additional cover region configured to be positioned outside of the tibiofemoral joint, when the joint insertion portion of sensor support body 102 and corresponding covering region 220 of sensor cover 200 are inserted into the joint. For example, sensor cover 200 may include a connector covering region 228 extending lengthwise and proximally away from covering region 220. Connector covering region 228 may be positionable over a region of sensor support body 102 extending from the joint insertion region proximally back to intermediate region 144 and/or electronics housing 110. Connector covering region 228 may be configured to cover an electrical connector extending from the one or more force sensors positioned on the joint insertion portion back to electronics housing 110 located proximally of the one or more force sensors 106.

Sensor cover 200 may extend in a single plane (X-Y plane) or may exhibit a height transition between a distal portion positioned in a first plane (X-Y plane) and a proximal portion positioned in a second plane (X-Y plane) offset across the height of intraoperative surgical system 100 (in the Z-direction). For example, as seen in FIG. 10B, sensor cover 200 may define a height offset 230 between the top surface 216 at the first end 208 of the sensor cover and the top surface 216 at the second end 210 of the sensor cover. Height offset 230 may be useful to bridge a barrel defining alignment rod aperture 154 and/or position electrical connector 202 electrically connected to the one or more force sensors 106 at an elevation suitable for engaging a complementary electrical connector defined by electronics housing 110. When configured with height offset 230, sensor cover 200 may define a sloped height transition and/or a stepped offset (e.g., 90° elevation change). In some examples, height offset 230 of sensor cover 200 ranges from 5 mm to 50 mm, such as from 10 mm to 40 mm, 15 mm to 30 mm, or from 17 mm to 25 mm.

Sensor cover 200 defines a thickness (in the Z-direction) between top surface 216 and bottom surface 218. The thickness of sensor cover 200 may be substantially uniform across the sensor cover or may vary (e.g., increase, decrease) across the length and/or width of the sensor cover. For example, the region of sensor cover 200 configured to be inserted into the tibiofemoral joint space (e.g., covering region 220) may be comparatively thinner than a proximal portion of the sensor cover configured to remain outside of the tibiofemoral joint space (e.g., connector covering region 228). This may be useful to provide a comparatively thin region insertable into the tibiofemoral joint space and a comparatively thicker region outside of the tibiofemoral joint space (e.g., for structural support and rigidity). In the illustrated example, sensor cover 200 defines a first planar surface insertable into the tibiofemoral joint space having a first thickness, a second planar surface remaining outside of the tibiofemoral joint space having a second thickness greater than the first thickness, and a thickness transition region (e.g., taper) between the two planar surfaces.

With intraoperative surgical system 100 assembled, a sensor cover can be positioned over the sensor support body with one or more force sensors interposed between the sensor cover and sensor support body. For example, the sensor cover can be attached, directly or indirectly, to the sensor support body with the one or more force sensors sandwiched between the sensor cover and the sensor support body. The force sensors can contact a top surface (e.g., planar top surface) of the sensor support body on one side and a bottom surface (e.g., planar bottom surface) of the sensor cover on the opposite side. The resulting assembly can collectively define a joint insertion block configured to be inserted into the tibiofemoral joint space for measuring a force between the femur 12 and tibia 14.

For example, with reference to FIG. 4, intraoperative surgical system 100 can have a first joint insertion block 240 defined by sensor support body 102 (e.g., platform 132 of the sensor support body), sensor cover 104, and one or more force sensors 106 positioned between the sensor support body and sensor cover. With reference to FIG. 9A, intraoperative surgical system 100 can have a second joint insertion block 242 defined by sensor support body 102, sensor cover 200, and one or more force sensors 106 positioned between the sensor support body and sensor cover. As referenced above, intraoperative surgical system 100 in different implementations can have a single joint insertion portion or multiple joint insertion portions and, correspondingly, can have a single joint insertion block (e.g., configured according to either first joint insertion block 240 or second joint insertion block 242) or multiple joint insertion blocks.

Each region described as being a joint insertion block can be a unit or module formed by the constituent components defining the block that is insertable into the tibiofemoral joint space. The joint insertion block can have any suitable cross-sectional shape, including arcuate shapes, polygonal shapes, and combinations thereof. In use, an entire length of the joint insertion block can be inserted into the tibiofemoral joint space, or only a portion of the length of the joint insertion block may be inserted into the tibiofemoral joint space with a proximal portion of the block remaining outside of the tibiofemoral joint space.

The one or more joint insertion blocks defined by intraoperative surgical system 100 can be configured to measure the force across the tibiofemoral joint at different points in the joint replacement process. For example, the one or more joint insertion blocks can be positioned to measure the force across the joint before cutting either the tibia or femur, after resecting one but not both of the tibia and femur, and/or resecting both the tibia and femur. When configured to measure the force across the joint between the opposed surfaces of the tibia and the femur after resecting both the tibia and the femur, the joint insertion portion can be configured to be inserted into the joint space without a trial and/or permanent prosthetic component attached to either the tibia or the femur, with a prosthetic component attached to one but not both of the tibia the femur, and/or with a prosthetic component attached to both the tibia and femur.

In general, the size of the tibiofemoral joint space changes depending on whether one or both of femur 12 and tibia 14 are resected and/or whether a prosthetic component is attached to either or both of the bones. Accordingly, the thickness of the one or more regions of intraoperative surgical system 100 intended to be placed in the tibiofemoral joint space to make force measurements can be configured depending on when in the surgical workflow the surgical system is intended to be used in the expected size of the joint space at that point in the surgical process. The thickness may be sufficiently small to allow the joint insertion block to be inserted into the joint space but sufficiently large to have femur 12 and tibia 14 press against the joint block, either directly or indirectly through a prosthetic component, for measuring a load force.

For example, first joint insertion block 240 may have a thickness measured from the bottom surface of sensor support body 102 to the top surface of sensor cover 104 (in the Z-direction). Second joint insertion block 242 may have a thickness measured from the bottom surface of sensor support body 102 to the top surface of sensor cover 200 (in the Z-direction). In some implementations, first joint insertion block 240 has a thickness sized effective to configure the joint insertion block to be inserted into the tibiofemoral joint space with one or both of femur 12 and tibia 14 resected. The thickness may be sized to configure the joint insertion block to be inserted into the tibiofemoral joint space with or without a prosthetic component attached to femur 12 and/or tibia 14. Second joint insertion block 242 may have a thickness sized effective to configure the joint insertion block to be inserted into the tibiofemoral joint space prior to resecting either femur 12 or tibia 14. This can allow the joint insertion block 242 to be inserted into the native tibiofemoral joint space.

The tibiofemoral joint space is comparatively small in the native knee joint prior to resecting either femur 12 or tibia 14. When a joint insertion block (e.g., second joint insertion block 242) is sized to be positioned in the native tibiofemoral joint prior to resecting femur 12 and tibia 14, the thickness of the joint insertion block may likewise be comparatively small. For example, the thickness may be less than 5 mm, such as less than 4 mm, less than 3.5 mm, less than 3 mm, less than 2.5 mm, or less than 2 mm. For example, the thickness may be within a range from approximately 0.5 mm (e.g., ±10%) to approximately 4 mm, such as approximately 1 mm to approximately 3.5 mm, or from approximately 2 mm to approximately 3 mm.

A joint insertion block having a thickness corresponding to any of the foregoing example thickness values (or having yet different thickness) may also be configured to be inserted into the tibiofemoral joint space after resecting both femur 12 and tibia 14 and attaching a prosthetic component to both bones (e.g., affixing femoral prosthetic component 60 to femur 12 and tibial prosthetic component 62 to tibia 14 without tibial insert 64 positioned between femoral prosthetic component 60 and tibial prosthetic component 62). This may be useful to measure load forces across the tibiofemoral joint during trialing and/or after installation of the permanent prosthetic components.

In contrast to measuring loads across the native knee joint, when one or both of femur 12 and tibia 14 are resected during the surgical procedure, the distance separating femur 12 from tibia 14 is enlarged. The separation distance may be largest when both femur 12 and tibia 14 are resected but without a prosthetic component being attached to either of the bones (e.g., a full gap separating the resected distal head of femur 12 from the resected proximal plateau of tibia 14). When a joint insertion block (e.g., first joint insertion block 240) is sized to be positioned in the tibiofemoral joint after resecting both femur 12 and tibia 14 but prior to attaching any prosthetic components, the thickness of the joint insertion block may be comparatively large. For example, the thickness may be within a range from approximately 15 mm to approximately 30 mm, such as from approximately 16 mm to approximately 25 mm, from approximately 17 mm to approximately 22 mm, or from approximately 18 mm to approximately 21 mm.

A joint insertion block (e.g., first joint insertion block 240) may also have a thickness sized effective to be positioned in a half gap joint space. For example, the joint insertion block may be inserted into the tibiofemoral joint after resecting one but not both of femur 12 and tibia 14, without installing a prosthetic component on the resected bone. Additionally or alternatively, the joint insertion block may be inserted into the tibiofemoral joint after resecting both femur and tibia and installing a prosthetic component on one but not both resected bones. In either case, the resulting size of the tibiofemoral joint may be larger than the native knee joint but smaller than the full gap size tibiofemoral joint. A joint insertion block (e.g., first joint insertion block 240) can be sized to be positioned in the tibiofemoral joint in the size configurations. For example, the joint insertion block may have a thickness within a range from approximately 6 mm to approximately 15 mm, such as from approximately 7 mm to approximately 14 mm, approximately 8 mm to approximately 13 mm, or approximately 9 mm to approximately 12 mm.

The thickness of a joint insertion block defined by intraoperative surgical system 100 can be sent by controlling the thickness of the constituent components defining the block, e.g., the thickness of sensor support body 102, the thickness of sensor cover 104/200, and/or the thickness of the one or more force sensors 106 and electrical circuit connected thereto. In typical applications, the thickness of the one or more force sensors 106 and electrical circuit connected thereto may be small compared to the thickness of sensor support body 102 and sensor cover 104/200. Accordingly, the thickness of the joint insertion block may be predominantly set by controlling the thickness of the sensor support body and sensor cover in the region defining the joint insertion block. In this regard, a joint insertion block can be configured with any of the foregoing described sizes and size ranges by controlling the thickness of sensor support body 102 and/or sensor cover 104/200. Sensor support body 102 and sensor cover 104/200 may have the same thickness (e.g., dividing the overall thickness of the joint insertion block equally between the two components) or one of the components (e.g., sensor cover 104/200) may be comparatively thicker or thinner than the other component (e.g., sensor support body 102).

In some implementations, the thickness 126 (FIG. 5B) of sensor support body 102 in the region of the first joint insertion portion is within a range from 2 mm to 25 mm, such as from 2 mm to 10 mm, from 3 mm to 7 mm, or from 4 mm to 5 mm. Sensor cover 104 may define a thickness 232 (FIG. 7B) within a range from 2 mm to 25 mm, such as from 3 mm to 5 mm, from 5 mm to 7 mm, from 7 mm to 9 mm, from 9 mm to 11 mm, from 11 mm to 13 mm, from 13 mm to 15 mm, or from 15 mm to 17 mm. Different sensor covers 104 may have different thicknesses within any of the foregoing ranges.

Additionally or alternatively, sensor support body 102 may define a thickness 234 (FIG. in the region of the second joint insertion portion that is the same as or different than thickness 126. For example, thickness 234 in the region of the second joint insertion portion may be less than the thickness 126 of the first joint insertion portion. For example, thickness 234 in the region of the second joint insertion portion may be less than 5 mm, such as less than 4 mm, less than 3 mm, less than 2 mm, or less than 1 mm. For example, thickness 234 may range from 0.25 mm to 1.5 mm, such as from 0.5 mm to 1.0 mm. Sensor cover 200 may define a thickness 236 (FIG. 10B) less than 5 mm, such as less than 4 mm, less than 3 mm, less than 2 mm, or less than 1 mm. For example, thickness 236 of sensor cover 200 may range from 0.25 mm to 1.5 mm, such as from 0.5 mm to 1.0 mm.

In some implementations, second joint insertion block 242 has a thickness less than the thickness of first joint insertion block 240. For example, first joint insertion block 240 may be configured to be positioned in the tibiofemoral joint to make a force measurement across the joint after resection of one or both of femur 12 and tibia 14, with or without a prosthetic component attached to one or both bones. By contrast, first joint insertion block 240 may be configured to be positioned in the tibiofemoral joint to make a force measurement across the joint prior to resection of either of femur 12 or tibia 14.

Independent of whether intraoperative surgical system 100 defines a single joint insertion region and joint insertion block or multiple joint insertion regions and joint insertion blocks, each joint insertion block may be configured to be used with a single sensor cover or may be provided with a system of different interchangeable sensor covers. For example, intraoperative surgical system 100 may be configured with a single sensor cover 104/200 having a specific size and/or shape. The sensor cover may be permanently or detachably attached to sensor support body 102, either directly or indirectly, with one or more force sensors 106 positioned therebetween to form a joint insertion block insertable into the tibiofemoral joint space for measuring loads across the joint. Alternatively, intraoperative surgical system may include multiple interchangeable sensor covers. A clinician can select one of the multiple interchangeable sensor covers and attach the selected sensor cover to sensor support body 102. Each of the interchangeable sensor covers in the system may vary from each other interchangeable cover in one or more characteristics. However, each sensor cover in the system may have the same or corresponding connection features that allow the sensor cover to be selectively and removably attached to sensor support body 102, directly or indirectly via one or more intermediate components attached to sensor support body.

Implementing intraoperative surgical system 100 to have reconfigurable and interchangeable sensor covers 102/104 can be beneficial for a variety of reasons. The clinician can specifically configure the joint insertion block of the surgical system to the requirements of the specific patient undergoing the surgical procedure (e.g., modifying the surgical system to accommodate the size and/or other characteristics of the joint of the patient being operated on). Additionally or alternatively, configuring the joint insertion block of the surgical system to be reconfigurable can allow the clinician to collect measurable data at different points during the surgical procedure. For example, the clinician can modify the thickness of the joint insertion block to enable the joint insertion block to be inserted into different size tibiofemoral joint spaces (e.g., as the thickness of the space changes during surgery due to bone resection and/or installation or removal of prosthetic components).

Accordingly, in some examples, intraoperative surgical system 100 includes a plurality of sensor covers for a particular joint insertion block each configured to be detachably attached to sensor support body 102, directly or indirectly, with one or more force sensors 106 positioned between the sensor support body and a selected one of the plurality of sensor covers. When intraoperative surgical system 100 includes multiple joint insertion blocks 240, 242, sets of multiple sensor covers may be provided for each joint insertion block, or one joint insertion block may be provided with a set of multiple sensor covers and the other joint insertion block may be provided with only a single sensor cover or may not have any sensor covers whatsoever.

When intraoperative surgical system 100 includes a set of interchangeable sensor covers, each sensor cover can have one or more connectors that detachably attach to sensor support body 102, either directly or indirectly. Each sensor cover can have the same configuration of one or more connectors, including any of the configurations discussed herein as being examples, to allow the sensor covers to be interchangeably attached to sensor support body 102, or may have different connection configurations.

The specific number of sensor covers provided in a system of interchangeable sensor covers may vary and, in various examples, includes two, three, four or more interchangeable sensor covers. Each sensor cover may vary from each other of the plurality of interchangeable sensor covers in one or more characteristics. Example characteristics that may differentiate one sensor cover from an other interchangeable sensor cover in a set include, but are not limited to, a size of the sensor cover (e.g., a width, a length, and/or a thickness), a shape of the sensor cover, a material of construction of the sensor cover, and combinations thereof. In some examples, each sensor cover in the set of multiple interchangeable sensor covers varies from each other sensor cover in the set of multiple interchangeable sensor covers at least in the thickness of the sensor cover. For example, each sensor cover may have a different thickness (at least over the portion of the sensor cover configured to be inserted into the tibiofemoral joint space) than each other sensor cover.

Figure 11A:
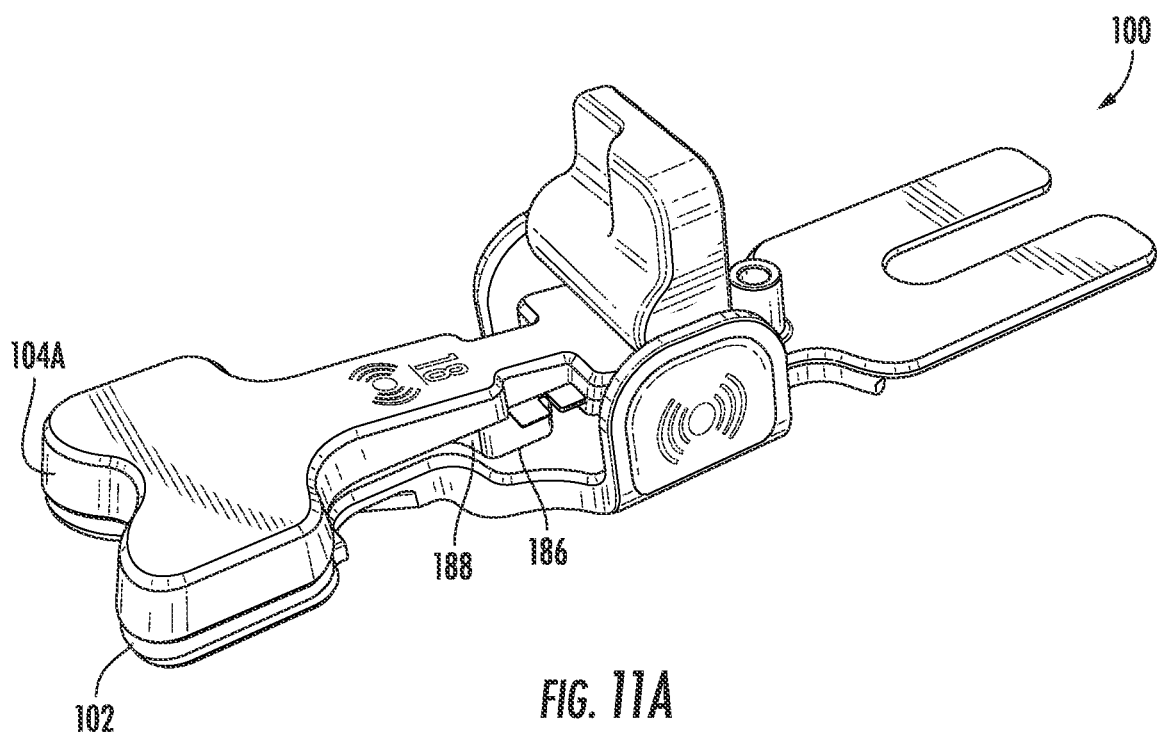
FIGS. 11A and 11B are perspective illustrations of an intraoperative surgical system implemented with two different sensor cover configurations.
Figure 11B:
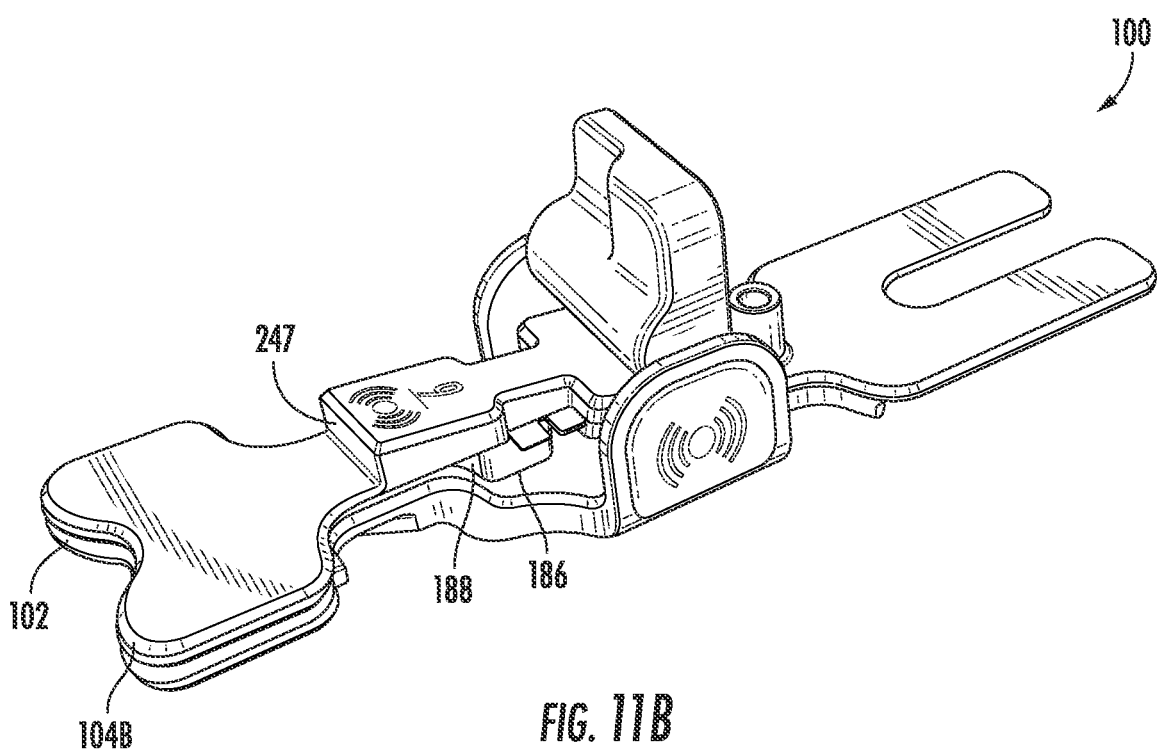

FIGS. 11A and 11B are perspective illustrations of intraoperative surgical system 100 implemented with two different sensor cover configurations. FIG. 11A illustrates a first sensor cover 104A having a first characteristic (e.g., thickness) attached to sensor support body 102. FIG. 11B illustrates a second sensor cover 104B having a second characteristic (e.g., thickness) different than the first characteristic attached to sensor support body 102. In the illustrated arrangement, first sensor cover 104A is thicker than second sensor cover 104B. First sensor cover 104A and second sensor cover 104B are each illustrated as having a connector in the form of projection 188 insertable into aperture 186 of sensor support body 102 to detachably attach the select sensor cover to the sensor support body.

In some configurations, the joint insertion block formed when using second sensor cover 104B is configured to be inserted into the tibiofemoral joint space after one but not both of femur 12 and tibia 14 are resected without a prosthetic component attached to the resected bone. For example, the clinician may resect tibia 14 and insert the joint insertion block that includes second sensor cover 104B into the tibiofemoral joint space with the distal head of femur 12 pressing on one side of the joint insertion block and a resected proximal end of tibia 14 pressing on the opposite side of the joint insertion block.

The joint insertion block formed when using second sensor cover 104B may also be configured to be inserted into the tibiofemoral joint space after both femur 12 and tibia 14 are resected with a prosthetic component attached to one but not both resected bones. For example, the clinician may resect femur 12 and tibia 14 and install a prosthetic component (e.g., a trial prosthetic component) on one but not both of femur 12 and tibia 14. In one such example, the clinician installs a prosthetic component on femur 12. The clinician can insert the joint insertion block that includes second sensor cover 104B into the tibiofemoral joint space with the prosthetic component of fixed to the resected distal head of femur 12 pressing on one side of the joint insertion block and a resected proximal end of tibia 14 pressing on the opposite side of the joint insertion block.

In some configurations, the joint insertion block formed when using first sensor cover 104A is configured to be inserted into the tibiofemoral joint space after both femur 12 and tibia 14 are resected without a prosthetic component attached to either resected bone. For example, the clinician may resect femur 12 and tibia 14 and insert the joint insertion block that includes first sensor cover 104A into the tibiofemoral joint space with the resected distal head of femur 12 pressing on one side of the joint insertion block and the resected proximal end of tibia 14 pressing on the opposite side of the joint insertion block.

First sensor cover 104A may have a thickness (at least over the portion of the sensor cover configured to be inserted into the tibiofemoral joint space) within a range from 7 mm to 17 mm, such as from 9 mm to 15 mm, or from 11 mm to 13 mm (e.g., approximately 12 mm). Second sensor cover 104B may have a thickness (at least over the portion of the sensor cover configured to be inserted into the tibiofemoral joint space) within a range from 1 mm to 7 mm, such as from 2 mm to 6 mm, or from 3 mm to 5 mm (e.g., approximately 4 mm).

Where the thickness of a component described herein varies across the component, the average thickness of the component (over the relevant region of comparison such as the joint insertion portion) may be used for comparison to a thickness value specified herein.

While intraoperative sensor system 100 has generally been described as having separate joint insertion portions and joint insertion blocks for being inserted into the native tibiofemoral joint and resected tibiofemoral joint, respectively, it should be appreciated that other implementations of the system may have a single joint insertion portion and/or joint insertion block insertable into the native tibiofemoral joint before and after resecting one or both of femur 12 and tibia 14. In these configurations, a system of different sensor covers may be provided that are individually attachable over the same joint insertion portion of sensor support body 102. A first sensor cover (e.g., configured according to sensor cover 200) may be attachable to the sensor support body to form a first joint insertion block insertable into the native knee joint. The first sensor cover may be removed after use and one or more additional sensor covers (e.g., configured according to sensor cover 104) attached to the joint insertion portion to form one or joint insertion blocks insertable into the prepared joint at different points in the joint replacement process.

Independent of the number and configuration of joint insertion portions and sensor covers, a distal portion of intraoperative surgical system 100 can be inserted into the tibiofemoral joint (e.g., with a proximal portion of the sensor system projecting out of the joint). In general, the clinician may insert the distal portion of the intraoperative surgical system to a posterior depth in the tibiofemoral joint effective to position the one or more force sensors 106 carried by the surgical system at a location where load forces are desired to be measured across the joint. The clinician may visualize the appropriate positioning of the intraoperative surgical system and the tibiofemoral joint and control the positioning of the surgical system by observing where the one or more force sensors 106 are positioned relative to where the tibiofemoral joint surgical system is inserted.

Additionally or alternatively, intraoperative surgical system 100 may include one or more guide features to facilitate positioning of the distal portion of the surgical system in the tibiofemoral joint. The one or more guide features may help guide the intraoperative surgical system to a consistent position in the tibiofemoral joint space relative to other aspects of the anatomy. For example, the one or more guide features may control a depth to which the intraoperative surgical system is inserted into the tibiofemoral joint space. This can help position the one or more force sensors 106 at a consistent location in the anterior to posterior direction in the tibiofemoral joint space.

When configured with a depth stop, the depth stop may be provided on sensor support body 102 and/or a sensor cover 104/200. The depth stop may be a projection and/or a region of increased material thickness offset from a remainder of the structure. When intraoperative surgical system 100 is inserted posteriorly into the tibiofemoral joint, the one or more depth stops may contact an anterior side of femur 12 and/or tibia 14 to limit a depth to which the intraoperative surgical system can be inserted into the joint space.

Figure 12:
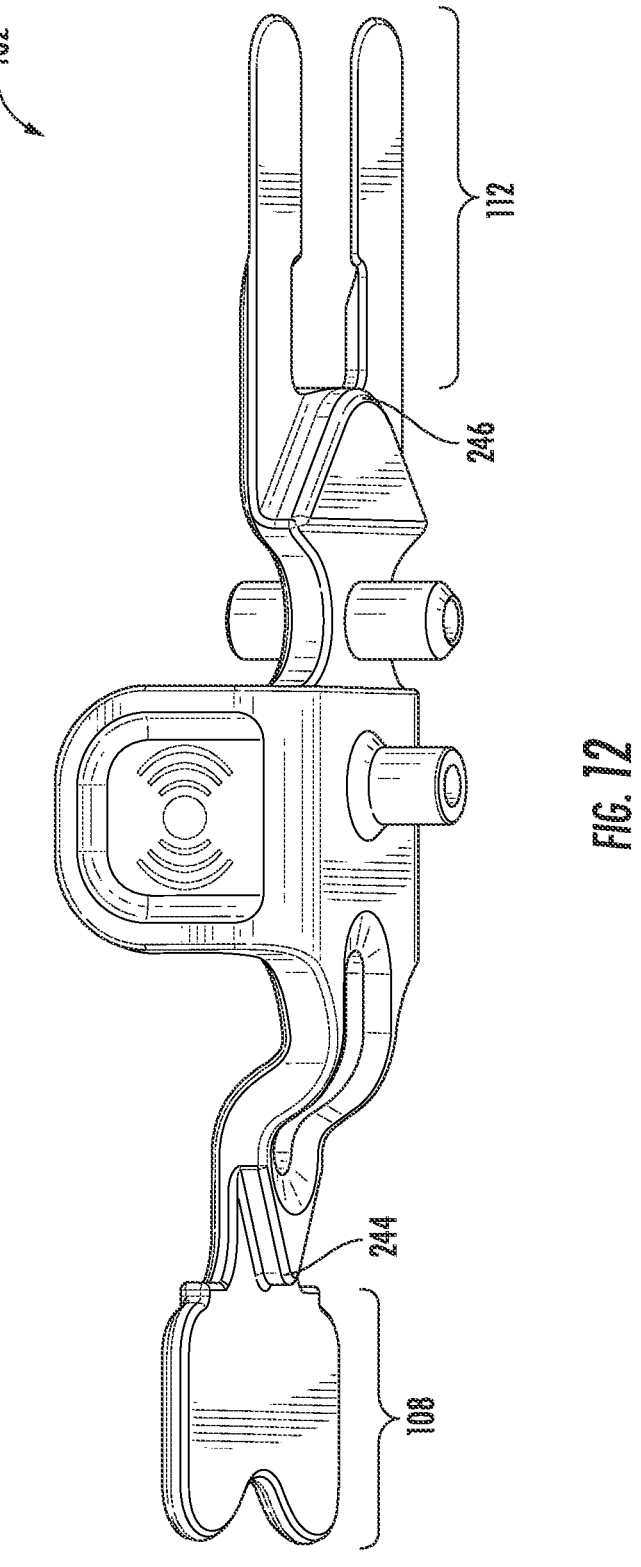
FIG. 12 is a bottom perspective view of a sensor support body illustrating an example depth stop.

FIG. 12 is a bottom perspective view of sensor support body 102 of intraoperative surgical system 100 illustrating an example depth stop. In this example, sensor support body 102 defines a first depth stop 244 that is a region of increased material thickness relative to the distally adjacent first joint insertion portion 108. Sensor support body 102 also defines a second depth stop 246 that is a region of increased material thickness relative to the distally adjacent second joint insertion portion 112. In addition to or in lieu of configuring sensor support body 102 with a depth stop, a sensor cover attachable to the sensor support body may include a depth stop. With reference to FIG. 11B, for example, sensor cover 104B is illustrated as defining a depth stop 247 that is a region of increased material thickness relative to the distally adjacent region of the sensor cover intended to be inserted into the tibiofemoral joint. As illustrated, the depth stops are configured with a triangular or chevron shape having an apex that can contact the bone face, providing a rotation point about which the system can be rotated relative to the bone contacting the apex. Other depth stop shapes can be used in other configurations.

In use, a clinician can insert intraoperative surgical system 100 into the tibiofemoral joint until a depth stop associated with the surgical system contacts femur 12 and/or tibia 14 (and/or adjacent soft tissue), limiting the surgical system from being inserted further posterior into the joint space. The position of the one or more depth stops along the length of the intraoperative surgical system may be substantially the same (e.g., between different configurations of the system utilizing different sensor covers as part of the system of interchangeable sensor covers). This can provide consistent, repeatable repositioning of the one or more force sensors 106 carried by the intraoperative surgical system into the tibiofemoral joint space.

In addition to or in lieu of configuring intraoperative surgical system 100 with a depth stop to control positioning of the surgical system and the anterior to posterior direction, the surgical system may include one or more guide features that control positioning of the intraoperative surgical system in a medial to lateral direction. For example, the intraoperative surgical system may include a projection or other guide feature on the medial side of the joint insertion block and/or on the lateral side of the joint insertion block to limit medial to lateral movement of the joint insertion block in the tibiofemoral joint space. This can help control consistent positioning of the surgical system in the joint space in a medial to lateral direction.

In some examples, intraoperative surgical system 100 may include one or more alignment features that the surgeon can use to make one or more corresponding alignment indications on femur 12 and/or tibia 14. The one or more alignment indications can indicate where the joint insertion portion or block of the surgical system, and correspondingly the one or more force sensors associated therewith, were positioned in the joint space during measurement. After removing intraoperative surgical system 100 from the joint space, the clinician can subsequently position a prosthetic component using one or more alignment indications made on the tibia and/or femur. For example, the clinician may position tibial prosthetic component 62 (FIG. 3) to be aligned with alignment indications made on the tibia (e.g., and thereafter affix the tibial prosthetic component to the resected tibia bone). By utilizing the one or more alignment features of the surgical system to guide subsequent alignment and positioning of one or more prosthetic components in the joint space, the clinician can help ensure that the resulting forces across the joint are consistent with the planned or target forces expected by the surgeon based on the prior force measurements made using the surgical system. This can help eliminate force discrepancies caused by positional changes between where force measurements were initially made and where one or more prosthetic components were subsequently positioned during the surgical procedure.

The one or more alignment features provided by intraoperative surgical system 100 can be indicia defined on the surgical system (e.g., lines or other markings) on a surface of the surgical system. Additionally or alternatively, the one or more alignment features provided by intraoperative surgical system 100 can be a physical offset defined on the surgical system, a discontinuity in the material structure of the surgical system, and/or other surface that can guide an instrument to make an alignment indication on femur 12 and/or tibia 14.

Independent of the specific configuration of the one or more alignment features, a surgeon may guide an instrument using the one or more alignment features to mark femur 12 and/or tibia 14 for subsequent positioning and placement of a prosthetic component. Example instruments that may be used to physically mark femur 12 and/or tibia 14 include a saw blade, a scalpel, a bovie pen, and/or other sharpened instrument that can make a score line on the bone. Alternatively, the instrument may be a writing instrument with a transfer medium, such as methylene blue dye, Bonney's blue, a felt tip skin marker, a pencil, and/or other writing instrument that can deposit a colored medium on the bone. The clinician can guide the instrument along an alignment feature (e.g., parallel to the alignment feature, co-linear with the alignment feature, transverse to the alignment feature) to mark the bone at a location indicated by the alignment feature.

FIG. 5C is a top view of sensor support body 102 illustrating an example configuration of alignment features that may be provided by intraoperative surgical system 100. In the illustrated arrangement, sensor support body 102 includes a first alignment feature 246 on a first side of the joint insertion portion of the sensor support body and a second alignment feature 248 on a second side of the joint insertion portion of the sensor support body. Each alignment feature 246, 248 is illustrated as a notch formed at the proximal end of the joint insertion portion of the sensor support body. The two alignment features are positioned spaced apart from each other across the width of the joint insertion portion and provide medial and lateral alignment markings for the tibiofemoral joint. For example, the clinician may mark tibia 14 with a first alignment indication using first alignment feature 246 and may also mark the tibia with a second alignment indication using the second alignment feature 248.

The clinician may make the markings at any suitable point in the surgical process, such as after resecting both femur 12 and tibia 14 and/or optionally installing a prosthetic component of a resected bone. For example, the clinician resected both femur 12 and tibia 14 and inserted intraoperative surgical system 100 in the tibiofemoral joint space (e.g., without a prosthetic component attached to tibia 14 and with or without a prosthetic component attached to femur 12). Before, after, and/or concurrent with making a load measurement across the tibiofemoral joint space, the clinician may make alignment indications using first and/or second alignment features 246, 248. The clinician may subsequently install a prosthetic component, such as tibial prosthetic component 62 by aligning the component (e.g., medial and lateral side edges of the component and/or other features of the component) with the alignment indications made on the bone. This can control the positioning of the prosthetic component in the medial to lateral direction prior to and/or when fixing the component to the resected bone. While the foregoing example as described one or more alignment features defined by sensor support body 102 and providing an alignment indication on tibia 14, it should be appreciated that the one or more alignment features may additionally or alternatively be defined by sensor cover 104 and/or other features of the intraoperative surgical system and/or an align indication may be made on femur 12.

Intraoperative surgical system 100 includes one or more force sensors 106 configured to measure a force across the tibiofemoral joint space. The one or more force sensors can be carried by sensor support body 102, e.g., between the sensor support body and overlying sensor cover to define a joint insertion block. The joint insertion block can be positioned in the tibiofemoral joint space with the one or more force sensors 106 in the joint insertion block positioned in the tibiofemoral joint space between the distal head of femur 12 and the proximal head of tibia 14. The one or more force sensors can measure the force(s) across the joint space, such as forces generated by the ligaments connecting femur 12 to tibia 14, such as medial collateral ligament 32, lateral collateral ligament 36, and/or posterior cruciate ligament 34.

While intraoperative surgical system 100 may utilize a single force sensor 106 to measure force at a single location across the joint (e.g., substantially centered across the joint), other implementations may utilize multiple force sensors arrayed in a medial to lateral direction and/or anterior to posterior direction across the joint space. This can provide force measurements at multiple locations across the joint space, providing an indication of both a magnitude of force across the joint space (e.g., in the sagittal plane) as well as a distribution of force in the medial to lateral direction and/or anterior to posterior direction (e.g., in the transverse plane).

Figure 13:
FIG. 13 is an illustration of an example force measurement circuit that includes one or more force sensors for use in an intraoperative surgical system.

FIG. 13 is an illustration of an example force measurement circuit 250 that includes one or more force sensors 106 for use in intraoperative surgical system 100. Circuit 250 includes one or more force sensors 106 electrically and mechanically interconnected together. In the illustrated example, force measurement circuit 250 includes four force sensors 106A-106D, although may include fewer or more force sensors in different configurations. In particular, force measurement circuit 250 is illustrated as including a medial anterior force sensor 106A, a medial posterior force sensor 106B, a lateral anterior force sensor 106C, and a lateral posterior force sensor 106D.

After being inserted into the tibiofemoral joint space, medial force sensors 106A, 106B can be positioned in the medial compartment of the knee joint and lateral force sensors 106C, 106D can be positioned in the lateral compartment of the knee joint. For example, medial anterior force sensor 106A can be positioned in an anterior portion (e.g., half) of the medial compartment and medial posterior force sensor 106B can be positioned in a posterior portion (e.g., half) of the medial compartment of the tibiofemoral joint. Similarly, lateral anterior force sensor 106C can be positioned in the anterior portion (e.g., half) of the lateral compartment and lateral posterior force sensor 106D can be positioned in the posterior portion (e.g., half) of the lateral compartment of the tibiofemoral joint. This can provide a force sensor array to measure forces across the tibiofemoral joint on both medial and lateral sides of the joint as well as both anterior and posterior portions of the medial and lateral sides.

Force measurement circuit 250 may include more force sensors 106 to provide a more granular mapping or array of force measurements across the joint. Alternatively, force measurement circuit 250 may be implemented with fewer force sensors 106, e.g., the length of the cost and complexity of the circuit. In some such implementations, force measurement circuit 250 may include at least one medial force sensor and at least one lateral force sensor, each of which may be positioned at a desired location in the anterior to posterior direction (e.g., substantially centered in the anterior to posterior direction). Additionally or alternatively, force measurement circuit may include at least one anterior force sensor and at least one posterior force sensor, each of which may be positioned at a desired location in the medial to lateral direction (e.g., substantially centered in the medial to lateral direction).

Each feature described as a force sensor 106 can be implemented using any type of sensor capable of detecting and acquiring data indicative of force applied across the tibiofemoral joint. Example sensors that may be used as force sensor 106 include, for example, a piezoelectric sensor, a strain gauge, a transducer, a load cell, a capacitive sensor or the like. Force sensor 106 can generate a signal that varies depending on the magnitude of force applied to the force sensor, allowing measurement and quantification of the magnitude of force measured across the joint.

Although force measurement circuit 250 may be implemented in a variety of ways, in some examples such as that illustrated on FIG. 13, the force measurement circuit is implemented as a flex-circuit that includes conductive traces on and/or in a flexible substrate. For example, the one or more force sensors 106 can be mounted on and/or integrated in a flexible plastic substrate, such as polyimide, polyamide, polyether ether ketone, polyester, polyethylene terephthalate, or the like. The flex-circuit may be sufficiently flexible to conform to a desired non-planar shape and/or flex during use. Force measurement circuit 250 may be a thin circuit structure for positioning between sensor support body 102 and a sensor cover. For example, force measurement circuit 250 may have a maximum thickness over the region of the circuit configured to be positioned in the tibiofemoral joint of less than 2 mm, such as less than 1.5 mm, less than 1.0 mm, or less than 0.5 mm. For example, force measurement circuit 250 may have a maximum thickness over the region of the circuit configured to be positioned in the tibiofemoral joint ranging from 0.2 mm to 0.8 mm, such as from 0.4 mm to 0.7 mm, or from 0.5 mm to 0.6 mm.

In practice, force measurement circuit 250 may be a comparatively inexpensive component that can be disposed after each surgical procedure. For example, sensor support body 102, one or more sensor covers 104/200, and/or electronics housing 110 may be configured as reusable components that can be cleaned and sterilized between procedures. Force measurement circuit 250 may be used during a single surgical procedure, by contrast, and disposed after the surgical procedure with a new force measurement circuit 250 cured and used for subsequent surgical procedure.

Force measurement circuit 250 can have a variety of features and configurations to facilitate mechanical and/or electrical connections using the circuit in intraoperative surgical system 100. For example, force measurement circuit 250 may define a joint insertion region 252 containing one or more electrically and mechanically interconnected force sensors 106. Joint insertion region 252 can be configured (e.g., sized and/or shaped) to be positioned in the tibiofemoral joint space between sensor support body 102 and a sensor cover. Force measurement circuit 250 may also include a connector region 254 extending lengthwise (in the Y-direction) proximally from joint insertion region 252. Connector region 254 may include an electrical connector 202 on a proximal end. Electrical connector 202 can be used to electrically connect force measurement circuit 250 to electronics housing 110.

In the illustrated configuration, joint insertion region 252 of force measurement circuit 250 includes a first branch 256 (e.g., medial branch) mechanically and/or electrically connecting medial anterior force sensor 106A and medial posterior force sensor 106B. Joint insertion region 252 also includes a second branch 258 (e.g., lateral branch) mechanically and/or electrically connecting lateral anterior force sensor 106C and lateral posterior force sensor 106D. A distal interconnect 260 extends between first branch 256 and second branch 258 bounding a void space 262.

In the illustrated configuration, a first side connection aperture 264 (e.g., medial aperture) extending through the thickness of circuit 250 is positioned between connecting medial anterior force sensor 106A and medial posterior force sensor 106B. In this example, a second side connection aperture 266 (e.g., lateral aperture) extending through the thickness of circuit 250 is positioned between lateral anterior force sensor 106C and lateral posterior force sensor 106. First side connection aperture 264 and/or second side connection aperture 266 may provide openings through which a connector system connecting sensor support body 102 to a sensor cover may be engaged. For example, when forming a connection between the sensor support body and sensor cover within the joint insertion region, a connector of sensor support body can be positioned under one or both of first side connection aperture 264 and/or second side connection aperture 266, and a complementary connector of a sensor cover positioned over one or both apertures. The connector and complementary connector can be engaged together through one or both connection apertures.

Force measurement circuit 250 in the example of FIG. 13 also includes connector region 254 extending proximally away from the one or more force sensors for connecting with electronics housing 110. In the illustrated arrangement, first branch 256 and second branch 258 of joint insertion region 252 joined together to form a single strand extending from joint insertion region 252 on a distal end to electrical connector 202 on a proximal end.

Electrical connector 202 may be any type of electrical connector suitable for electrically connecting force measurement circuit 250 to electronics housing 110. In some examples, electrical connector 202 is an edge connector. When so configured, the edge connector may include a printed circuit board (PCB) having traces leading to the edge of the board that are intended to plug into a matching socket. The comparatively rigid printed circuit board can be mechanically and electrically connected to the remainder of the flex circuit. Electronics housing 110 can have a complementary electrical connector, which is illustrated on FIG. 6 as complementary electrical connector 270. When electrical connector 202 is implemented as an edge connector, complementary electrical connector 270 may be implemented as an edge connector socket configured to engage with the edge connector 202.

In some implementations, electrical connector region 254 and/or electrical connector 202 of force measurement circuit 250 defines one or more apertures extending through the thickness of the circuit. The one or more openings can provide connection locations through which one or more connectors can be engaged. For example, force measurement circuit 250 can define an aperture 272 configured (e.g., sized and/or shaped) to receive projection 188 therethrough for connecting sensor cover 104 to sensor support body 102 via receiving aperture 186 in the sensor support body. In the illustrated arrangement, aperture 272 is positioned at an intersection of the flex circuit and rigid electrical connector, with each bounding a portion of the space forming aperture 272.

Additionally or alternatively, force measurement circuit 250 may define at least one aperture 204 through which at least one projection 206 extending from sensor cover 200 can be inserted and/or at least one aperture 274 through which at least one projection extending from electronics housing 110 can be inserted. For example, with reference to FIG. 6, electronics housing 110 may include one or more projections 276 (e.g., extending upwardly) they can be received in corresponding apertures 274. When so configured, electrical connector 202 can be engaged with electronics housing 110 via apertures and projections 274, 276 on one side and via apertures and projections 204, 206 on an opposite side.

In operation, the one or more force sensors 106 can generate information indicative of the amount and/or distribution of force across the tibiofemoral joint. The information can be processed and communicated (e.g., displayed) to the surgeon performing the joint replacement procedure to help guide subsequent steps and decision making during the procedure and/or validate the effectiveness of the surgical procedure. Accordingly, intraoperative surgical system 100 may include and/or communicate with one or more computing devices to process and/or display information associated with measurements made by the surgical system.

Figure 14:
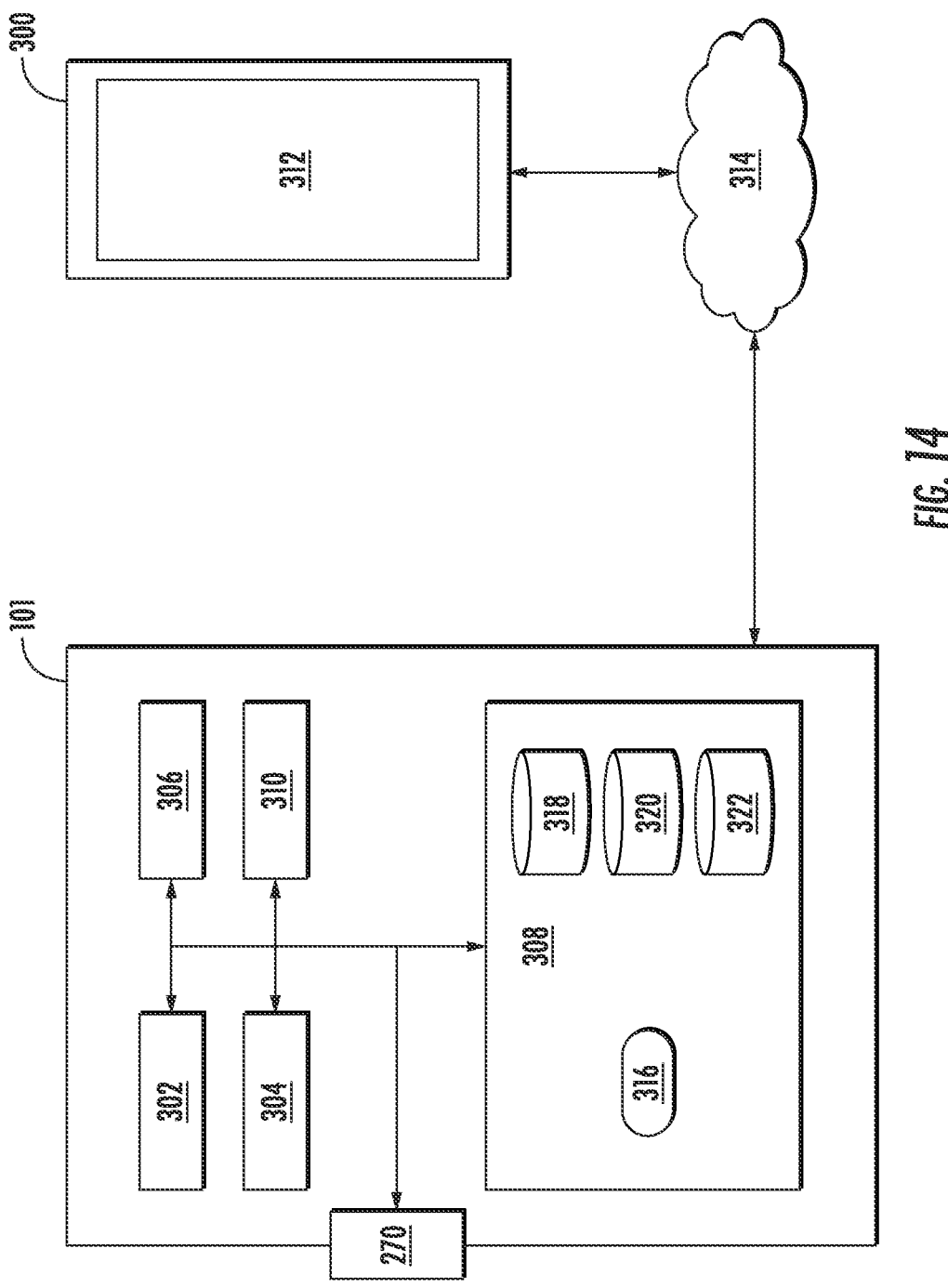
FIG. 14 is a conceptual diagram illustrating an example computing system and environment for an intraoperative sensor system.

FIG. 14 is a conceptual diagram illustrating an example computing system and environment for intraoperative sensor system 100. FIG. 14 includes a block illustration of example components that may be included in electronics housing 110 along with an example external device 300 that may be communicatively coupled to electronics housing 110. In the example of FIG. 14, electronics housing 110 of intraoperative sensor system 100 is illustrated as including one or more processors 302, one or more communication units 304, one or more storage devices 306, and one or more power sources 308. In some examples, electronics housing 110 also contains one or more position sensors 310. Communication channels may interconnect components in electronics housing 110 for inter-component communications (physically, communicatively, and/or operatively). In some examples, the communication channels may include a system bus, a network connection, an inter-process communication data structure, or any other method for communicating data.

External device 300 in FIG. 14 represents any suitable mobile or stationary remote computing system, such as one or more desktop computers, laptop computers, mobile computers (e.g., mobile phone or smart phone), cloud computing systems, etc. capable of sending and receiving information to electronics housing 110. External device 300 may include one or more processors and storage units operable to perform the functions attributable to external device 300 herein. While external device 300 may typically be physically separate from sensor support body 102 and electronics housing 110, in other implementations, the functionality of external device 300 may be integrated into sensor support body 102 and/or other portion of the system connected therewith.

External device 300 can include a user interface 312. User interface 312 of external device 300 may function as an input device and/or as an output device. User interface 312 may be implemented using various technologies. For instance, user interface 312 may function as an input device using a microphone and as an output device using a speaker to provide an audio-based user interface. User interface 312 may function as an input device using a presence-sensitive input display, such as a resistive touchscreen, a surface acoustic wave touchscreen, a capacitive touchscreen, a projective capacitance touchscreen, a pressure sensitive screen, an acoustic pulse recognition touchscreen, or another presence-sensitive display technology. User interface 312 may function as an output (e.g., display) device using any one or more display devices, such as a liquid crystal display (LCD), dot matrix display, light emitting diode (LED) display, organic light-emitting diode (OLED) display, e-ink, or similar monochrome or color display capable of outputting visible information to the user of intraoperative system 100.

User interface 312 may receive indications of tactile input by detecting one or more gestures from a user of intraoperative system 100 (e.g., the user touching or pointing to one or more locations of user interface 312 with a finger or a stylus pen). User interface 312 may present output to a user, for instance at a display. User interface 312 may present the output as a graphical user interface. In some examples, user interface 312 may present various user interfaces of applications executing at or accessible by external device 300 (e.g., an electronic message application, an Internet browser application, etc.).

In some examples, external device 300 represents a cloud computing system that provides one or more services through a network 314. One or more computing devices associated with electronics housing 110 may access the one or more services provided by the cloud using external device 300. For example, intraoperative surgical system 100 may store and/or access data in the cloud using network 314 and external device 300. In some examples, some or all the functionality of external device 300 exists in a mobile computing platform, such as a mobile phone, tablet computer, etc. that may or may not be at the same geographical location (e.g., same operating room) as the portion of intraoperative surgical system 100 insertable into the tibiofemoral joint space. For instance, some or all the functionality of external device 300 may, in some examples, reside in and be executed from within a mobile computing device that is in the same environment as electronics housing 110 and the portion of intraoperative surgical system 100 insertable into the tibiofemoral joint space.

One or more communication units 304 associated with electronics housing 110 may communicate with external devices (e.g., external device 300) via one or more networks 314 by transmitting and/or receiving network signals on the one or more networks. For example, information associated with the one or more force sensors 106 and/or one or more position sensors 310 of intraoperative surgical system 100 may use communication units 304 to send and receive data to and from external device 300 in FIG. 14. Communication units 304 can transmit and/or receive radio signals on a radio network such as a cellular radio network. Likewise, communication units 304 may transmit and/or receive satellite signals on a satellite network such as a global positioning system (GPS) network. Examples of communication unit 304 include a network interface card (e.g., such as an Ethernet card), an optical transceiver, a radio frequency transceiver, a GPS receiver, or any other type of device that can send and/or receive information. Other examples of communication units 304 may include short wave radios, cellular data radios, wireless Ethernet network radios, as well as universal serial bus (USB) controllers.

For instance, examples of local wireless communication techniques that may be employed to facilitate communication between communication units 304 and external device 300 include RF communication according to the 802.11 or Bluetooth® specification sets, infrared communication, e.g., according to the IrDA standard, or other standard or proprietary wireless protocols. For example, communication may occur via near field communication, cellular communication, Wi-Fi radio, and/or other wireless communication technique. In other examples, electronics housing 110 is connected to external device 300 via a wired connection.

One or more storage devices 306 within electronics housing 110 may store information generated by intraoperative surgical system 100, such as information indicative of force measurements made by the one or more force sensors 106 and/or one or more position sensors 310. Such data may be accessed by other modules and features of intraoperative surgical system 100 during execution of one or more modules and/or programs. In some examples, storage devices 306 is or incudes a temporary memory configured for short-term storage of information as volatile memory and therefore not retain stored contents if powered off. Examples of volatile memories include random access memories (RAM), dynamic random access memories (DRAM), static random access memories (SRAM), and other forms of volatile memories known in the art. Storage devices 306, in some examples, also include one or more computer-readable storage media. Storage devices 306 may be configured to store larger amounts of information than volatile memory. Storage devices 306 may further be configured for long-term storage of information as non-volatile memory space and retain information after power on/off cycles. Examples of non-volatile memories include magnetic hard discs, optical discs, floppy discs, flash memories, or forms of electrically programmable memories (EPROM) or electrically erasable and programmable (EEPROM) memories. Storage devices 306 may store program instructions and/or data for performing the features and functions described herein as being performed by any module, device, and/or system, including one or more processors 302.

Storage devices 306 in the example of FIG. 14 are illustrated as including a load balance simulation module 316 and one or more data stores, which is illustrated as including a load measurement data store 318, a position measurement data store 320, and a simulation data store 322. Load measurement data store 318 may receive and store data indicative of force measurements made by force sensors 106. Position measurement data store 320 may receive and store data indicative of one or more position measurements made by position sensor 310. Load balance simulation module 316 may respond to a request simulating a change to one or more characteristics of the tibiofemoral joint space and generate a simulated load balance across the tibiofemoral joint and/or simulated positional information associated with the tibiofemoral joint in response to the simulated change.

For example, load balance simulation module 316 may respond to requests simulating one or more changes to the extent and/or profile (e.g., varus/valgus angle) of bone resected from femur 12 and/or tibia 14. Load balance simulation module 316 may additionally or alternatively respond to requests simulating one or more changes to one or more prosthetic components 60, 62, and/or 64 to be positioned in the tibiofemoral joint space, such as increase or decrease in the thickness of a tibial insert. Load balance simulation module 316 may receive one or more simulation requests from external device 300 in response to a surgeon input to external device 300 via user interface 312. Load balance simulation module 316 may simulate load force and/or positional changes to the tibiofemoral joint in response to projected changes entered via user interface 312 by the surgeon with reference. Load balance simulation model 316 may reference simulation data store 322 to determine how one or more simulated changes to the tibiofemoral joint space may affect forces exhibited across the tibiofemoral joint space as measured by force sensors 106 and/or may affect the varus-valgus angle of the tibiofemoral joint and/or tilt angle of the tibiofemoral joint as measured by position sensor 310. Load balance simulation module 316 may respond to the request by sending information to external device 300.

In general, the one or more force sensors 106 of intraoperative surgical system 100 may output, for transmission to external device 300, information indicative of one or more load forces measured across the tibiofemoral joint. The one or more position sensors 310 of intraoperative surgical system 100 may also output, for transmission to external device 300, information indicative of the positional orientation of the distal head of femur 12 and/or the proximal head of tibia 14. The positional orientation information may indicate the numerical (e.g., angular) extent of a medial-to-lateral sloping of the distal head of femur 12 and/or proximal head of tibia 14, which may be referred to as the varus-valgus angle. Additionally or alternatively, the positional information may indicate the numerical (e.g., angular) extends of an anterior-to-posterior sloping or tilt of one or both bones, such as the tilt of the tibial plateau. An output function of the user interface 312 can provide data indicative of force and/or position information measured across the tibiofemoral joint.

The clinician can interact with an input function of user interface 312 to input one or more changes that may be made by the clinician to the tibiofemoral joint space, and the load balance simulation module 316 can determine the resultant force that will be measured across the joint space after making such changes and/or positional orientation information that will be measured after making such changes. Load balance simulation model 316 can analyze one or more simulated changes received from external device 300 with reference to simulation data store 322. Simulation data store 322 may contain data relating different load forces across the tibiofemoral joint to different bone resection and/or prosthetic component configurations. Simulation data store 322 may also contain data relating different positional orientations for the distal head of femur 12 and proximal head of tibia 14 to different bone resection and/or prosthetic component configurations.

Load balance simulation model 316 can modify force and/or positional orientation measurements made with respect to the tibiofemoral joint based on the type and extent of changes simulated by the clinician with reference to simulation data store 322 to determine resultant simulated force and/or positional orientation measurements that are expected to result if the changes are physically implemented by the clinician. The resultant simulated data can be communicated to external device 300 and displayed on user interface 312. If the simulated data accords with the clinician load balance and/or positional orientation objectives, the clinician may proceed to surgically implement the one or more changes previously simulated. If the simulated data is outside of the clinician's target load balance and/or positional orientation objectives, the clinician may input one or more alternative changes and load balance simulation model 316 can make new determinations.

Load balance simulation model 316 may perform operations described using software, hardware, firmware, or a mixture of hardware, software, and firmware residing in and/or executing at electronics housing 110. Additionally or alternatively, load balance simulation model 316 may be executed with one or more processors and/or on one or more devices separate from electronics housing 110, such as one or more processors residing in an/or executing at external device 300 and/or a remote computing device (e.g., cloud computing platform). In some examples, load balance simulation model 316 may be executed as a virtual machine executing on underlying hardware. Load balance simulation model 316 may execute as a service of an operating system or computing platform. Load balance simulation model 316 may execute as one or more executable programs at an application layer of a computing platform.

Features described as data stores can represent any suitable storage medium for storing actual, modeled, or otherwise derived data. Load balance simulation module 316 may access one or more data stores for determining simulated force and/or positional orientation values based on actual measure force and/or positional orientation values and one or more simulation instructions indicating one or more changes to the tibiofemoral joint space received from the clinician via external device 300. Data stores may contain lookup tables, databases, charts, graphs, functions, equations, and the like that load balance simulation module 316 may access to evaluate data generated by one or more force sensors 106 and/or one or more position sensors 310. Any of the one or more data stores may reside at or in electronics housing 110 or may be partially or fully remote from electronics housing 110 and communicatively coupled to one or more computing devices that have a one or more processors performing the functions described herein.

The data stored in simulation data store 322 may be generated from and/or based on one or more data development sessions in which a tibiofemoral joint is modified, e.g., by resecting different amounts of femur 12 and/or tibia 14, by resecting femur 12 and/or tibia 14 at different varus-valgus angles, and/or by inserting different size prosthetic components in the tibiofemoral joint space, in measuring the resultant loads across the joint space using one or more force sensors 106 and/or different positional orientations of the bones and/or joint using one or more position sensors 310. Additionally or alternatively, simulation data store 322 may be generated from and/or based on literature data relating different load forces across the tibiofemoral joint and/or different positional orientations of the distal head of femur 12 and/or proximal head of tibia 14 to different bone resection characteristics of femur 12 and tibia 14 (e.g., extent of resection and/or angles of resection) and/or different prosthetic component sizes.

One or more processors 302 may implement functionality and/or execute instructions within electronics housing 110. For example, processors 302 may receive and execute instructions stored by storage devices 306 that execute the functionality of load balance simulation module 316. The instructions executed by processors 302 may cause electronics housing 110 to store information, within storage devices 306 during program execution.

Although shown in FIG. 14 as a separate element apart from electronics housing 110, in some examples, some or all of the functionality described as being performed at electronics housing 110 may be implemented by external device 300. For example, module 316 and data stores 318, 320, 322 may exist locally at external device 300 to receive information regarding position and/or load measurements and to perform analyses as described herein. Accordingly, while certain functionalities are described herein as being performed at electronics housing 110, some or all of the functionalities may be shifted from the electronics housing to external device 300 and/or yet other remote computing device without departing from the scope of disclosure.

When configured with one or more position sensors 310, the one or more position sensors may generate position data across one or more axes. In some examples, position sensors 310 may be implemented using a three-axis accelerometer. Additionally or alternatively, position sensor 310 may include a gyroscope and/or inertial measurement unit (IMU). The one or more position sensors 310 may provide x-, y-, and z-axes signals, such as x-, y-, and z-axes acceleration signal signals. In some configurations, the one or more position sensors 310 may be operable to measure a position of the distal head of femur 12 and/or the proximal head of tibia 14 when one or both bones are statically positioned (non-moving). In other configurations, the one or more position sensors 310 may be operable to measure a position of the distal head of femur 12 and/or the proximal head of tibia 14 when one or both bones are in motion.

Power source 308 may include one or more capacitors, batteries, or other energy storage devices. Power source 308 can deliver operating power to the components in electronics housing 110. Power source 308 may be replaceable and/or rechargeable, or may be configured as a single-use power source. In other configurations, a corded power source is provided that electrically connects components in electronics housing 110 to wall or mains power.

In some instances components described as being contained within electronics housing 110 may be contained within a plurality of housings and/or or some components may be secured partially or fully outside of an internal hermetically sealed compartment of the housing and electrically coupled to other components within a compartment of the housing as described herein. In some examples, electronics housing 110 is hermetically sealed to allow the electronics housing to be sterilized between surgical uses. For example, electronics housing 110 may be formed of two or more sections joined together with a seal or gasket above the connection perimeter of the sections that are joined together. A potting fill aperture may be provided through the electronics housing 110 to allow the potting material to be in filled in the electronics housing after assembly. For example, the electrical components to be housed in electronics housing 110 can be electrically coupled in the housing and mechanically affixed in the housing, the housing closed with a seal between different sections of the housing, and a polymeric potting material filled in the void spaces of the housing and surrounding the electronic components therein.

Figure 15:
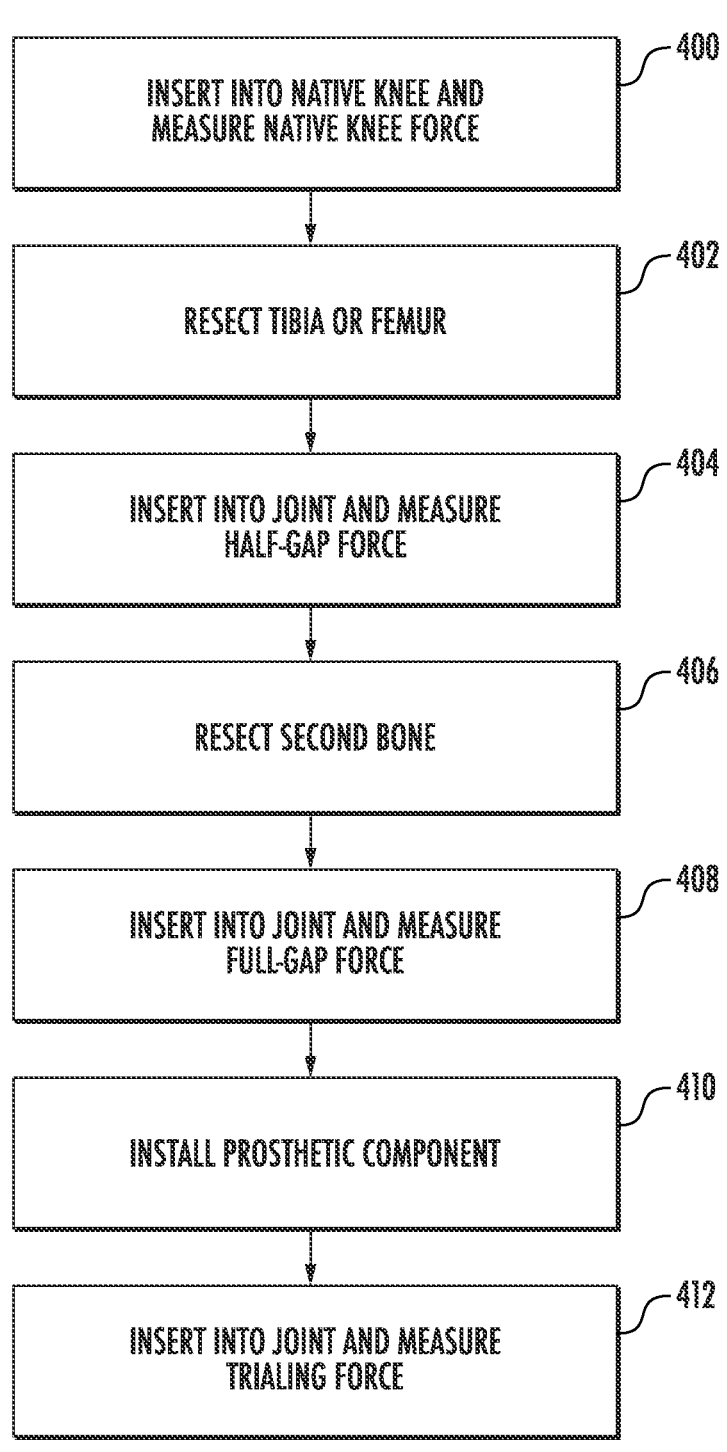
FIG. 15 is a flow diagram illustrating an example technique for making intraoperative load measurements during a knee replacement procedure using an example intraoperative surgical system according to the disclosure.
Figure 16:
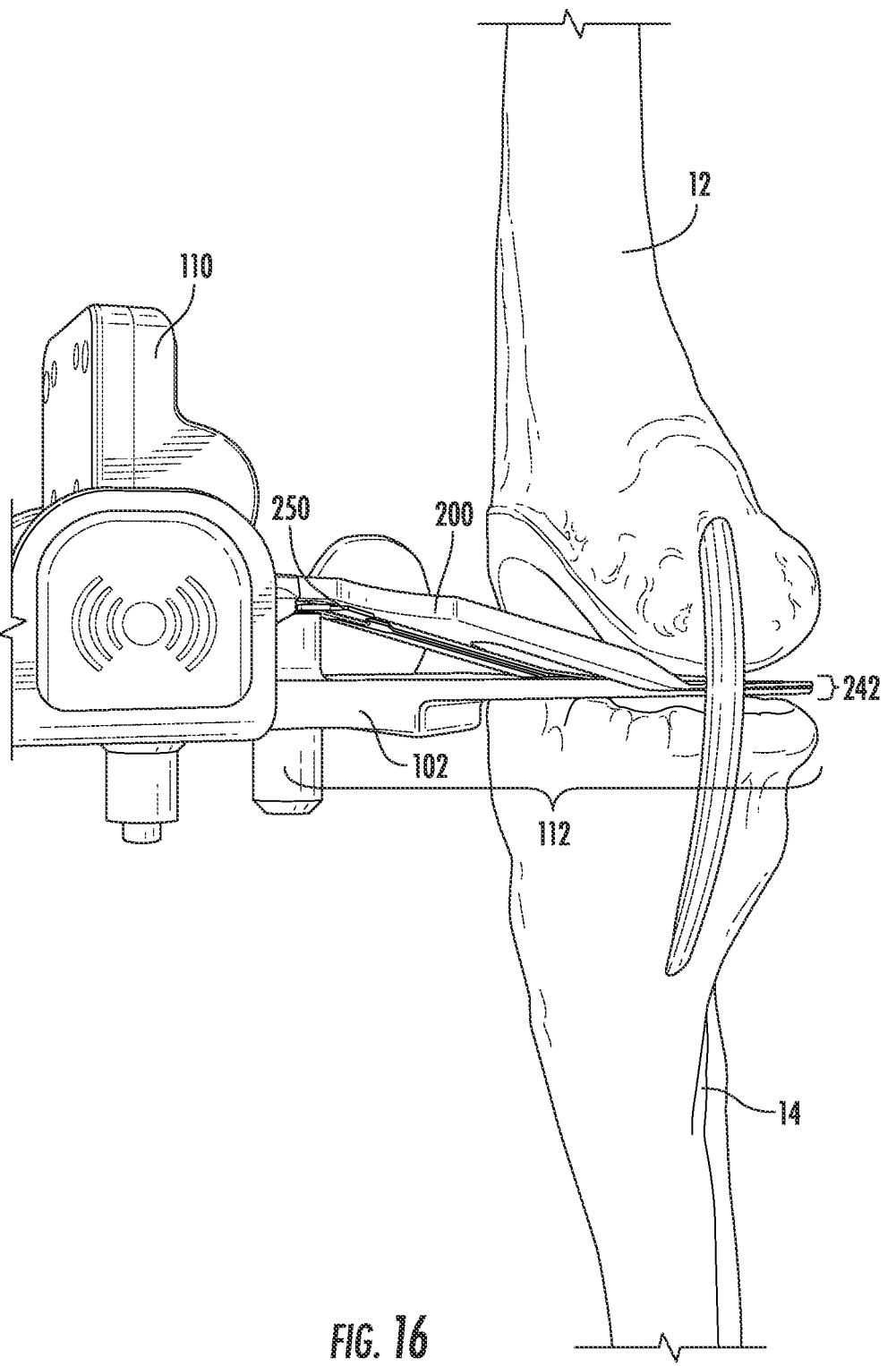
FIGS. 16-18 are illustrations of example technique steps that can be performed in conjunction with the technique of FIG. 15.

FIG. 15 is a flow diagram illustrating an example technique for making intraoperative load measurements during a knee replacement procedure using an example intraoperative surgical system according to the disclosure. The example technique of FIG. 15 will be described with respect to FIGS. 16-18 and an example configuration of intraoperative surgical system 100 but can be performed with systems having other configurations as described herein.

In the example of FIG. 15, the surgeon surgically accesses the tibiofemoral joint and inserts sensor support body 102 carrying one or more force sensors 106 into the native knee joint to make an uncut or native knee force measurement (400). For example, with reference to FIG. 16, the clinician may select a sensor cover 200 from a set of different sensor covers and position force measurement circuit 250 carrying one or more force sensors 106 on the second joint insertion portion 112 of sensor support body 102. The clinician can attach electronics housing 110 to sensor support body 102 with a complementary electrical connector on the electronics housing positioned facing second joint insertion portion 112. The clinician can electrically attach force measurement circuit 250 to electronics housing 110 by inserting an electrical connector carried on a proximal end of the force measurement circuit into the complementary electrical connector on the electronics housing.

The clinician may optionally clear out the meniscus, soft tissue, osteophytes, and/or other locking bodily matter within the tibiofemoral joint space using a saw blade or other cutting instrument. In either case, the clinician can advance the distal end of joint insertion block 242 into the tibiofemoral joint space until the one or more force sensors 106 carried by sensor support body 102 are positioned between the uncut distal head of femur 12 and the uncut proximal head of tibia 14. The one or more force sensors 106 can measure the force between the opposed bones across the tibiofemoral joint space, e.g., as femur 12 presses against a top surface of sensor cover 200 and tibia 14 presses against a bottom surface of sensor support body 102. It should be appreciated that although intraoperative surgical system 100 is generally described as being inserted with the sensor cover facing femur 12 and the sensor support body facing tibia 14, the system may be flipped so the sensor support body is on the femur side and the sensor cover is on the tibia side.

The clinician may assess loads across the tibiofemoral joint space and an extension and/or one or more flexion positions. Extension refers to a position in which the tibiofemoral joint is straight position, e.g., with the tibia moved away from the posterior side of the femur. Flexion refers to a position in which the tibiofemoral joint is bent, resulting in a non-zero degree angle between the anterior side of the tibia and the anterior side of the femur. For example, the clinician may place the leg in extension and assess a force across the tibiofemoral joint space measured by force sensors 106 with the leg in extension. The clinician may additionally or alternatively place the leg in flexion and assess the tibiofemoral joint space measured by force sensors 106 with the leg in flexion. The clinician may place the leg at 90° flexion and/or one or more other flexion angles, such as a flexion angle ranging from 15° to 60°. In some examples, the clinician interacts with user interface 312 of external device 300 to inform the system when the leg is at a desired extension and/or flexion position, allowing the system to associate force measurements made at that location with the leg position for storage in one or more data stores.

One or more processors 302 in electronics housing 110 and/or one or more other processors remote from electronics housing 110 can receive and process measurement information generated by the one or more force sensors 106 to provide an indication of measured force suitable for display on the user interface 312. For example, external device 300 may receive data indicative of force measurements made by force sensors 106 for display on user interface 312. External device 300 may display force information graphically (e.g., color coding), textually (e.g., numerically), and/or in another format discernible to the clinician. The display of external device 300 may update continuous (e.g., in real time) as force measurements made by force sensors 106 change. Alternatively, the display of external device 300 may update at discrete times as force measurements made by force sensors 106 change (e.g., in response to a user interacting with the device to request or make a discrete force measurement).

The example technique of FIG. 15 also involves resecting one but not both of femur 12 and tibia 14 (402). For example, the clinician may resect tibia 14 by cutting the proximal end of the tibia to form a cut proximal plateau.

After cutting one but not both of femur 12 and tibia 14, the example technique of FIG. 15 involves inserting sensor support body 102 carrying one or more force sensors 106 into the tibiofemoral joint to make half-gap measurement (404). For example, with reference to FIGS. 17A-C, the clinician may select a sensor cover 104B from a set of different sensor covers and position force measurement circuit 250 carrying one or more force sensors 106 on the first joint insertion portion 108 of sensor support body 102. The clinician can position electronics housing 110 on sensor support body 102 with a complementary electrical connector on the electronics housing positioned facing first joint insertion portion 108 and electrically attach the force measurement circuit to the electronics housing. In other configurations, the clinician may replace sensor cover 200 with a larger sensor cover 104B on the same joint insertion portion of sensor support body 102.

Figure 17A:
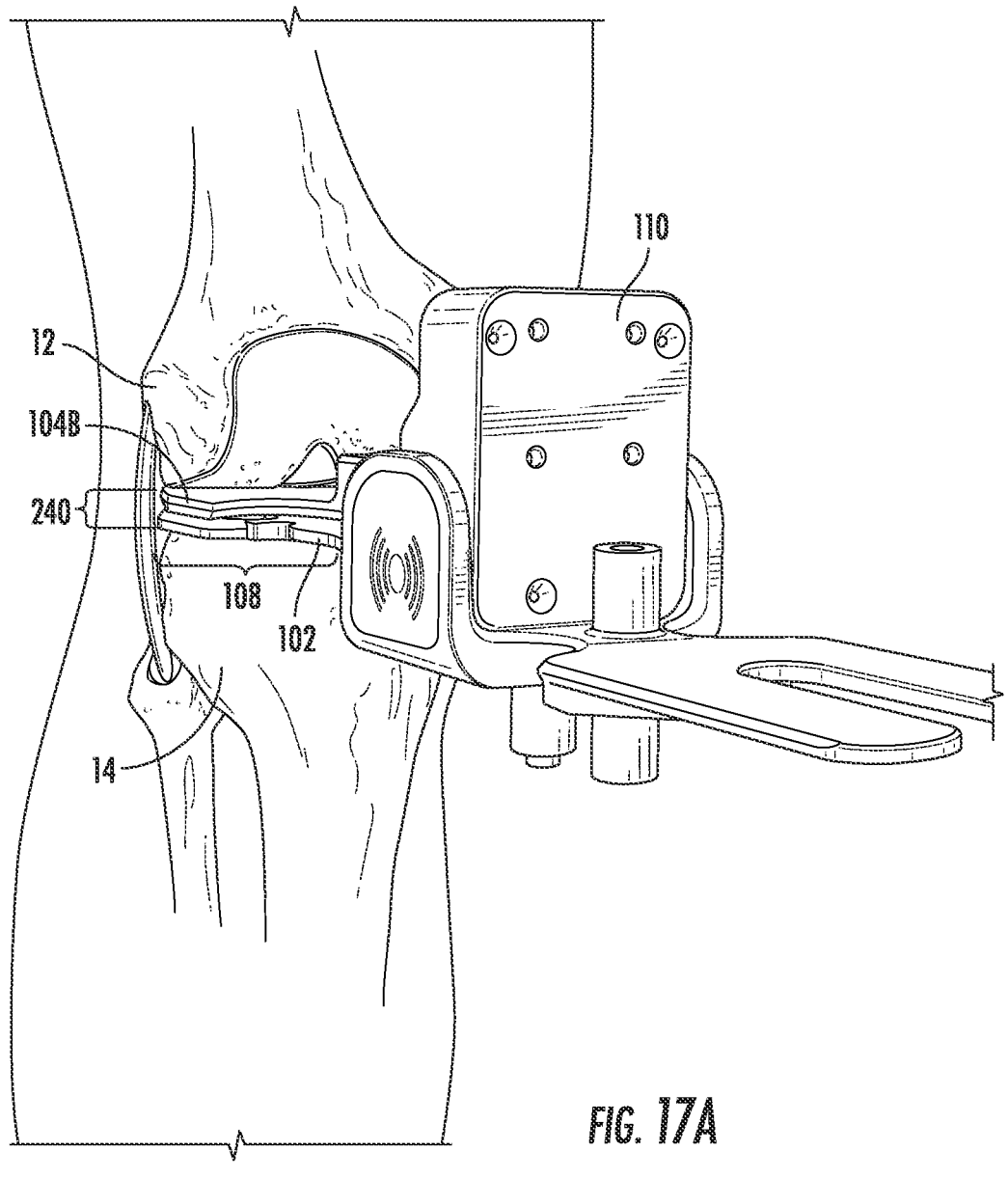
Figure 17B:
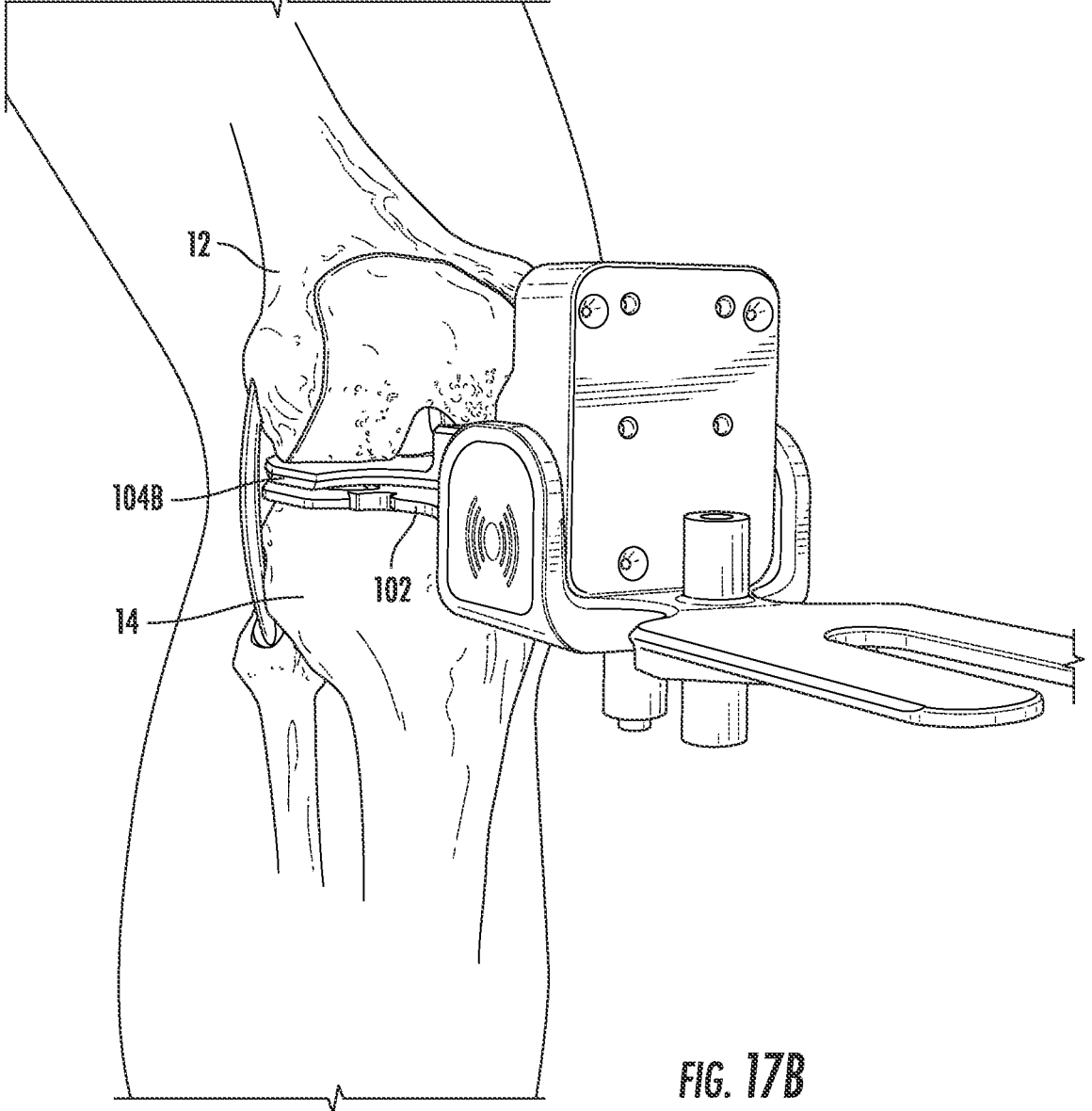
Figure 17C:
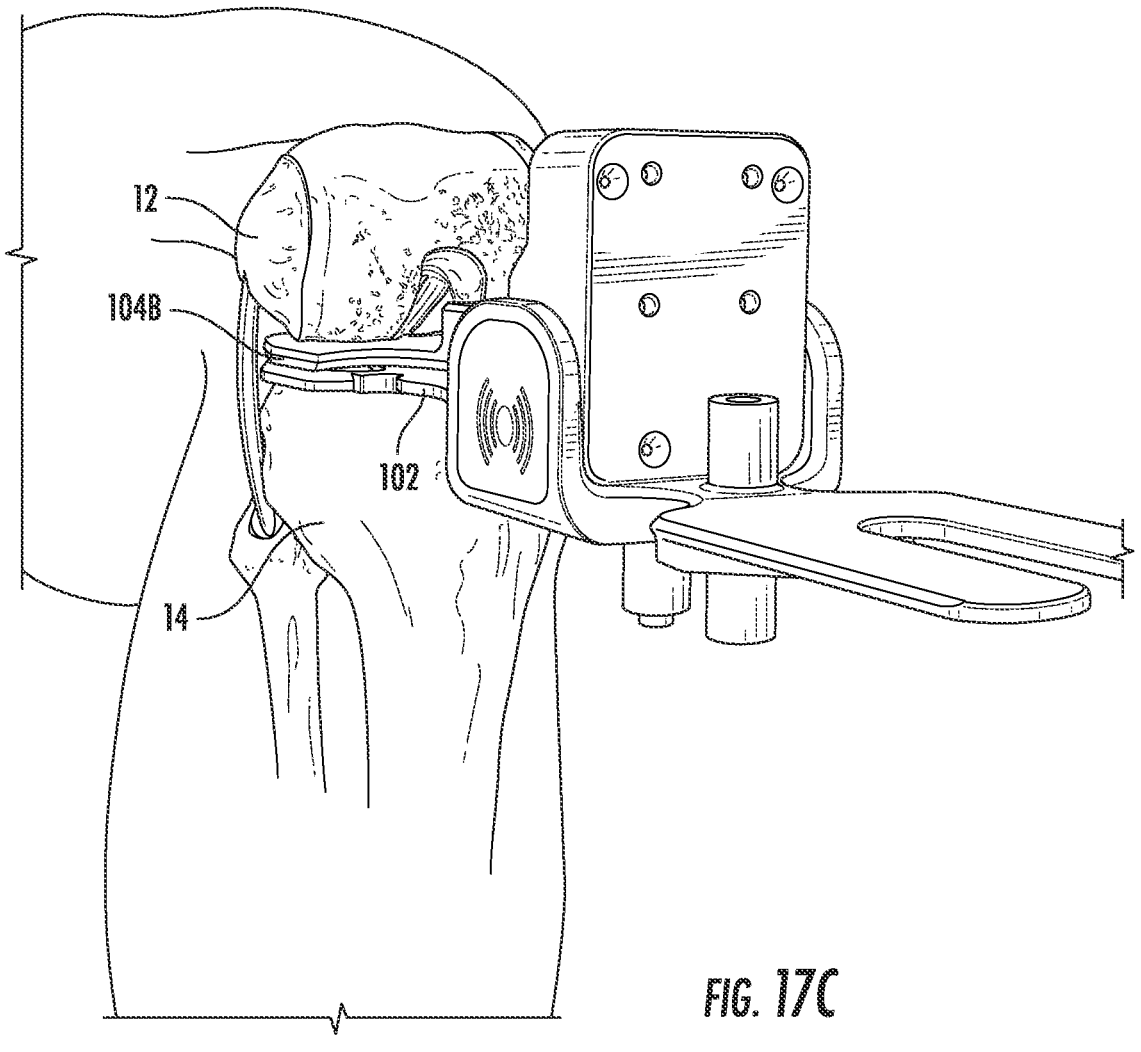
Figure 18:
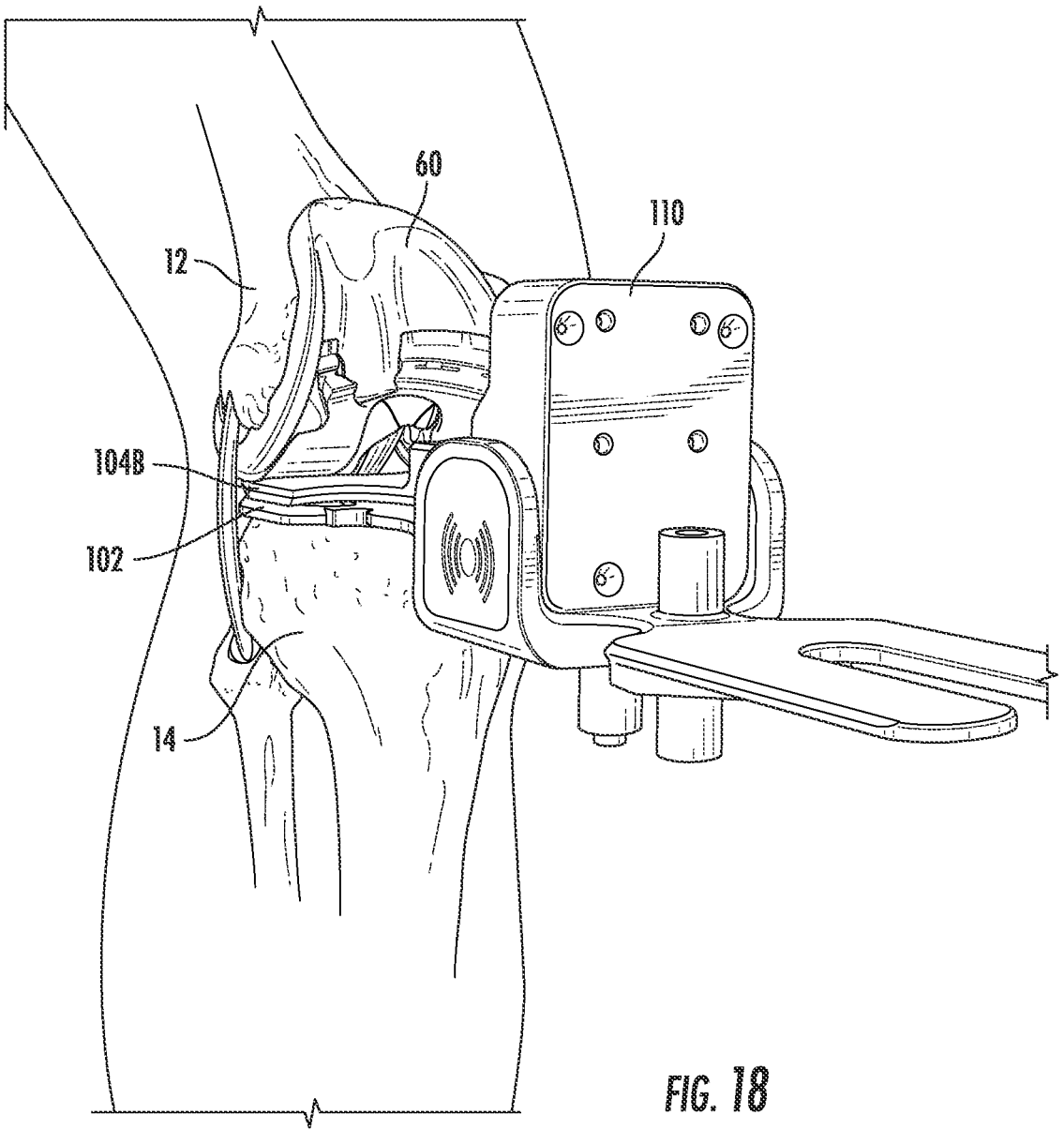

In either case, the clinician can advance the distal end of joint insertion block 240 into the tibiofemoral joint space until the one or more force sensors 106 carried by sensor support body 102 are positioned between the uncut distal head of femur 12 and the cut proximal head of tibia 14 (or vice versa). The one or more force sensors 106 can measure the force between the opposed bones across the tibiofemoral joint space, e.g., as femur 12 presses against a top surface of sensor cover 104B and tibia 14 presses against a bottom surface of sensor support body 102. The clinician may assess loads across the tibiofemoral joint space and an extension and/or one or more flexion positions, as discussed above with respect to step (400). For example, FIG. 17A illustrates intraoperative surgical system 100 positioned in the tibiofemoral joint with the leg in extension; FIG. 17B illustrates intraoperative surgical system 100 positioned in the tibiofemoral joint with the leg at a first flexion angle; and FIG. 17C illustrates intraoperative surgical system 100 positioned in the tibiofemoral joint with the leg in 90 degree flexion. The one or more processors 302 in electronics housing 110 and/or one or more other processors remote from electronics housing 110 can receive and process measurement information generated by the force sensors 106 and external device 300 may receive data indicative of force measurements made by the force sensors for display on user interface 312, as also discussed above with respect to step (400).

The example technique of FIG. 15 also involves resecting the other of femur 12 and tibia 14 (406). For example, the clinician may resect femur 12 by cutting the distal end of the femur to form a cut distal end.

After cutting the other of femur 12 and tibia 14 not previously cut, the example technique of FIG. 15 involves inserting sensor support body 102 carrying one or more force sensors 106 into the tibiofemoral joint to make full-gap measurement (408). For example, the clinician may detach sensor cover 104B from sensor support body 102 and replace the removed sensor cover with a second sensor cover

104A having a thickness greater than sensor cover 104B. The clinician can advance the distal end of joint insertion block 240 carrying sensor cover 104A into the tibiofemoral joint space until the one or more force sensors 106 carried by sensor support body 102 are positioned between the cut distal head of femur 12 and the cut proximal head of tibia 14.

The one or more force sensors 106 can measure the force between the opposed bones across the tibiofemoral joint space, e.g., as femur 12 presses against a top surface of sensor cover 104B and tibia 14 presses against a bottom surface of sensor support body 102. The clinician may assess loads across the tibiofemoral joint space in extension and/or one or more flexion positions, as discussed above with respect to step (400). In addition, the one or more processors 302 in electronics housing 110 and/or one or more other processors remote from electronics housing 110 can receive and process measurement information generated by the force sensors 106 and external device 300 may receive data indicative of force measurements made by the force sensors for display on user interface 312, as also discussed above with respect to step (400).

The example technique of FIG. 15 also involves placing a prosthetic component on one or both of femur 12 and tibia 14 (410). For example, the clinician may install a trial or permanent prosthetic component 60 on femur 12 and/or a trial or permanent prosthetic component 62 on tibia 14. In one example, the clinician installs a trial prosthetic component on femur 12 but does not install a trial prosthetic component on tibia 14 or a tibial insert into the joint.

After affixing the one or more prosthetic components, the example technique of FIG. 15 involves inserting sensor support body 102 carrying one or more force sensors 106 into the tibiofemoral joint to make a trialing measurement (412). For example, with reference to FIG. 18, the clinician may detach sensor cover 104A from sensor support body 102 and replace the removed sensor cover with a different sensor cover (e.g., sensor cover 104A, 200) having a thickness less than sensor cover 104A. The clinician can advance the distal end of joint insertion block 240 carrying sensor cover 104A into the tibiofemoral joint space until the one or more force sensors 106 carried by sensor support body 102 are positioned between the distal head of femur 12 carrying a prosthetic component and the cut proximal head of tibia 14 (or vice versa).

The one or more force sensors 106 can measure the force across the tibiofemoral joint space, e.g., as femur 12 indirectly presses against a top surface of a sensor cover and tibia 14 directly presses against a bottom surface of sensor support body 102. The clinician may assess loads across the tibiofemoral joint space in extension and/or one or more flexion positions, as discussed above with respect to step (400). In addition, the one or more processors 302 in electronics housing 110 and/or one or more other processors remote from electronics housing 110 can receive and process measurement information generated by the force sensors 106 and external device 300 may receive data indicative of force measurements made by the force sensors for display on user interface 312, as also discussed above with respect to step (400).

In each measurement step discussed above with respect to the example technique of FIG. 15, the one or more force sensors 106 carried by the intraoperative surgical system may generate force measurement data for processing by one or more processors and communication to the clinician, e.g., the user interface 312 of external device 300. Where force measurement circuit 250 includes an array of multiple force sensors, data indicative of force measurements made by each force sensor can be communicated and/or displayed to the clinician. Additionally or alternatively, force measurement data from different sensors may be processed and/or otherwise aggregated to form one or more composite force measurements that can be communicated and/or displayed to the clinician.

For example, intraoperative surgical system 100 may include at least one medial force sensor in at least one lateral force sensor. The medial force sensor can measure a medial compartment force and the lateral force sensor can measure a lateral compartment force. In some implementations, for instance, the surgical system includes at least one medial anterior force sensor and at least one medial posterior force sensor. The medial anterior force sensor can provide a medial anterior force measurement, and the medial posterior force sensor can provide a medial posterior force measurement. The system can also include at least one lateral anterior force sensor and at least one lateral posterior force sensor. The lateral anterior force sensor can provide a lateral anterior force measurement, and the lateral posterior force sensor can provide a lateral posterior force measurement. Data corresponding to any of the foregoing force measurements can be communicated to the clinician in the surgical environment, such as displayed on a display of remote device 300.

In some examples, one or more processors 302 operating in electronics housing 110 and/or one or more processors remote from electronics housing can process force measurements from different force sensors to generate composite or average force values. For example, the one or more processors may determine a single medial force value based on multiple medial force measurements, such as a mean medial average force value based on a medial anterior force measurement and a medial posterior force measurement. The one or more processors may determine a single lateral force value based on multiple lateral force measurements, such as a mean average lateral force value based on a lateral anterior force measurement and a lateral posterior force measurement.

Figure 19:
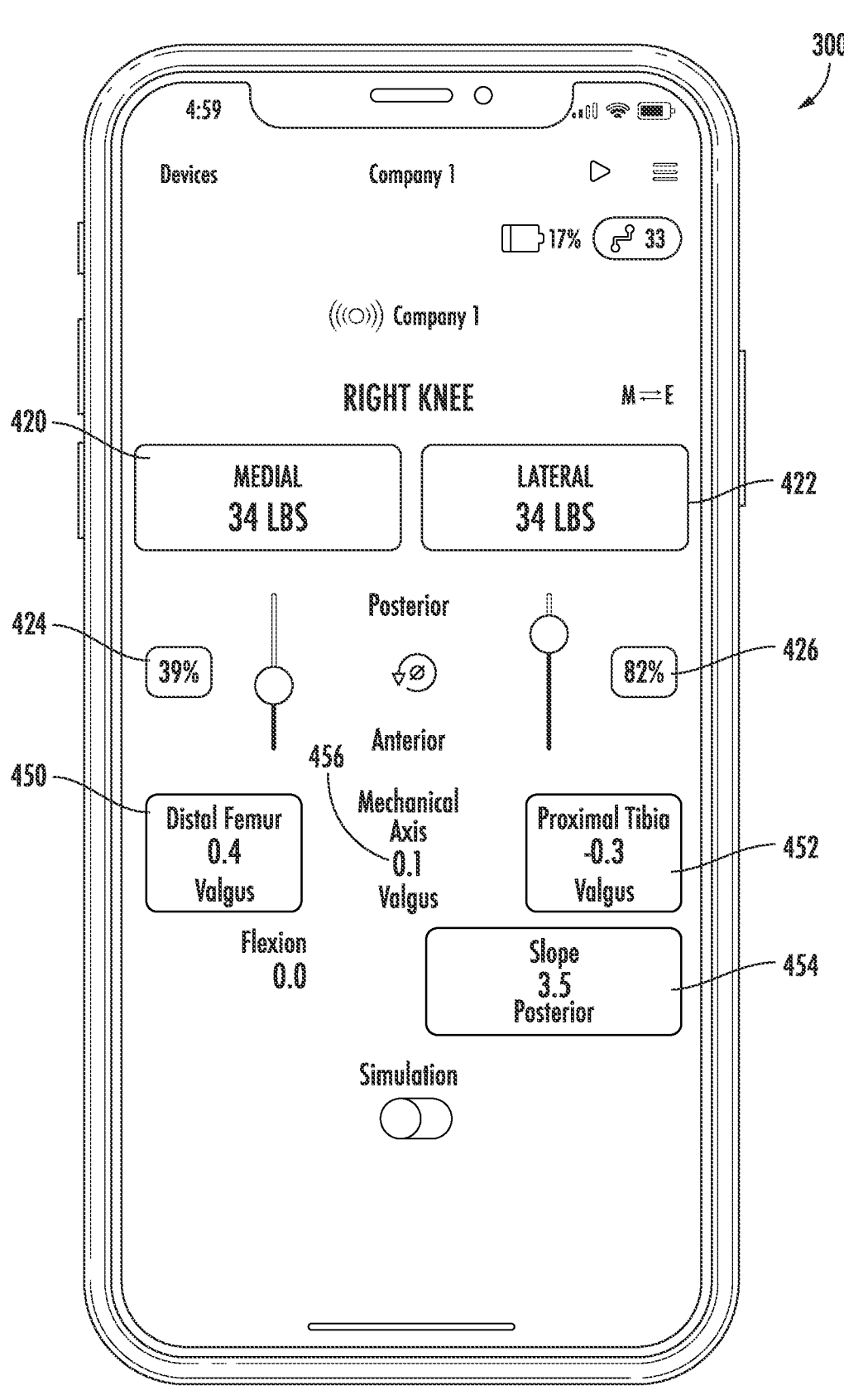
FIG. 19 is an illustration of an example user interface and display output that can be provided to a clinician on a remote device.

FIG. 19 is an illustration of an example user interface and display output that can be provided to a clinician on remote device 300. In the illustrated example, device 300 displays a numeral medial force value 420, which indicates the force measured across the medial compartment of the tibiofemoral joint. Medial force value 420 may be a composite value, such as a mean average value, determined based on multiple medial force measurements from multiple force sensors positioned across the medial compartment of the joint space.

Device 300 in FIG. 19 it is also illustrated as displaying a numerical lateral force value 422, which indicates the force measured across the lateral compartment of the tibiofemoral joint. Lateral force value 422 may be a composite value, such as a mean average value, determined based on multiple lateral force measurements for multiple force sensors positioned across the lateral compartment of the joint space.

In some examples, one or more processors 302 operating in electronics housing 110 and/or one or more processors remote from electronics housing can process force measurements from different force sensors to generate information indicative of the distribution of force across the joint space in one or more planes. For example, the one or more processors may determine a distribution of force in an anterior to posterior direction across the tibiofemoral joint space, e.g., in one or both of the medial and lateral compartments of the knee. The one or more processors may determine the distribution of force based on the magnitude of force measured by the different sensors and the relative position of the sensors in the joint space. Remote device 300 can generate and/or receive information indicative of the force distribution for display to the clinician.

For example, FIG. 19 illustrates an example displayed indication of a distribution of medial force 424 in the anterior to posterior direction of the medial compartment of the knee. FIG. 19 also illustrates an example displayed indication of a distribution of lateral force 426 in the anterior to posterior direction of the lateral compartment of the knee. In the illustrated example, the force distribution indicators provide a moving graphical object and a numerical value indicative of the force distribution in the anterior to posterior direction, scaled with 0% being completely anterior, 100% being completely posterior, and 50% being balanced in the anterior to posterior direction. Other display configurations and outputs can be utilized without departing from the scope of the disclosure.

Figure 20:
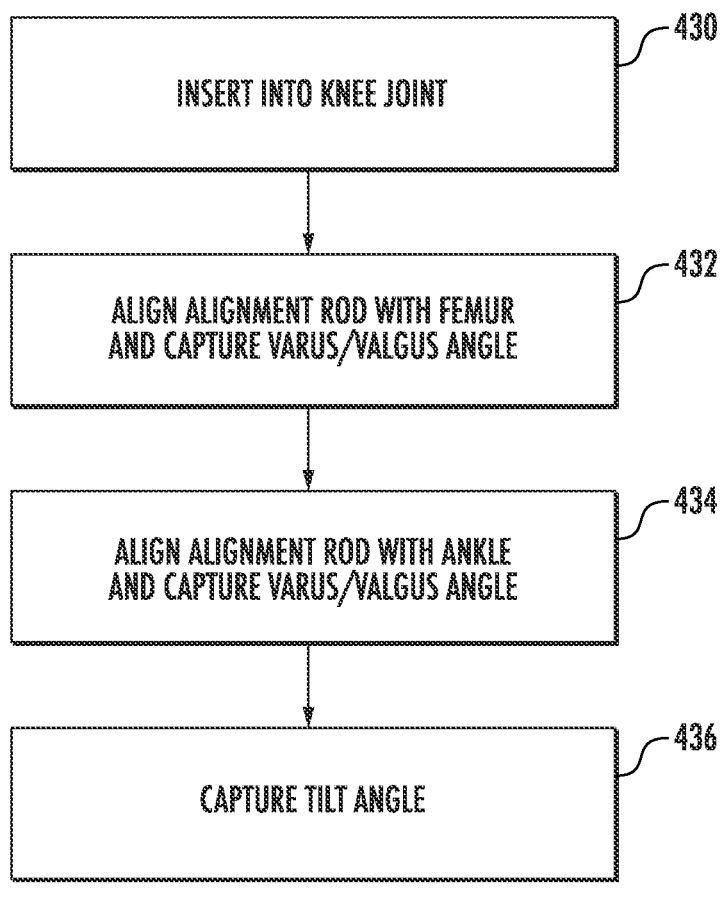
FIG. 20 is a flow diagram illustrating an example technique for making positional orientation/alignment measurements during a knee replacement procedure using an example intraoperative surgical system according to the disclosure.

FIG. 20 is a flow diagram illustrating an example technique for making positional orientation/alignment measurements during a knee replacement procedure using an example intraoperative surgical system according to the disclosure. The example technique of FIG. 20 will be described with respect to FIGS. 21 and 22 and an example configuration of intraoperative surgical system 100 but can be performed with systems having other configurations as described herein.

In the example of FIG. 20, the surgeon surgically accesses the tibiofemoral joint and inserts sensor support body 102 carrying one or more position sensors 310 into the knee joint (430). For example, with reference to FIG. 21, the clinician may insert an alignment rod for 28 through alignment rod receiving hole 154 of sensor support body 102 and couple electronics housing 110 carrying one or more position sensors 310 to the sensor support body. The clinician may insert sensor support body 102 carrying the one or more position sensors 310 prior to resecting either of femur 12 or tibia 14, or after resecting one or both bones.

For example, the clinician may typically resect one or both of femur 12 and tibia 14 and then perform an alignment measurements using intraoperative sensor system 100 to check the alignment of the cut end faces of one or both bones. This can help provide information to the clinician concerning the alignment of one or both end faces and indicate to the clinician whether corrective resection is desired of one or both end faces.

Figure 21:
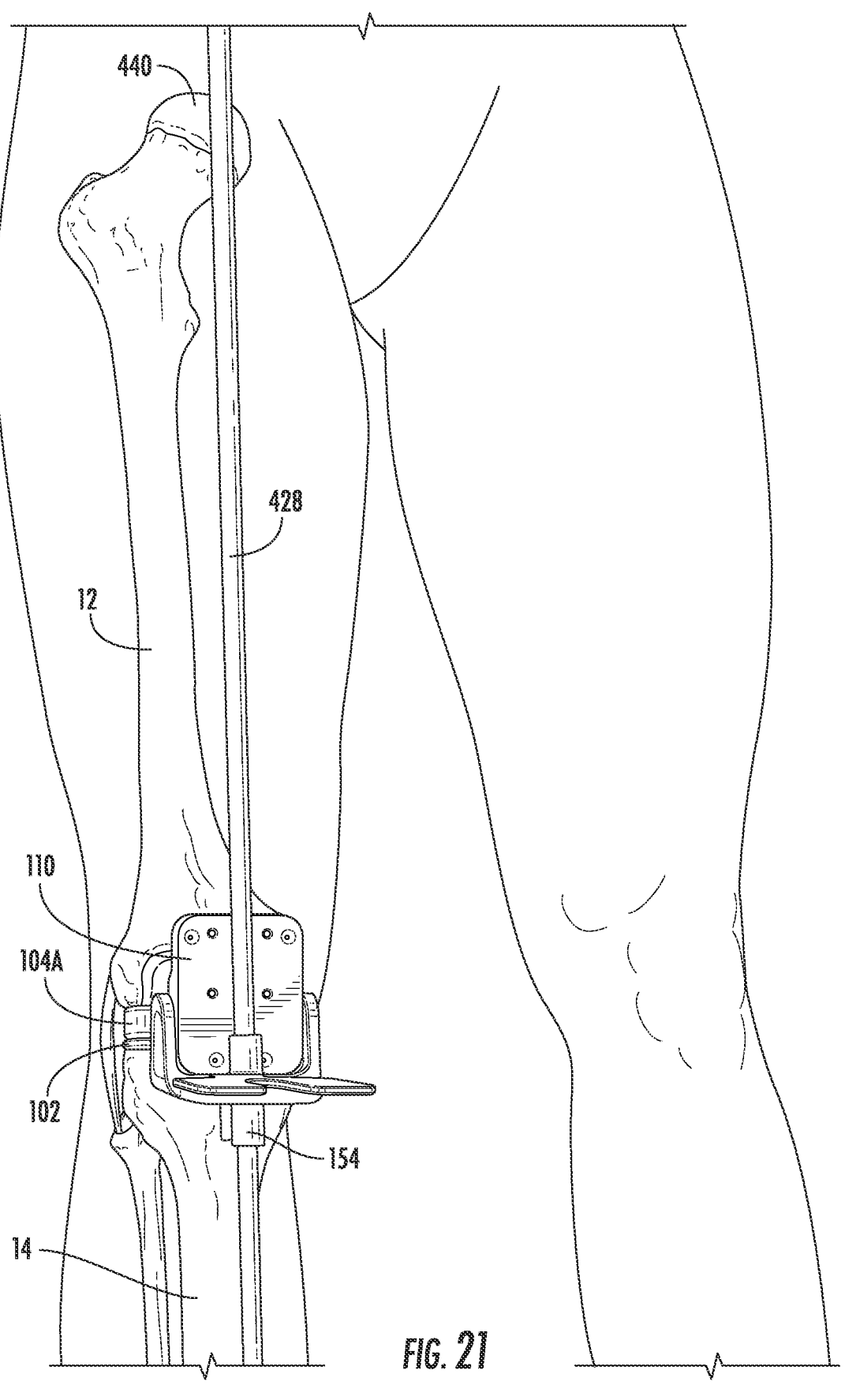
FIGS. 21 and 22 are illustrations of example technique steps that can be performed in conjunction with the technique of FIG. 15.

In the example illustrated in FIG. 21, for instance, the distal end of femur 12 has been resected to remove a distal-most portion of the bone, and the proximal end of tibia 14 has been resected to remove a proximal-most portion of the bone. The clinician can select a sensor cover, such as sensor cover 104A, from a system of different thickness sensor covers corresponding to the size of the gap between the end faces of the femur and tibia. The clinician can attach the sensor cover to sensor support body 102 and insert the resulting joint insertion block into the tibiofemoral joint space. The clinician may or may not position one or more force sensors 106 between the sensor support body and the sensor cover when performing the alignment technique. For example, the alignment technique may be performed without making force measurements across tibiofemoral joint space (and, in some examples, may be performed with the configuration of intraoperative surgical system 100 having one or more position sensors but without having any force sensors). Alternatively, the alignment technique may be performed with one or more force sensors 106 positioned between the sensor support body and the sensor cover. Accordingly, while the technique of FIG. 20 as described separately from the example load measurement technique of FIG. 15, an alignment measurement technique can be performed concurrent with any desired steps of the load measurement technique according to disclosure.

With further reference to FIG. 21, the clinician can insert alignment rod 428 through alignment rod receiving aperture 154 before or after inserting the joint insertion portion of sensor support body 102 into the tibiofemoral joint space. The clinician may position electronics housing 110 carrying one or more position sensors 310 anteriorly of the joint space (e.g., substantially centered in the medial-to-lateral direction in the coronal plane). When position sensor 310 includes a multi-axis accelerometer, one axis of the accelerometer may be parallel to alignment rod 428. In some examples, the clinician interacts with user interface 312 of external device 300 to inform the system when the sensor support body 102 carrying electronics housing 110 is at initial orientation in the joint space from which subsequent positional changes are measured.

In the example technique of FIG. 20, the clinician moves alignment rod 428, and the one or more position sensors 310 operatively connected to the alignment rod, to align a proximal portion of the alignment rod with the head for 440 of femur 12 and captures a varus/valgus angle of the femur in the coronal plane using the one or more position sensors (432). For example, the clinician can rotate sensor support body 102 carrying alignment rod 428 and the one or more position sensors 310 in electronics housing 110 in the medial-to-lateral direction in the coronal plane until the proximal tip of the alignment rod is positioned at the center of the femoral head 440 of femur 12. The proximal tip of alignment rod 428 maybe at the center of the femoral head when the proximal tip of the alignment rod points to, extends over, or is positioned past the center of the femoral head. The center of the femoral head may be a location on the femoral head between the medial-most and lateral-most extents of the femoral head. In practice, the clinician may palpate and estimate the location of the femoral head using the greater trochanter and/or anterior superior iliac spin (ASIS) as an anatomical reference. The clinician can approximate the center location of the femoral head based on visual inspection and/or radiographic measurements, recognizing in practice that the alignment rod may not be positioned exactly over the center of the femoral head but rather the clinician's approximation of the center of the femoral head.

When rotating sensor support body 102 in the coronal plane, the joint insertion portion of the sensor support body can remain in the tibiofemoral joint space. The clinician position a depth stop of sensor support body 102 in contact with an anterior rim of tibia 14 and rotate the sensor support body about the contact point. For example, the clinician may not adjust the anterior to posterior positioning of sensor support body 102 in the joint space when aligning alignment rod 428 but instead may rotate the sensor support body in the medial direction and/or lateral direction from the neutral starting position while maintaining the sensor support body at substantially the same anterior to posterior depth in the joint space. The clinician may make an alignment measurement of the end face of femur 12 when the leg is in extension and/or one or more flexion positions. For example, the clinician may place the leg in extension with the foot pointed upwards when performing the technique of FIG. 20.

When making a femoral alignment measurement, the clinician can press sensor support body 102, directly or indirectly, against the distal head of the femur. For example, the clinician may place a planar face of intraoperative surgical system 100, such as a planar face of sensor support body 102 or a planar top face of sensor cover 104A, in contact with the cut distal head of femur 12. This can cause the one or more position sensors 310 carried by the sensor support body to be aligned relative to the cut face of femur 12. The clinician may position sensor support body 102 parallel to the cut face of femur 12, for example by pressing the top surface of the sensor cover in contact with the cut face of the femur, before, during, and/or after rotating the alignment rod 428 relative to the proximal head of femur 12 and capturing an alignment measurement.

With alignment rod 428 suitably positioned (e.g., the alignment rod and leg statically positioned without movement of femur 12 relative to tibia 14), the intraoperative surgical system can capture a varus/valgus angle of femur 12 in the coronal plane using the one or more position sensors 310. The varus/valgus angle of femur 12 can indicate a medial/lateral incline of the cut head of femur 12 in the coronal plane. A valgus slope can correspond to a lateral superior-to-medial inferior slope on the distal end of femur 12 whereas a varus slope can correspond to a medial superior-to-lateral inferior slope on the distal end of femur 12. A neutral or 0 degree angle can indicate that there is no medial-to-lateral sloping of the end face in the coronal plane.

The one or more position sensors 310 can generate a multi-axis position measurement, such as a three-axis acceleration measurement, indicative of the position the sensor and, correspondingly, the cut end of femur 12. The degree of rotation of alignment rod 428 and electronics housing 110 containing the one or more position sensors 310 during alignment of the rod can correspond to the varus/valgus angle of femur 12 in the coronal plane.

One or more processors 302 in electronics housing 110 and/or one or more other processors remote from electronics housing 110 can receive and process measurement information generated by the one or more position sensors 310 to provide an indication of the varus/valgus angle of femur 12 in the coronal plane suitable for display on the user interface 312. For example, external device 300 may receive data indicative of position/alignment measurements made by position sensors 310 for display on user interface 312. External device 300 may display position information graphically (e.g., color coding), textually (e.g., numerically), and/or in another format discernible to the clinician. The one or more processors 302 in electronics housing 110 and/or one or more other processors remote from electronics housing 110 can capture (e.g., receive and/or process) measurement information generated by the one or more position sensors 310 to determine a varus/valgus angle of femur 12 automatically (e.g., in response to rotation of the alignment rod and position sensors 310 terminating) and/or in response to a clinician input via external device 300. In some examples, the clinician interacts with user interface 312 of external device 300 to inform the system when the sensor support body 102 carrying position sensors 310 is a final rotation position with alignment rod 428 positioned at the center of the proximal head of femur 12.

Figure 22:
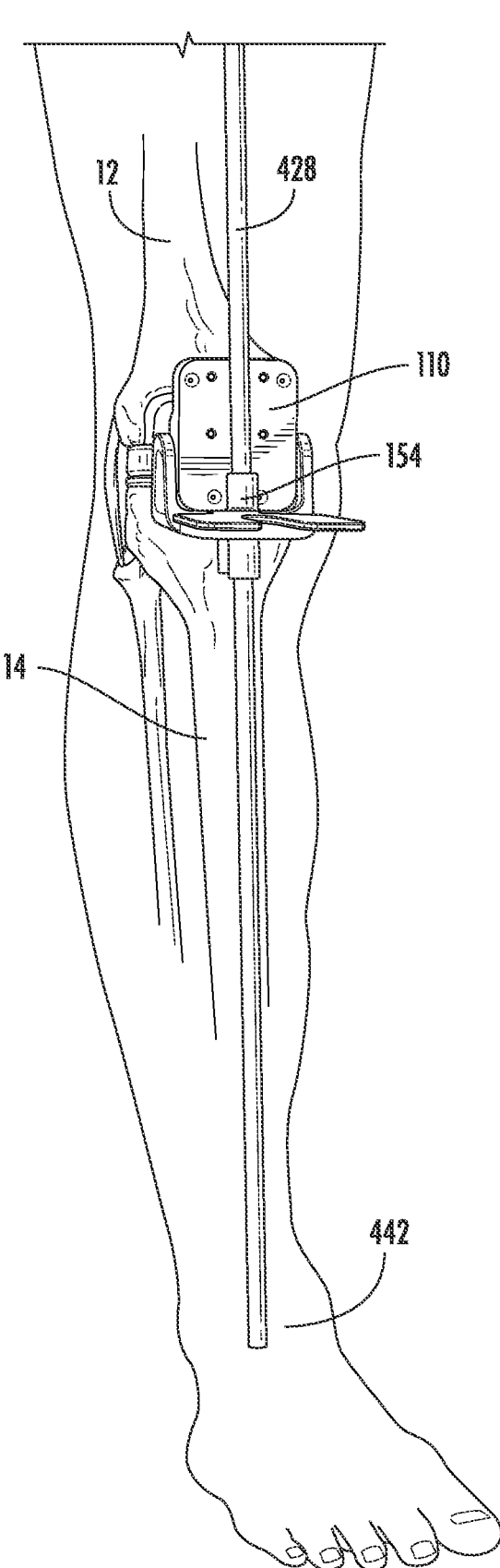

With reference to FIGS. 20 and 22, the example technique of FIG. 20 also involves the clinician moving alignment rod 428, and the one or more position sensors 310 operatively connected to the alignment rod, to align a distal portion of the alignment rod with the distal end of tibia 14 (e.g., ankle 442 defining the talocrural joint) and capturing a varus/valgus angle of the tibia in the coronal plane using the one or more position sensors (434). The clinician can capture the varus/valgus angle of the tibia before or after capturing the varus/valgus angle of the femur, and the order of operation is not limited to the example illustrated in FIG. 20.

The clinician can rotate sensor support body 102 carrying alignment rod 428 and the one or more position sensors 310 in electronics housing 110 in the medial-to-lateral direction in the coronal plane until the distal tip of the alignment rod is positioned at the center of ankle 442 (and/or distal end of tibia 14). The distal tip of alignment rod 428 maybe at the center of the ankle when the distal tip of the alignment rod points to, extends over, or is positioned past the center of the ankle. The center of the ankle may be a location on the talocrural joint between the medial-most and lateral-most extents of the joint. The clinician can approximate the center location of the ankle based on visual inspection and/or radiographic measurements, recognizing in practice that the alignment rod may not be positioned exactly over the center of the ankle but rather the clinician's approximation of the center of the ankle.

When rotating sensor support body 102 in the coronal plane, the joint insertion portion of the sensor support body can remain in the tibiofemoral joint space, as discussed above with respect to step (432). The clinician may make an alignment measurement of the proximal end face of tibia 14 when the leg is in extension and/or one or more flexion positions. For example, the clinician may place the leg in extension with the foot pointed upwards when performing the technique of FIG. 20.

When making a tibial alignment measurement, the clinician can press sensor support body 102, directly or indirectly, against the proximal head of the tibia. For example, the clinician may place a planar face of intraoperative surgical system 100, such as a planar bottom face of sensor support body 102, in contact with the cut proximal face of tibia 14. This can cause the one or more position sensors 310 carried by the sensor support body to be aligned relative to the cut face of tibia 14. The clinician may position sensor support body 102 parallel to the cut face of tibia 14, for example by pressing the bottom surface of the sensor support body in contact with the cut face of the tibia, before, during, and/or after rotating the alignment rod 428 relative to the ankle and capturing an alignment measurement.

With alignment rod 428 suitably positioned (e.g., the alignment rod and leg statically positioned without movement of femur 12 relative to tibia 14), the intraoperative surgical system can capture a varus/valgus angle of tibia 14 in the coronal plane using the one or more position sensors 310. The varus/valgus angle of tibia 14 can indicate a medial/lateral inclination of the cut head of tibia 14 in the coronal plane. A varus slope can correspond to a lateral superior-to-medial inferior slope on the proximal end of tibia 14 whereas a valgus slope can correspond to a medial superior-to-lateral inferior slope on the proximal end of tibia 14. A neutral or 0 degree angle can indicate that there is no medial-to-lateral sloping of the end face in the coronal plane. The one or more position sensors 310 can generate a multi-axis position measurement, such as a three-axis acceleration measurement, indicative of the position the sensor and, correspondingly, the cut end of tibia 14. The degree of rotation of alignment rod 428 and electronics housing 110 containing the one or more position sensors 310 during alignment of the rod can correspond to the varus/valgus angle of tibia 14 in the coronal plane.

One or more processors 302 in electronics housing 110 and/or one or more other processors remote from electronics housing 110 can receive and process measurement information generated by the one or more position sensors 310 to provide an indication of the varus/valgus angle of tibia 14 in the coronal plane suitable for display on the user interface 312. For example, external device 300 may receive data indicative of position/alignment measurements made by position sensors 310 for display on user interface 312. External device 300 may display position information graphically (e.g., color coding), textually (e.g., numerically), and/or in another format discernible to the clinician. The one or more processors 302 in electronics housing 110 and/or one or more other processors remote from electronics housing 110 can capture (e.g., receive and/or process) measurement information generated by the one or more position sensors 310 to determine a varus/valgus angle of tibia 14 automatically (e.g., in response to rotation of the alignment rod and position sensors 310 terminating) and/or in response to a clinician input via external device 300. In some examples, the clinician interacts with user interface 312 of external device 300 to inform the system when the sensor support body 102 carrying position sensors 310 is a final rotation position with alignment rod 428 positioned at the center of the ankle.

The example technique of FIG. 20 also includes capturing a tilt angle of tibia 14 in the sagittal plane using one or more position sensors 310 (436). The clinician can capture the tilt angle as a standalone step or before or after capturing the varus/valgus angle of femur 12 and/or tibia 14. The clinician can insert sensor support body 102 carrying one or more position sensors 310 into the tibiofemoral joint space. The clinician may place a planar face of intraoperative surgical system 100, such as a planar bottom face of sensor support body 102, in contact with the cut proximal face of tibia 14. This can cause the one or more position sensors 310 carried by the sensor support body to be aligned relative to the cut face of tibia 14. The clinician may position sensor support body 102 parallel to the cut face of tibia 14, for example by pressing the bottom surface of the sensor support body in contact with the cut face of the tibia. The leg may be placed in extension, and the clinician may position electronics housing 110 carrying one or more position sensors 310 anteriorly of the joint space (e.g., extending perpendicularly from the joint space), as illustrated in FIG. 21.

With the sensor support body or a feature carried thereby positioned in contact with the cut distal end face of femur 12 both anteriorly and posteriorly across the face of the femur, the clinician may then tilt the portion of the sensor support body extending out of the joint in a superior direction in the sagittal plane, causing the portion in the joint to move inferiorly, e.g., until the bottom surface of the sensor support body (or a feature carried thereon) contacts the opposed cut end face of tibia 14. When so positioned, the posterior portion of sensor support body 102 in the tibiofemoral joint space may contact the cut end face of tibia 14 and the anterior portion of sensor support body in the tibiofemoral joint space may contact the cut end face of femur 12 (e.g., with top surface of sensor cover 104 carried by the sensor support body contacting the cut face of the femur on an anterior side). The resulting angle can correspond to the tilt angle of tibia 14 in the sagittal plane.

One or more processors 302 in electronics housing 110 and/or one or more other processors remote from electronics housing 110 can receive and process measurement information generated by the one or more position sensors 310 to provide an indication of the tilt angle of tibia 14 in the sagittal plane suitable for display on the user interface 312. For example, external device 300 may receive data indicative of position/alignment measurements made by position sensors 310 for display on user interface 312. External device 300 may display position information graphically (e.g., color coding), textually (e.g., numerically), and/or in another format discernible to the clinician. The one or more processors 302 in electronics housing 110 and/or one or more other processors remote from electronics housing 110 can capture (e.g., receive and/or process) measurement information generated by the one or more position sensors 310 to determine a tilt angle of tibia 14 automatically (e.g., in response to movement of the position sensors 310 terminating) and/or in response to a clinician input via external device 300. In some examples, the clinician interacts with user interface 312 of external device 300 to inform the system when the sensor support body 102 carrying position sensors 310 is a final tilt position.

With further reference to FIG. 19, external device 300 can receive and display positional information indicative of the varus/valgus angle of femur 12, the varus/valgus angle of tibia 14, and/or the tilt angle of tibia 14 (which may also be referred to as the slope of the tibia). For example, device 300 may display a numeral varus/valgus value (e.g., angle) of the femur 450, a numerical varus/valgus value of the tibia 452, and/or a numerical tilt value of the tibia 454. Additionally or alternatively, device 300 may display a numeral mechanical axis value 456, which is determined based on the combination of the varus/valgus angle of femur 12 and the varus/valgus angle of tibia 14. Remote device 300 can display alignment information in other formats, as described herein.

Figure 23:
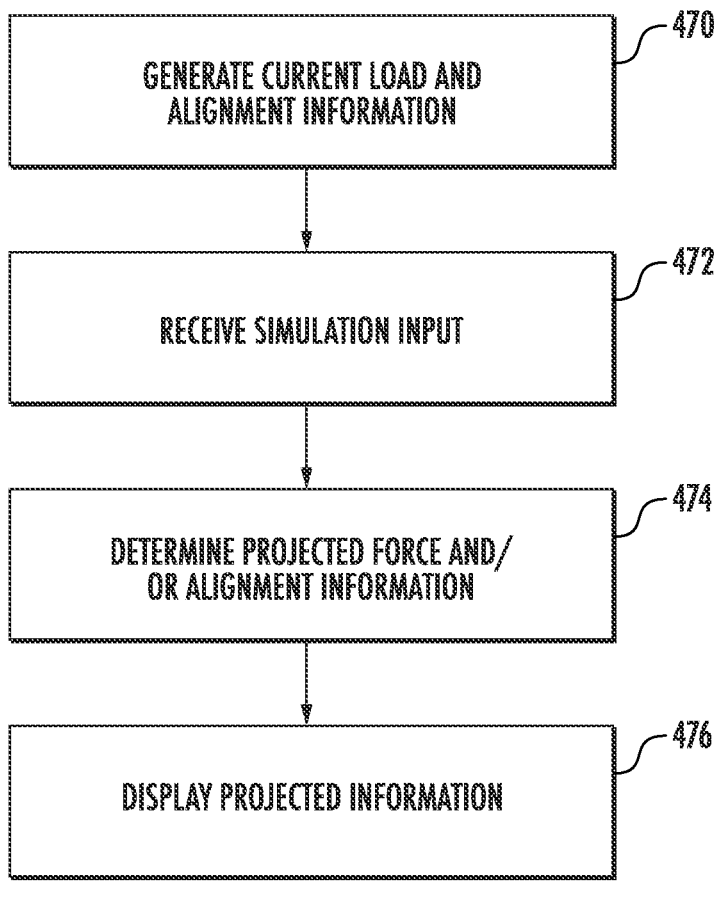
FIG. 23 is a flow diagram illustrating an example technique for simulating adjustment to the load balance across the tibiofemoral joint space prior to surgically implementing changes necessary to effectuate the simulated load balance changes.

FIG. 23 is a flow diagram illustrating an example technique for simulating adjustment to the load balance across the tibiofemoral joint space prior to surgically implementing changes necessary to effectuate the simulated load balance changes. The technique of FIG. 23 involves generating current load and/or alignment data for the tibiofemoral joint space (470). The clinician can generate current load and/or alignment data for the tibiofemoral joint space according to the example techniques discussed above with respect to FIGS. 15 and 20. Measurement data generated can be stored in storage devices 306. For example, load measurement data store 318 may receive and store data indicative of force measurements made by force sensors 106 for the current joint. Position measurement data store 320 may receive and store data indicative of one or more position measurements made by position sensor 310 for the current joint.

The example of FIG. 23 involves receiving a user input simulating a change in a dimensional characteristic of the tibiofemoral joint (472). For example, the clinician may interact with an input function of user interface 312 to input one or more simulated dimensional changes that can be made by the clinician to the tibiofemoral joint space during the surgical procedure. The simulated dimensional change may be indicative of a change in the varus/valgus angle of femur 12, a change in the varus/valgus angle of tibia 14, a change in a spacing between femur 12 and tibia 14 across the tibiofemoral joint, and/or surgically-implementable dimensional change. The clinician may surgically implement a dimensional change to the tibiofemoral joint space by changing in an amount of bone resected from the tibia and/or femur. For example, the clinician may cut an additional amount (e.g., thickness) of the tibia and/or femur off the end of the bone and/or angle a cut in a varus and/or valgus and/or anterior or posterior direction to change the shape of the cut end face of the bone. Additionally or alternatively, the clinician may change the size and/or configuration of one or more prosthetic components installed in the joint space, such as the thickness of the tibia insert 64 (which can also be referred to as the prosthetic bearing) to be inserted between femoral prosthetic component 60 and tibial prosthetic component 62.

The example of FIG. 23 also involves determining one or more forces across the tibiofemoral joint projected in response to the change in the dimension characteristic (474). For example, load balance simulation module 316 may receive one or more simulation requests from external device 300 in response to a surgeon input to external device 300 via user interface 312. Load balance simulation module 316 may simulate load force and/or positional changes to the tibiofemoral joint in response to projected changes entered via user interface 312 by the surgeon with reference. Load balance simulation model 316 may reference simulation data store 322 to determine how one or more simulated changes to the tibiofemoral joint space may affect forces exhibited across the tibiofemoral joint space (e.g., magnitude and/or distribution of forces) as measured by force sensors 106 and/or may affect the varus-valgus angle of the tibiofemoral joint and/or tilt angle of the tibiofemoral joint as measured by position sensor 310. Load balance simulation module 316 may respond to the request by sending information to external device 300. Additionally or alternatively, the functionality of load balance simulation module 316 may execute partially or fully on device 300.

The example of FIG. 23 also involves displaying information indicative of the simulated change to the tibiofemoral joint space, such as displaying information indicative of the force across the tibiofemoral joint projected in response to the change in the dimension characteristic (476). For example, external device 300 can generate and/or receive information indicative of the simulated change to the tibiofemoral joint space for display on user interface 312. Device 300 can control user interface 312 to display the information.

If the simulated data accords with the clinician load balance and/or positional orientation objectives, the clinician may proceed to surgically implement the one or more changes previously simulated (e.g., making one or more bone cuts as simulated, installing a prosthetic component as simulated). If the simulated data is outside of the clinician's target load balance and/or positional orientation objectives, the clinician may input one or more alternative changes and load balance simulation model 316 can make new simulation determinations, which can be subsequently implemented by the surgeon or re-simulated yet again.

Figure 24:
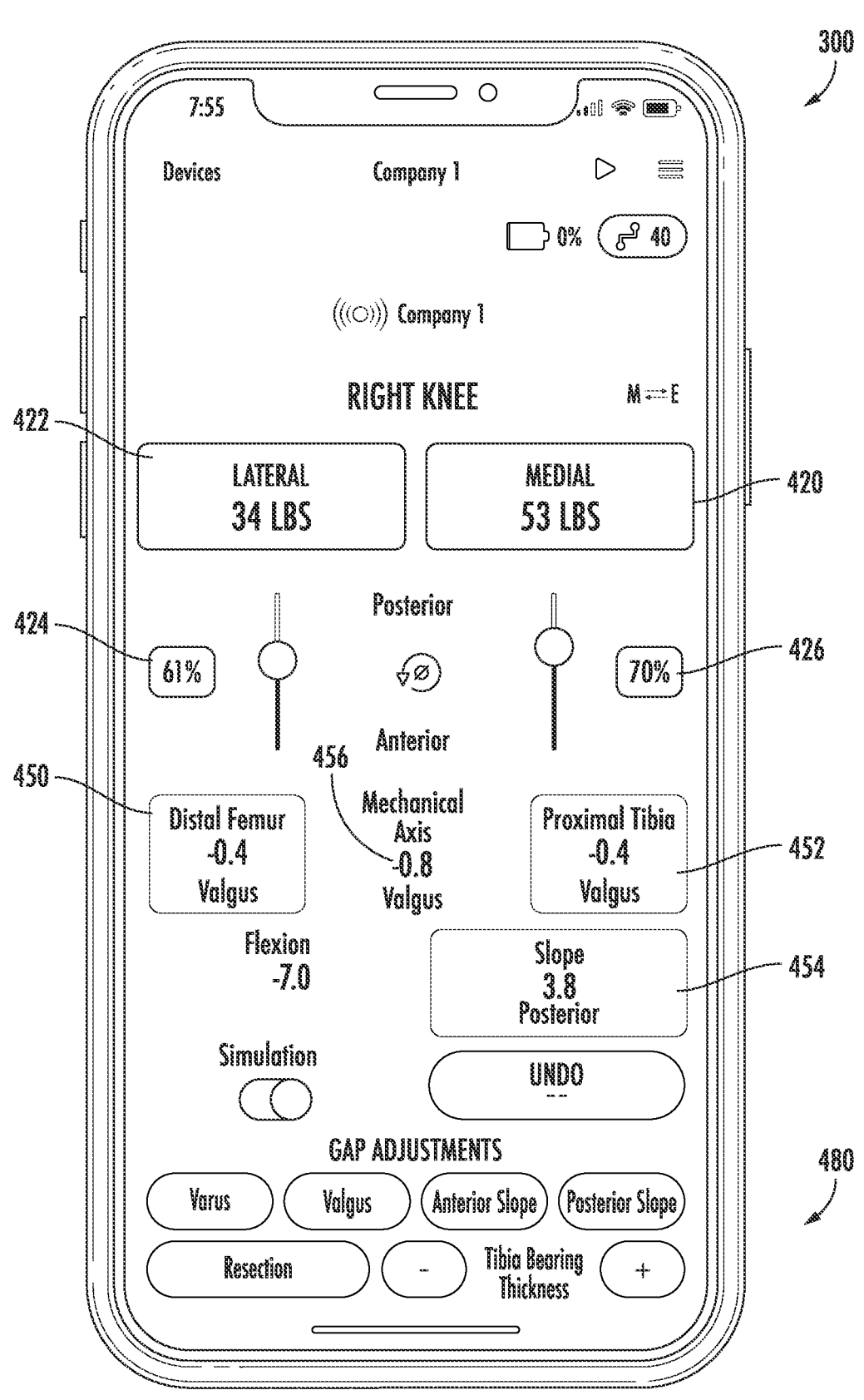
FIG. 24 is an illustration of the example user interface and display output showing an example simulation interface that a clinician can interact with to input information indicating one or more changes to the characteristics of the tibiofemoral joint space.

FIG. 24 is an illustration of the example user interface and display output from FIG. 19 showing an example simulation interface 480 that a clinician can interact with to input information indicating one or more changes to the characteristics of the tibiofemoral joint space. In FIG. 24, the positions of the medial force value 420 display and the lateral force value display 422 are switched compared to FIG. 19. Simulation interface 480 may present buttons, toggles, data entry fields, and/or other input formats allowing the clinician to input one or more desired simulation changes to the tibiofemoral joint space.

Figures 25A, 25B, 25C:
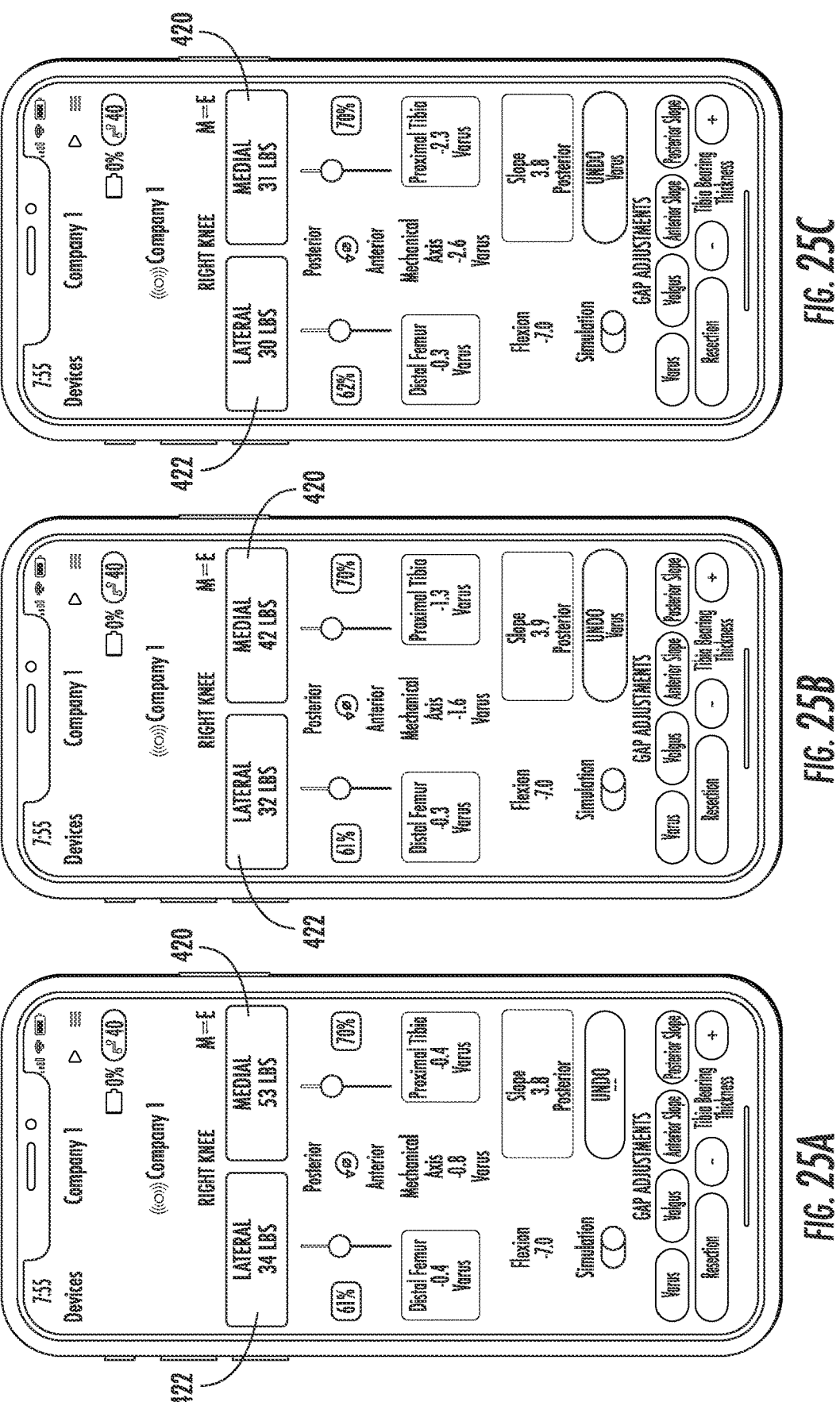
FIGS. 25A-25C illustrate an example set of display outputs that can be displayed via a device when simulating a change to the tibiofemoral joint space.

FIGS. 25A-25C illustrate an example set of display outputs that can be displayed via external device 300 when simulating a change to the tibiofemoral joint space. FIG. 25A illustrates example force and position measurements for the current knee joint (prior to simulation) which, in the illustrated example, exhibits a comparatively high medial force value 420 and a balanced lateral force value 422. Force values may be compared relative to each other and/or one or more thresholds stored in a storage device and an indication displayed whether a force value crosses a threshold and/or is in or out of a target range (e.g., via color coding such as red, yellow, green, and/or blue or other format). FIG. 25B illustrates example force and position measurements in response to simulating a 1 degree varus cut to tibia 14 which, in the illustrated example, exhibits a lower but still comparatively high medial force value 420 and a balanced lateral force value 422. FIG. 25C illustrates example force and position measurements in response to simulating a 2 degree varus cut to tibia 14 which, in the illustrated example, exhibits a balanced medial force value 420 and a balanced lateral force value 422.

Figures 26A, 26B, 26C:
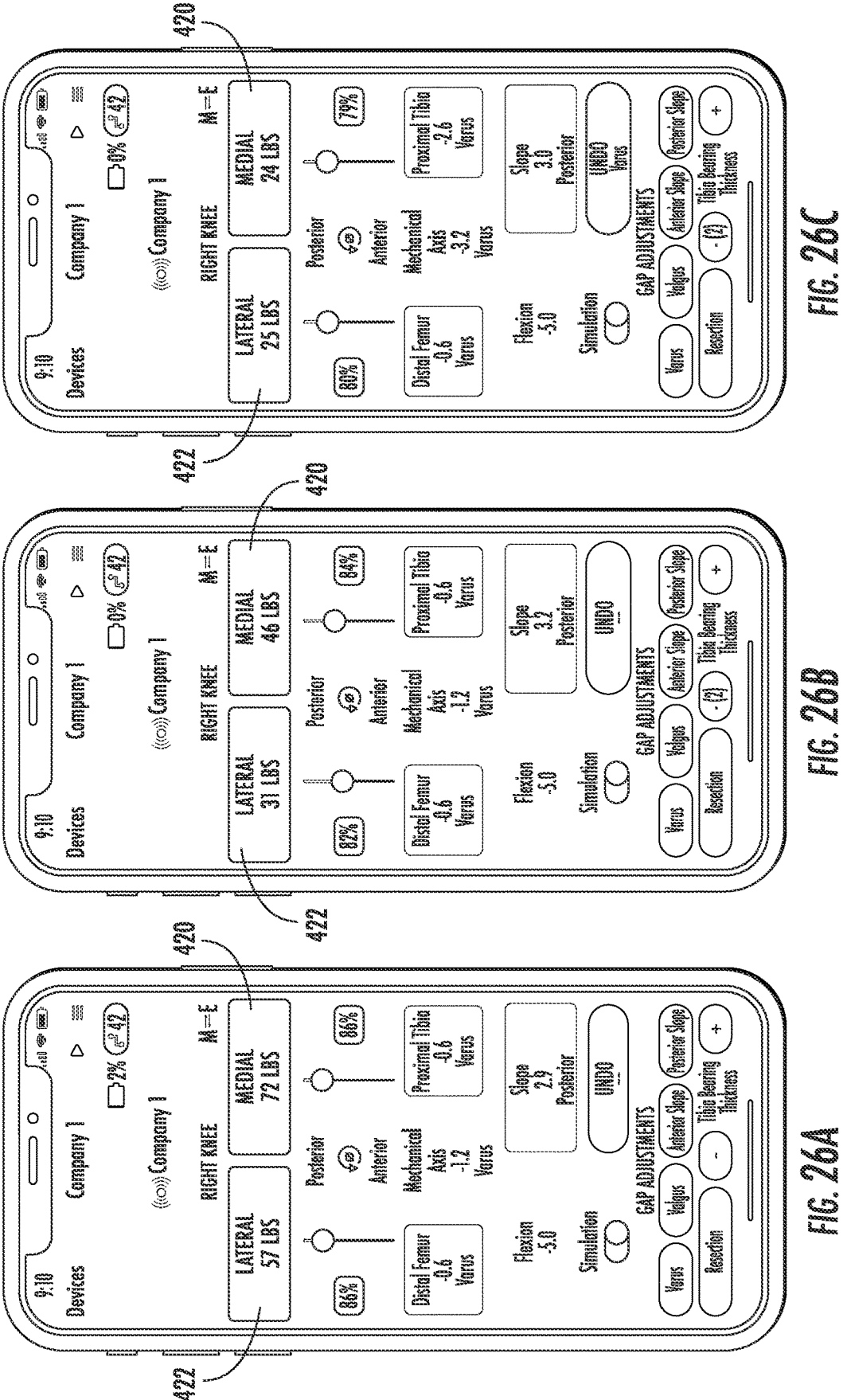
FIGS. 26A-26C illustrate another example set of display outputs that can be displayed via a device when simulating a change to the tibiofemoral joint space.

FIGS. 26A-26C illustrate an example set of display outputs that can be displayed via external device 300 when simulating a change to the tibiofemoral joint space. FIG. 26A illustrates example force and position measurements for the current knee joint (prior to simulation) which, in the illustrated example, exhibits a comparatively high medial force value 420 and a comparatively high lateral force value 422, indicating a tight joint space. FIG. 26B illustrates example force and position measurements in response to simulating 2 mm of additional resection across the joint (which may be taken from femur 12 and/or tibia 14) and, in the illustrated example, exhibits a lower but still comparatively high medial force value 420 and a balanced lateral force value 422. FIG. 25C illustrates example force and position measurements in response to simulating a 2 degree varus cut to tibia 14 (e.g., in addition to the 2 mm resection simulated and displayed in FIG. 25B) which, in the illustrated example, exhibits a balanced medial force value 420 and a balanced lateral force value 422.

Figures 27A, 27B, 27C:
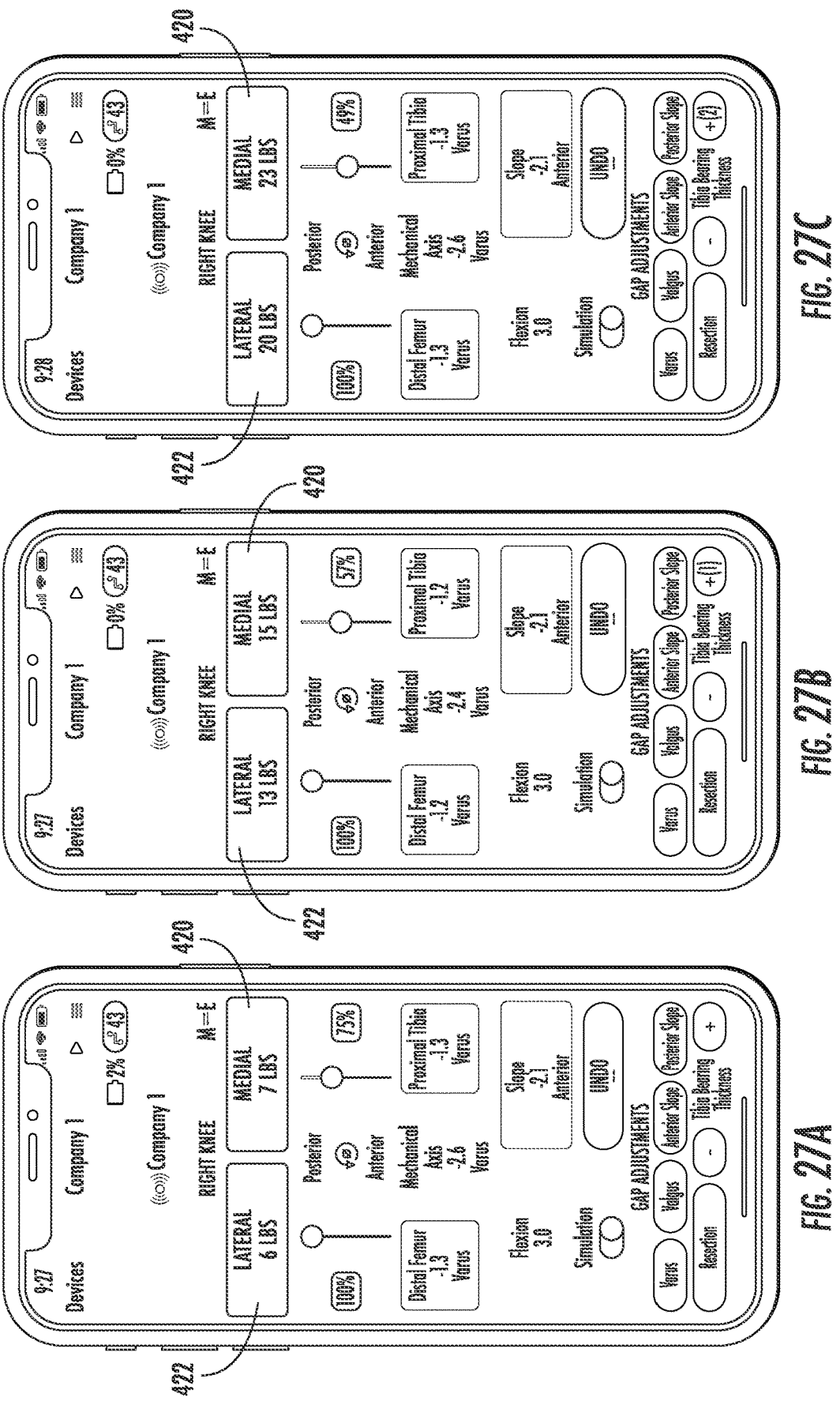
FIGS. 27A-27C illustrate another example set of display outputs that can be displayed via a device when simulating a change to the tibiofemoral joint space.

FIGS. 27A-27C illustrate an example set of display outputs that can be displayed via external device 300 when simulating a change to the tibiofemoral joint space. FIG. 27A illustrates example force and position measurements for the current knee joint (prior to simulation) which, in the illustrated example, exhibits a comparatively low medial force value 420 and a comparatively low lateral force value 422, indicating a loose joint space. FIG. 26B illustrates example force and position measurements in response to simulating installation of a tibial insert 64 that is 1 mm thicker which, in the illustrated example, exhibits a higher but still comparatively lower medial force value 420 and a higher but still comparatively low lateral force value 422. FIG. 25C illustrates example force and position measurements in response to simulating installation of a tibial insert 64 that is 2 mm thicker which, in the illustrated example, exhibits a balanced medial force value 420 and a balanced lateral force value 422.

It should be appreciated that the descriptive terms "top" and "bottom" with respect to the configuration and orientation of components described herein are used for purposes of illustration based on the orientation in the figures. The arrangement of components in real world application may vary depending on their orientation with respect to gravity. Accordingly, unless otherwise specified, the general terms "first" and "second" may be used interchangeably with the terms "top" and "bottom" without departing from the scope of disclosure.

In the examples described above, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses. Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

The invention claimed is:

1. A method of performing bone alignment during a knee arthroplasty procedure, the method comprising:

resecting each of a tibia and a femur defining a tibiofemoral joint;

inserting a sensor support body carrying a position sensor into the tibiofemoral joint with an alignment rod extending through the sensor support body;

rotating the sensor support body in a medial-to-lateral direction until a tip of the alignment rod is positioned at a center of a femoral head of the femur and thereafter capturing a varus/valgus angle of the femur in a coronal plane using the position sensor; and rotating the sensor support body in the medial-to-lateral direction until the tip of the alignment rod is positioned at a center of an ankle and thereafter capturing a varus/valgus angle of the tibia in the coronal plane using the position sensor.

2. The method of claim 1, wherein the position sensor comprises a three-axis accelerometer.

3. The method of claim 1, wherein rotating the sensor support body in the medial-to-lateral direction until the tip of the alignment rod is positioned at the center of the femoral head of the femur comprises pressing the sensor support body against a cut face of the femur in the tibiofemoral joint, optionally with one or more features positioned between the sensor support body and the cut face of the femur.

4. The method of claim 1, wherein rotating the sensor support body in the medial-to-lateral direction until the tip of the alignment rod is positioned at the center of the femoral head of the femur comprises rotating the sensor support body in the medial-to-lateral direction until the tip of the alignment rod is positioned over the center of the femoral head of the femur.

5. The method of claim 1, wherein rotating the sensor support body in the medial-to-lateral direction until the tip of the alignment rod is positioned at the center of the ankle comprises pressing the sensor support body against a cut face of the tibia in the tibiofemoral joint, optionally with one or more features positioned between the sensor support body and the cut face of the tibia.

6. The method of claim 1, wherein rotating the sensor support body in the medial-to-lateral direction until the tip of the alignment rod is positioned at the center of the ankle comprises rotating the sensor support body in the medial-to-lateral direction until the tip of the alignment rod is positioned over the center of the ankle.

7. The method of claim 1, wherein:

rotating the sensor support body in the medial-to-lateral direction until the tip of the alignment rod is positioned at the center of the femoral head of the femur and thereafter capturing the varus/valgus angle of the femur comprises rotating the sensor support body in the medial-to-lateral direction until the tip of the alignment rod is positioned at the center of the femoral head of the femur and thereafter capturing the varus/valgus angle of the femur with the tibiofemoral joint in extension; and rotating the sensor support body in the medial-to-lateral direction until the tip of the alignment rod is positioned at the center of the ankle and thereafter capturing the varus/valgus angle of the tibia comprises rotating the sensor support body in the medial-to-lateral direction until the tip of the alignment rod is positioned at the center of the ankle and thereafter capturing the varus/valgus angle of the tibia with the tibiofemoral joint in extension.

8. The method of claim 1, further comprising an electronics housing containing the position sensor.

9. The method of claim 8, wherein the electronics housing is configured to detachably couple to the sensor support body.

10. The method of claim 1, further comprising displaying via a display of a computing device at least one of the varus/valgus angle of the femur, the varus/valgus angle of the tibia, and a mechanical axis of the tibiofemoral joint.

11. The method of claim 10, comprising displaying the varus/valgus angle of the femur, the varus/valgus angle of the tibia, and the mechanical axis of the tibiofemoral joint.

12. The method of claim 1, wherein rotating the sensor support body in the medial-to-lateral direction until the tip of the alignment rod is positioned at the center of the femoral head of the femur and thereafter capturing the varus/valgus angle of the femur comprises rotating the sensor support body in the medial-to-lateral direction until the tip of the alignment rod is positioned at the center of the femoral head of the femur and thereafter capturing the varus/valgus angle of the femur before rotating the sensor support body in the medial-to-lateral direction until the tip of the alignment rod is positioned at the center of the ankle and thereafter capturing the varus/valgus angle of the tibia.

13. The method of claim 1, comprising:

pressing the sensor support body against a cut face of the tibia in the tibiofemoral joint, optionally with one or more features positioned between the sensor support body and the cut face of the tibia;

tilting a proximal portion of the sensor support body toward the femur; and capturing a tilt angle of the tibia in a sagittal plane using the position sensor.

14. The method of claim 13, further comprising displaying via the display of the computing device the tilt angle.

15. The method of claim 1, further comprising inserting the sensor support body carrying at least one force sensor into the tibiofemoral joint with both the tibia and the femur resected and measuring a force across the tibiofemoral joint.

16. The method of claim 15, wherein inserting the sensor support body carrying at least one force sensor into the tibiofemoral joint comprises inserting the sensor support body carrying at least one force sensor into the tibiofemoral joint after capturing the varus/valgus angle of the femur and after capturing the varus/valgus angle of the tibia.

17. The method of claim 15, wherein:

the at least one force sensor comprises a medial force sensor and a lateral force sensor; and measuring the force across the tibiofemoral joint comprises measuring a medial compartment force via the medial force sensor and a lateral compartment force via the lateral force sensor.

18. The method of claim 17, wherein:

the medial force sensor comprises a medial anterior force sensor and a medial posterior force sensor;

the lateral force sensor comprises a lateral anterior force sensor and a lateral posterior force sensor; and measuring the force across the tibiofemoral joint comprises measuring a medial anterior force via the medial anterior force sensor, a medial posterior force via the medial posterior force sensor, a lateral anterior force via the lateral anterior force sensor, and a lateral posterior force via the lateral posterior force sensor.

19. The method of claim 15, comprising:

receiving, via a user interface of a computing device, a user input simulating a change in a dimensional characteristic of the tibiofemoral joint;

determining, with one or more processors, the force across the tibiofemoral joint projected in response to the change in the dimension characteristic; and displaying, via a display of the computing device, the force across the tibiofemoral joint projected in response to the change in the dimension characteristic.

20. The method of claim 19, wherein the change in the dimensional characteristic comprises:

a change in the varus/valgus angle of the tibia;

a change in the varus/valgus angle of the femur; and/or a change in a spacing between the tibia and the femur across the tibiofemoral joint.

21. The method of claim 20, wherein the change in the spacing between the tibia and the femur across the tibiofemoral joint comprises at least one of:

a change in an amount of bone resected from the tibia and/or femur; and/or a change in a thickness of a prosthetic bearing to be inserted between a femoral prosthetic component to be installed on the femur and a tibial prosthetic component to be installed on the tibia.

22. The method of claim 19, wherein:

the at least one force sensor comprises a medial force sensor and a lateral force sensor;

measuring the force across the tibiofemoral joint comprises measuring a medial compartment force via the medial force sensor and a lateral compartment force via the lateral force sensor;

determining, with one or more processors, the force across the tibiofemoral joint projected in response to the change in the dimension characteristic comprises determining the medial compartment force projected in response to the change in the dimension characteristic and determining the lateral compartment force projected in response to the change in the dimension characteristic; and displaying, via the display of the computing device, the force across the tibiofemoral joint projected in response to the change in the dimension characteristic comprises displaying the medial compartment force projected and the lateral compartment force projected.

23. The method of claim 19, wherein determining, with one or more processors, the force across the tibiofemoral joint projected in response to the change in the dimension characteristic comprises referencing a database relating different force values to different tibiofemoral joint dimensional characteristics.

24. The method of claim 19, further comprising further resecting at least one of the tibia and the femur to implement the change in the dimensional characteristic of the tibiofemoral joint simulated.

* * * * *